(12) United States Patent
Yamakawa et al.

(10) Patent No.: US 12,421,217 B2
(45) Date of Patent: Sep. 23, 2025

(54) PYRAZINE DERIVATIVE OR SALT THEREOF, AND USE OF SAME

(71) Applicant: FUJIFILM Corporation, Tokyo (JP)

(72) Inventors: Takayuki Yamakawa, Ashigarakami-gun (JP); Yasuhiro Tsutsui, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 818 days.

(21) Appl. No.: 17/732,717

(22) Filed: Apr. 29, 2022

(65) Prior Publication Data

US 2022/0259185 A1  Aug. 18, 2022

Related U.S. Application Data

(63) Continuation of application No. PCT/JP2020/040744, filed on Oct. 30, 2020.

(30) Foreign Application Priority Data

Oct. 31, 2019 (JP) .................................. 2019-198280
Jul. 30, 2020 (JP) .................................. 2020-128831

(51) Int. Cl.
  *C07D 405/12*  (2006.01)
(52) U.S. Cl.
  CPC .................. *C07D 405/12* (2013.01)
(58) Field of Classification Search
  CPC ......... C07D 405/12; A61P 43/00; A61P 35/00
  See application file for complete search history.

(56) References Cited

U.S. PATENT DOCUMENTS

| | | | |
|---|---|---|---|
| 2012/0294854 A1 | 11/2012 | Castro Palomino Laria et al. | |
| 2015/0299189 A1 | 10/2015 | Tanaka et al. | |
| 2020/0079727 A1 | 3/2020 | Yang et al. | |

FOREIGN PATENT DOCUMENTS

| | | |
|---|---|---|
| JP | 2010-513362 A | 4/2010 |
| WO | 2014/069510 A1 | 5/2014 |
| WO | 2016/044666 A1 | 3/2016 |
| WO | 2018/157843 A1 | 9/2018 |

OTHER PUBLICATIONS

Wang et al. Discovery of a potent tyrosine kinase AXL inhibitor bearing the 3-((2,3,4,5-tetrahydro-1H-benzo[d]azepin-7-yl)amino pyrazine core (Bioorganic & Medicinal Chemistry Letters, 29, 836-838, Available Online Jan. 21, 2019). (Year: 2019).*
Extended European Search Report dated Oct. 20, 2022 issued in European Application No. 20883361.6.
Office Action issued Apr. 18, 2023 in Japanese Application No. 2021-553708.
Japanese Office Action dated Feb. 7, 2023 in Japanese Application No. 2021-553708.
International Search Report dated Dec. 22, 2020 in International Application No. PCT/JP2020/040744.
Written Opinion of the International Searching Authority dated Dec. 22, 2020 in International Application No. PCT/JP2020/040744.
International Preliminary Report on Patentability dated May 3, 2022 in International Application No. PCT/JP2020/040744.

\* cited by examiner

*Primary Examiner* — Joseph K McKane
*Assistant Examiner* — Meghan C Heasley
(74) *Attorney, Agent, or Firm* — Sughrue Mion, PLLC

(57) ABSTRACT

An object of the present invention is to provide a compound useful as an anti-tumor agent or the like, as well as a pharmaceutical composition, an anti-tumor agent, and a dihydroorotate dehydrogenase inhibitor, each of which contains the compound. According to the present invention, a compound represented by General Formula (1) or a salt thereof is provided.

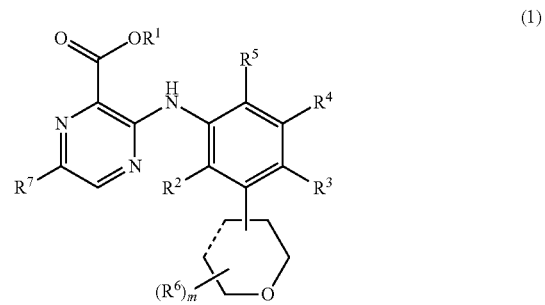

(1)

In the formula, $R^1$ represents a hydrogen atom or a $C_{1-6}$ alkyl group; $R^2$, $R^3$, $R^4$, and $R^5$ are the same as or different from each other and each represent a hydrogen atom, a halogen atom, a $C_{1-6}$ alkyl group which may be substituted, a $C_{1-6}$ alkoxy group which may be substituted, or the like; $R^6$'s are the same as or different from each other and each represent a halogen atom, a $C_{1-6}$ alkyl group which may be substituted, or a $C_{1-6}$ alkoxy group which may be substituted; $R^7$ represents a $C_{3-8}$ cycloalkyl group which may be substituted, or the like; m represents an integer of 0 to 6; and a broken line represents a single bond or a double bond.

15 Claims, No Drawings

PYRAZINE DERIVATIVE OR SALT THEREOF, AND USE OF SAME

CROSS-REFERENCE TO RELATED APPLICATIONS

This application is a Continuation of PCT International Application No. PCT/JP2020/040744 filed on Oct. 30, 2020, which claims priority under 35 U.S.C § 119(a) to Japanese Patent Application No. 2019-198280 filed on Oct. 31, 2019 and Japanese Patent Application No. 2020-128831 filed on Jul. 30, 2020. Each of the above application(s) is hereby expressly incorporated by reference, in its entirety, into the present application.

BACKGROUND OF THE INVENTION

1. Field of the Invention

The present invention relates to a pyrazine derivative or a salt thereof useful as an anti-tumor agent or the like. The present invention further relates to a pharmaceutical composition, an anti-tumor agent, and a dihydroorotate dehydrogenase inhibitor, each of which contains the pyrazine derivative or a salt thereof.

2. Description of the Related Art

Cancer is a major health problem in modern medicine and is one of the leading causes of death in developed countries. Examples of the main cancer include blood cancer and solid cancer.

There are blood cells such as red blood cells, leukocytes, and platelets in the blood, and these blood cells are produced by cell growth and differentiation (a transition from an immature cell into a mature cell) from hematopoietic stem cells, which are the source of blood cells, in the bone marrow inside the bone. Blood cancer develops in a case where some genetic abnormality occurs in myeloblasts, which are immature blood cells in the hematopoietic process, and then cancerous cells (leukemia cells) proliferate indefinitely.

On the other hand, WO2014/069510A discloses a pyrazine derivative which has an excellent keratinocyte growth inhibitory effect and is useful for treatment such as prevention or treatment of a disease associated with keratinocyte overgrowth.

SUMMARY OF THE INVENTION

There are various therapeutic methods for blood cancer such as chemotherapy, radiotherapy, molecularly targeted therapy, and high-dose chemotherapy combined with hematopoietic stem cell transplantation. However, the number of deaths from blood cancer is increasing, and there are problems such as resistance to therapeutic drugs, and no cure has been established.

In addition, most solid cancers have a poor prognosis, and no effective therapeutic method has been established yet. In addition, those cancer cells proliferate autonomously in an uncontrolled manner, which leads to a problem of rapid cancer cell proliferation, and therefore an effective therapeutic method for solid cancer is required.

Various methods are known as methods for preventing or treating cancer, but their effects are not satisfactory, and more effective anti-tumor agents are desired. An object of the present invention is to provide a pyrazine derivative or a salt thereof useful as an anti-tumor agent or the like. Another object of the present invention is to provide a pharmaceutical composition, an anti-tumor agent, and a dihydroorotate dehydrogenase inhibitor, each of which contains the pyrazine derivative or a salt thereof.

The present invention has been made in view of such circumstances. As a result of extensive studies, the present inventors have found that a compound represented by General Formula (1) or a salt thereof has an excellent inhibitory effect on dihydroorotate dehydrogenase (hereinafter, also referred to as DHODH) and is useful as a DHODH inhibitor. In addition, the present inventors have found that the compound represented by General Formula (1) or a salt thereof has an excellent anti-tumor activity and is useful as an anti-tumor agent. The present invention has been completed based on these findings.

The present invention provides the followings.

[1] A compound represented by General Formula (1) or a salt thereof:

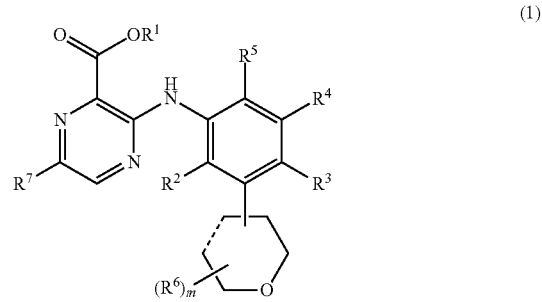

(1)

in the formula, $R^1$ represents a hydrogen atom or a $C_{1-6}$ alkyl group;

$R^2$, $R^3$, $R^4$, and $R^5$ are the same as or different from each other, and each represent a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted;

$R^6$'s are the same as or different from each other and each represent a halogen atom, a $C_{1-6}$ alkyl group which may be substituted, or a $C_{1-6}$ alkoxy group which may be substituted;

$R^7$ represents a $C_{1-6}$ alkyl group which may be substituted or a $C_{3-8}$ cycloalkyl group which may be substituted;

m represents an integer of 0 to 6; and a broken line represents a single bond or a double bond.

[2] The compound or salt thereof according to [1], in which the compound represented by General Formula (1) is a compound represented by General Formula (1a):

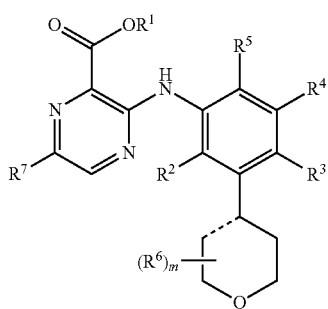

(1a)

in the formula,
R¹ represents a hydrogen atom or a $C_{1-6}$ alkyl group;
R², R³, R⁴, and R⁵ are the same as or different from each other, and each represent a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted;
R⁶'s are the same as or different from each other and each represent a halogen atom, a $C_{1-6}$ alkyl group which may be substituted, or a $C_{1-6}$ alkoxy group which may be substituted;
R⁷ represents a $C_{1-6}$ alkyl group which may be substituted or a $C_{3-8}$ cycloalkyl group which may be substituted;
m represents an integer of 0 to 6; and
a broken line represents a single bond or a double bond.

[3] The compound or salt thereof according to [1] or [2], in which R¹ is a hydrogen atom.

[4] The compound or salt thereof according to any one of [1] to [3], in which R², R³, R⁴, and R⁵ are the same as or different from each other and each are a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A, Substituent Group A:
a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent group B; and a heterocyclic group which may be substituted with one or more substituents selected from Substituent group B Substituent Group B:
a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

[5] The compound or salt thereof according to any one of [1] to [4], in which R² is a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

[6] The compound or salt thereof according to any one of [1] to [5], in which R³, R⁴, and R⁵ are the same as or different from each other and each are a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A.

[7] The compound or salt thereof according to any one of [1] to [6], in which R⁶'s are the same as or different from each other and each are a halogen atom, a $C_{1-6}$ alkyl group which may be substituted with one or more substituents selected from Substituent group A, or a $C_{1-6}$ alkoxy group which may be substituted with one or more substituents selected from Substituent group A.

[8]
The compound or salt thereof according to any one of [1] to [7], in which R⁷ is a $C_{1-6}$ alkyl group or a $C_{3-8}$ cycloalkyl group.

[9]
The compound or salt thereof according to any one of [1] to [7], in which R⁷ is a cyclopropyl group.

[10] The compound or salt thereof according to any one of [1] to [9], in which m is an integer of 0 to 2.

[11] A pharmaceutical composition including the compound or salt thereof according to any one of [1] to [10].

[12] An anti-tumor agent including the compound or salt thereof according to any one of [1] to [10].

[13] A dihydroorotate dehydrogenase inhibitor including the compound or salt thereof according to any one of [1] to [10].

[A] A method for treating a tumor, including administering the compound or salt thereof according to any one of [1] to [10] to a subject.

[B] A method for inhibiting dihydroorotate dehydrogenase, including administering the compound or salt thereof according to any one of [1] to [10] to a subject.

[C] The compound or salt thereof according to any one of (1) to (10), for use in the treatment of a tumor.

[D] The compound or salt thereof according to any one of [1] to [10], for use in the treatment for inhibiting dihydroorotate dehydrogenase.

[E] Use of the compound or salt thereof according to any one of (1) to (10) for the production of a pharmaceutical composition.

[F] Use of the compound or salt thereof according to any one of (1) to (10) for the production of an anti-tumor agent.

[G] Use of the compound or salt thereof according to any one of [1] to [10] for the production of a dihydroorotate dehydrogenase inhibitor.

The compound of the present invention or a salt thereof has an excellent DHODH inhibitory effect and is useful as a DHODH inhibitor.

In addition, the compound of the present invention or a salt thereof has an excellent anti-tumor activity and is useful as a pharmaceutical composition such as an anti-tumor agent. The compound of the present invention or a salt thereof is useful for treatment such as prevention or treatment of blood cancer.

DESCRIPTION OF THE PREFERRED EMBODIMENTS

Hereinafter, the present invention will be described in detail.

"%" as used in the present invention means mass percentage unless otherwise specified. In the present invention, any numerical range indicated using a term "to" indicates a range including numerical values described before and after the "to" as a minimum value and a maximum value, respectively. Further, in the present invention, in a case where a plurality of substances corresponding to components are present in the composition, the amount of each component in the composition means a total amount of the plurality of substances present in the composition, unless otherwise specified.

In the present invention, the individual terms have the following meanings, unless otherwise specified.

The halogen atom refers to a fluorine atom, a chlorine atom, a bromine atom, or an iodine atom.

The $C_{1-6}$ alkyl group refers to a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, or a hexyl group.

The $C_{1-6}$ alkylsulfonyl group refers to a $C_{1-6}$ alkylsulfonyl group such as a methylsulfonyl group, an ethylsulfonyl group, or a propylsulfonyl group.

The $C_{1-6}$ alkylsulfonyloxy group refers to a $C_{1-6}$ alkylsulfonyloxy group such as a methylsulfonyloxy group or an ethylsulfonyloxy group.

The $C_{2-6}$ alkenyl group refers to a linear or branched $C_{2-6}$ alkenyl group such as a vinyl group, an allyl group, a propenyl group, an isopropenyl group, a butenyl group, an isobutenyl group, a 1,3-butadienyl group, a pentenyl group, or a hexenyl group.

The $C_{2-6}$ alkynyl group refers to a linear or branched $C_{2-6}$ alkynyl group such as an ethynyl group, a propynyl group, a butynyl group, a pentynyl group, or a hexynyl group.

The $C_{3-8}$ cycloalkyl group refers to a $C_{3-8}$ cycloalkyl group such as a cyclopropyl group, a cyclobutyl group, a cyclopentyl group, a cyclohexyl group, or a cycloheptyl group.

The $C_{1-6}$ alkylamino group refers to a linear or branched $C_{1-6}$ alkylamino group such as a methylamino group, an ethylamino group, a propylamino group, an isopropylamino group, a butylamino group, a sec-butylamino group, a tert-butylamino group, a pentylamino group, or a hexylamino group.

The di($C_{1-6}$ alkyl)amino group refers to a linear or branched di($C_{1-6}$ alkyl)amino group such as a dimethylamino, a diethylamino group, a dipropylamino group, a diisopropylamino group, a dibutylamino group, a di(tert-butyl)amino group, a dipentylamino group, a dihexylamino group, an (ethyl)(methyl)amino group, or a (methyl)(propyl)amino group.

The $C_{1-6}$ alkoxy group refers to a linear or branched $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group, or a hexyloxy group.

The $C_{1-6}$ alkoxy $C_{1-6}$ alkyl group refers to a $C_{1-6}$ alkyloxy $C_{1-6}$ alkyl group such as a methoxymethyl group or a 1-ethoxyethyl group.

The $C_{1-6}$ alkoxycarbonyl group refers to a linear or branched $C_{1-6}$ alkyloxycarbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, or a hexyloxycarbonyl group.

The $C_{3-8}$ cycloalkoxy group refers to a $C_{3-8}$ cycloalkyloxy group such as a cyclopropoxy group, a cyclobutoxy group, a cyclopentyloxy group, a cyclohexyloxy group, or a cycloheptyloxy group.

The aryl group refers to a phenyl group, a naphthyl group, or the like.

The aryloxy group refers to a phenoxy group, a naphthalen-1-yloxy group, a naphthalen-2-yloxy group, or the like.

The arylsulfonyl group refers to a benzenesulfonyl group, a p-toluenesulfonyl group, a naphthalenesulfonyl group, or the like.

The arylsulfonyloxy group refers to a benzenesulfonyloxy group, a p-toluenesulfonyloxy group, or the like.

The aryl $C_{1-6}$ alkyl group refers to an aryl $C_{1-6}$ alkyl group such as a benzyl group, a diphenylmethyl group, a trityl group, a phenethyl group, a 2-phenylpropyl group, a 3-phenylpropyl group, or a naphthylmethyl group.

The aryl $C_{1-6}$ alkoxy group refers to an aryl $C_{1-6}$ alkyloxy group such as a benzyloxy group, a diphenylmethoxy group, a trityloxy group, a phenethyloxy group, a 2-phenylpropoxy group, a 3-phenylpropoxy group, or a naphthylmethoxy group.

The aryl $C_{1-6}$ alkoxy $C_{1-6}$ alkyl group refers to an aryl $C_{1-6}$ alkyloxy $C_{1-6}$ alkyl group such as a benzyloxymethyl group or a phenethyloxymethyl group.

The aryl $C_{1-6}$ alkoxycarbonyl group refers to an aryl $C_{1-6}$ alkyloxycarbonyl group such as a benzyloxycarbonyl group or a phenethyloxycarbonyl group.

The aryloxycarbonyl group refers to a phenoxycarbonyl group, a naphthalen-1-yloxycarbonyl group, or a naphthalen-2-yloxycarbonyl group.

The heterocyclic ring group refers to a monocyclic heterocyclic ring group, a bicyclic heterocyclic ring group, a spiro heterocyclic ring group, or a bridged heterocyclic ring group.

The monocyclic heterocyclic ring group refers to a monocyclic nitrogen-containing heterocyclic ring group, a monocyclic oxygen-containing heterocyclic ring group, a monocyclic sulfur-containing heterocyclic ring group, a monocyclic nitrogen- and oxygen-containing heterocyclic ring group, or a monocyclic nitrogen- and sulfur-containing heterocyclic ring group.

The monocyclic nitrogen-containing heterocyclic ring group refers to a monocyclic nitrogen-containing heterocyclic ring group which contains only a nitrogen atom as a heteroatom forming the ring, such as an aziridinyl group, an azetidinyl group, a pyrrolidinyl group, a pyrrolinyl group, a pyrrolyl group, a piperidyl group, a tetrahydropyridyl group, a dihydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group, or a tetrazolyl group.

The monocyclic oxygen-containing heterocyclic ring group refers to a monocyclic oxygen-containing heterocyclic ring group which contains only an oxygen atom as a heteroatom forming the ring, such as an oxetanyl group, a tetrahydrofuranyl group, a furanyl group, a tetrahydropyranyl group, a pyranyl group, a 1,3-dioxanyl group, or a 1,4-dioxanyl group.

The monocyclic sulfur-containing heterocyclic ring group refers to a thienyl group.

The monocyclic nitrogen- and oxygen-containing heterocyclic ring group refers to a monocyclic nitrogen- and oxygen-containing heterocyclic ring group which contains only a nitrogen atom and an oxygen atom as heteroatoms forming the ring, such as an oxazolyl group, an isoxazolyl group, an oxadiazolyl group, a morpholinyl group, or an oxazepanyl group.

The monocyclic nitrogen- and sulfur-containing heterocyclic ring group refers to a monocyclic nitrogen- and sulfur-containing heterocyclic ring group which contains only a nitrogen atom and a sulfur atom as heteroatoms forming the ring, such as a thiazolyl group, an isothiazolyl group, a thiadiazolyl group, a thiomorpholinyl group, a 1-oxidothiomorpholinyl group, or a 1,1-dioxidothiomorpholinyl group.

The bicyclic heterocyclic ring group refers to a bicyclic nitrogen-containing heterocyclic ring group, a bicyclic oxygen-containing heterocyclic ring group, a bicyclic sulfur-containing heterocyclic ring group, a bicyclic nitrogen- and oxygen-containing heterocyclic ring group, or a bicyclic nitrogen- and sulfur-containing heterocyclic ring group.

The bicyclic nitrogen-containing heterocyclic ring group refers to a bicyclic nitrogen-containing heterocyclic ring group which contains only a nitrogen atom as a heteroatom forming the ring, such as an indolinyl group, an indolyl group, an isoindolinyl group, an isoindolyl group, a benzimidazolyl group, an indazolyl group, a benzotriazolyl group, a pyrazolopyridinyl group, a quinolyl group, a tetrahydroquinolinyl group, a tetrahydroisoquinolinyl group, an isoquinolinyl group, a quinolizinyl group, a cinnolinyl group, a phthalazinyl group, a quinazolinyl group, a dihydroquinoxalinyl group, a quinoxalinyl group, a naphthyridinyl group, a purinyl group, a pteridinyl group, or a quinuclidinyl group.

The bicyclic oxygen-containing heterocyclic ring group refers to a bicyclic oxygen-containing heterocyclic ring group which contains only an oxygen atom as a heteroatom forming the ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, or a 1,4-benzodioxanyl group.

The bicyclic sulfur-containing heterocyclic ring group refers to a bicyclic sulfur-containing heterocyclic ring group which contains only a sulfur atom as a heteroatom forming the ring, such as a 2,3-dihydrobenzothienyl group or a benzothienyl group.

The bicyclic nitrogen- and oxygen-containing heterocyclic ring group refers to a bicyclic nitrogen- and oxygen-containing heterocyclic ring group which contains only a nitrogen atom and an oxygen atom as heteroatoms forming the ring, such as a benzoxazolyl group, a benzisoxazolyl group, a benzoxadiazolyl group, a benzomorpholinyl group, a dihydropyranopyridyl group, a dioxolopyridyl group, a furopyridinyl group, a dihydrodioxynopyridyl group, or a dihydropyridooxazinyl group.

The bicyclic nitrogen- and sulfur-containing heterocyclic ring group refers to a bicyclic nitrogen- and sulfur-containing heterocyclic ring group which contains a nitrogen atom and a sulfur atom as heteroatoms forming the ring, such as a benzothiazolyl group, a benzoisothiazolyl group, or a benzothiadiazolyl group.

The spiro heterocyclic ring group refers to a spiro heterocyclic ring group which contains a nitrogen atom, an oxygen atom, or a sulfur atom as a heteroatom forming the ring, such as a 2-oxa-6-azaspiro[3.3]heptyl group, a 1,4-dioxaspiro[4.5]decyl group, a 1-oxa-8-azaspiro[4.5]decyl group, or a 1-thia-8-azaspiro[4.5]decyl group.

The bridged heterocyclic ring group refers to a bridged heterocyclic ring group which contains a nitrogen atom, an oxygen atom, or a sulfur atom as a heteroatom forming the ring, such as a 3-oxa-8-azabicyclo[3.2.1]octyl group, an 8-oxa-3-azabicyclo[3.2.1]octyl group, or a quinuclidinyl group.

The acyl group refers to a formyl group, a succinyl group, a glutaryl group, a maleoyl group, a phthaloyl group, a $C_{2-6}$ alkanoyl group, a $C_{3-8}$ cycloalkylcarbonyl group, an aroyl group, or a heterocyclic carbonyl group.

The $C_{2-6}$ alkanoyl group refers to a linear or branched $C_{2-6}$ alkanoyl group such as an acetyl group, a propionyl group, a valeryl group, an isovaleryl group, or a pivaloyl group.

The $C_{3-8}$ cycloalkylcarbonyl group refers to a $C_{3-8}$ cycloalkylcarbonyl group such as a cyclopropylcarbonyl group, a cyclobutylcarbonyl group, a cyclopentylcarbonyl group, a cyclohexylcarbonyl group, or a cycloheptylcarbonyl group.

The aroyl group refers to a benzoyl group, a naphthoyl group, or the like.

The heterocyclic carbonyl group refers to a heterocyclic carbonyl group such as a pyrrolylcarbonyl group, a pyridylcarbonyl group, a furanylcarbonyl group, or a thienylcarbonyl group.

The silyl group refers to a trimethylsilyl group, a triethylsilyl group, a tributylsilyl group, or a tert-butyldimethylsilyl group.

The leaving group refers to a halogen atom, a $C_{1-6}$ alkylsulfonyloxy group, an aryloxy group, or an arylsulfonyloxy group. The $C_{1-6}$ alkylsulfonyloxy group, aryloxy group, and arylsulfonyloxy group may be substituted with one or more substituents selected from a halogen atom, a nitro group, a $C_{1-6}$ alkyl group, and a $C_{1-6}$ alkoxy group.

The hydroxyl protective group is any conventional group that can be used as a protective group for a hydroxyl group, and examples thereof include the groups described in, for example, T. W. Greene et al., Protective Groups in Organic Synthesis, 4th edition, pp. 16 to 299, 2007, John Wiley & Sons, Inc. Specific examples of the hydroxyl protective group include a $C_{1-6}$ alkyl group, a $C_{2-6}$ alkenyl group, an aryl $C_{1-6}$ alkyl group, a $C_{1-6}$ alkoxy $C_{1-6}$ alkyl group, an aryl $C_{1-6}$ alkoxy $C_{1-6}$ alkyl group, an acyl group, a $C_{1-6}$ alkoxycarbonyl group, an aryl $C_{1-6}$ alkoxycarbonyl group, a $C_{1-6}$ alkylsulfonyl group, an arylsulfonyl group, a silyl group, a tetrahydrofuranyl group, and a tetrahydropyranyl group.

The amino protective group is any conventional group that can be used as a protective group for an amino group, and examples thereof include the groups described in, for example, T. W. Greene et al., Protective Groups in Organic Synthesis, 4th edition, pp. 696 to 926, 2007, John Wiley & Sons, Inc. Specific examples of the amino protective group include an aryl $C_{1-6}$ alkyl group, a $C_{1-6}$ alkoxy $C_{1-6}$ alkyl group, an acyl group, a $C_{1-6}$ alkoxycarbonyl group, an aryl $C_{1-6}$ alkoxycarbonyl group, an aryloxycarbonyl group, a $C_{1-6}$ alkylsulfonyl group, an arylsulfonyl group, and a silyl group.

Aliphatic hydrocarbons refer to pentane, hexane, heptane, cyclohexane, methylcyclohexane, and ethylcyclohexane.

Halogenated hydrocarbons refer to dichloromethane, chloroform, and dichloroethane.

Examples of alcohols include methanol, ethanol, propanol, 2-propanol, butanol, and 2-methyl-2-propanol.

Examples of glycols include ethylene glycol, propylene glycol, and diethylene glycol.

Ethers refer to diethyl ether, diisopropyl ether, dioxane, tetrahydrofuran, anisole, ethylene glycol dimethyl ether, diethylene glycol dimethyl ether, and diethylene glycol diethyl ether.

Ketones refer to acetone, 2-butanone, 4-methyl-2-pentanone, and methyl isobutyl ketone.

Esters refer to methyl acetate, ethyl acetate, propyl acetate, and butyl acetate.

Amides refer to N,N-dimethylformamide, N,N-dimethylacetamide, and N-methylpyrrolidone.

Nitriles refer to acetonitrile and propionitrile.

Sulfoxides refer to dimethyl sulfoxide and sulfolane.

Aromatic hydrocarbons refer to benzene, toluene, and xylene.

The inorganic base refers to sodium hydroxide, potassium hydroxide, sodium methoxide, sodium ethoxide, tert-butoxy sodium, tert-butoxy potassium, sodium hydrogen carbonate, sodium carbonate, potassium carbonate, potassium phosphate, potassium acetate, cesium fluoride, cesium carbonate, or tert-butyl magnesium chloride.

The organic base refers to triethylamine, N,N-diisopropylethylamine, 1,8-diazabicyclo(5.4.0)undec-7-ene (DBU), pyridine, 4-dimethylaminopyridine, N-methylmorpholine, or imidazole.

Individual substituent groups have the following meanings.

<Substituent Group A>

A halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent group B; and a heterocyclic group which may be substituted with one or more substituents selected from Substituent group B.

<Substituent Group B>

A halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

Examples of salts of the compound represented by General Formula (1) according to the present invention include salts in basic groups such as an amino group, and salts in acidic groups such as a hydroxyl group and a carboxyl group, which are commonly known.

Examples of salts in basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Examples of the salt of an acidic group include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Among the salts mentioned above, preferred salts include pharmacologically acceptable salts.

The compound represented by General Formula (1) refers to, for example, a compound represented by General Formula (1a), a compound represented by General Formula (1b), or a compound represented by General Formula (1c).

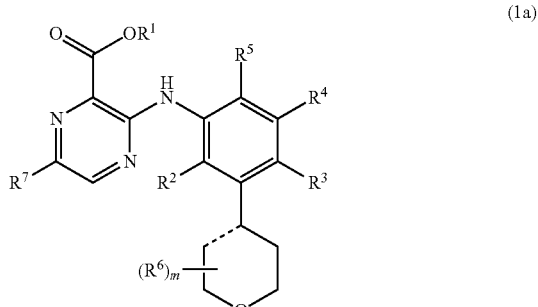

(1a)

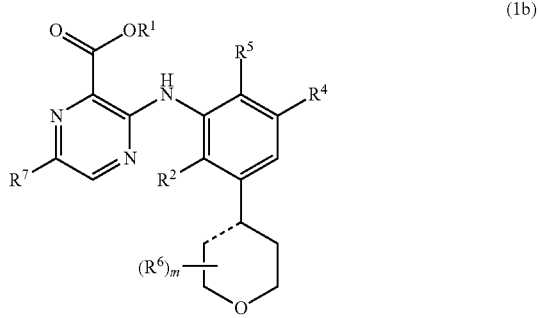

(1b)

-continued

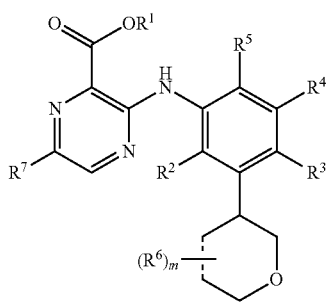

(1c)

(In the formulae, $R^1$, $R^2$, $R^3$, $R^4$, $R^5$, $R^6$, $R^7$, m, and a broken line are as defined above.)

The compound represented by General Formula (1) according to the present invention is preferably the compound represented by General Formula (1a) or the compound represented by General Formula (1b) and more preferably the compound represented by General Formula (1a).

$R^1$ $R^1$ is a hydrogen atom or a $C_{1-6}$ alkyl group.

$R^1$ is preferably a hydrogen atom or a methyl group, and more preferably a hydrogen atom.

$R^2$ $R^2$ is a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted.

$R^2$ is preferably a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^2$ is more preferably a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^2$ is still more preferably a halogen atom, a $C_{1-6}$ alkyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, or a $C_{1-6}$ alkoxy $C_{1-6}$ alkyl group which may be substituted with one or more substituents selected from Substituent group A.

$R^3$ $R^3$ is a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted.

$R^3$ is preferably a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^3$ is more preferably a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A.

$R^3$ is still more preferably a hydrogen atom or a halogen atom.

$R^4$ $R^4$ is a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted.

$R^4$ is preferably a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^4$ is more preferably a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A.

$R^4$ is still more preferably a hydrogen atom or a halogen atom.

$R^5$ $R^5$ is a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted.

$R^5$ is preferably a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^5$ is more preferably a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A.

$R^5$ is still more preferably a hydrogen atom or a halogen atom.

$R^6$ $R^6$'s are the same as or different from each other and each are a halogen atom, a $C_{1-6}$ alkyl group which may be substituted, or a $C_{1-6}$ alkoxy group which may be substituted.

$R^6$ is preferably a halogen atom, a $C_{1-6}$ alkyl group which may be substituted with one or more substituents selected from Substituent group A, or a $C_{1-6}$ alkoxy group which may be substituted with one or more substituents selected from Substituent group A.

$R^6$ is more preferably a halogen atom or a $C_{1-6}$ alkyl group which may be substituted with one or more substituents selected from Substituent group A.

$R^7$ $R^7$ is a $C_{1-6}$ alkyl group which may be substituted or a $C_{3-8}$ cycloalkyl group which may be substituted.

$R^7$ is preferably a $C_{1-6}$ alkyl group which may be substituted with one or more substituents selected from Substituent group A, or a $C_{3-8}$ cycloalkyl group which may be substituted with one or more substituents selected from Substituent group A.

$R^7$ is more preferably a $C_{1-6}$ alkyl group or a $C_{3-8}$ cycloalkyl group, still more preferably a $C_{3-8}$ cycloalkyl group, and most preferably a cyclopropyl group.

m m is an integer of 0 to 6.

m is preferably an integer of 0 to 4, more preferably an integer of 0 to 2, and still more preferably 0 or 1.

Broken Line

The broken line is a single or a double bond.

As the broken line, either a single bond or a double bond is preferable.

A halogen atom; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; an aryl group which may be substituted with one or more substituents selected from Substituent group B; and a heterocyclic group which may be substituted with one or more substituents selected from Substituent group B are preferable as Substituent group A in $R^2$, $R^3$, $R^4$, $R^5$, $R^6$, and $R^7$.

A halogen atom; a $C_{1-6}$ alkyl group; and a $C_{1-6}$ alkoxy group are more preferable as Substituent group A.

A halogen atom; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; and a $C_{1-6}$ alkoxy $C_{1-6}$ alkyl group are preferable as Substituent group B in $R^2$, $R^3$, $R^4$, $R^5$, $R^6$, and $R^7$.

A halogen atom; a $C_{1-6}$ alkyl group; a $C_{1-6}$ alkoxy group; and a $C_{1-6}$ alkoxy $C_{1-6}$ alkyl group are more preferable as Substituent group B.

In a case where isomers (for example, an optical isomer, a geometric isomer, and a tautomer) are present for the compound represented by General Formula (1), General Formula (1a), General Formula (1b), or General Formula (1c), these isomers can also be used. In addition, in a case where solvates, hydrates, and various forms of crystals are present, these solvates, hydrates, and various forms of crystals can also be used.

Next, a method for producing the compound of the present invention will be described.

The compound of the present invention is produced by combining methods known per se, and can be produced, for example, according to the following production methods.
[Production Method 1]

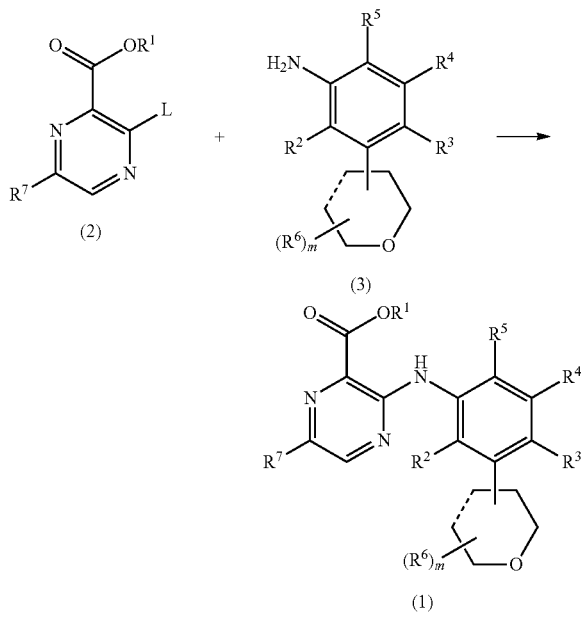

(In the formulae, L represents a leaving group; and $R^1$, $R^2$, $R^3$, $R^4$, $R^5$, $R^6$, $R^7$, m, and a broken line are as defined above.)

For example, methyl 3-bromo-6-cyclopropylpyrazine-2-carboxylate (US2011/306589A) is known as the compound represented by General Formula (2).

The compound represented by General Formula (1) can be produced by reacting the compound represented by General Formula (2) with the compound represented by General Formula (3) in the presence or absence of a base, in the presence of a palladium catalyst, and in the presence or absence of a ligand.

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be mixed and used.

Preferred solvents include ethers, esters, and aromatic hydrocarbons.

The amount of the solvent used is not particularly limited, and is preferably 1 to 100 times (v/w), more preferably 1 to 10 times (v/w), and still more preferably 1 to 5 times (v/w) with respect to the compound represented by General Formula (2).

Examples of the base optionally used in the reaction include an inorganic base and an organic base.

Preferred bases include inorganic bases such as sodium hydrogen carbonate, sodium carbonate, potassium carbonate, cesium carbonate, and potassium phosphate, and organic bases such as pyridine, 4-(dimethylamino)pyridine, triethylamine, and diisopropylethylamine.

The amount of the base used is preferably 1 to 10-fold molar amount, more preferably 1 to 5-fold molar amount, and still more preferably 1 to 2-fold molar amount with respect to the compound represented by General Formula (2).

Examples of the palladium catalyst used in the reaction include metal palladium such as palladium-carbon and palladium black; inorganic palladium salts such as palladium chloride; organic palladium salts such as palladium (II) acetate; organic palladium complexes such as tetrakis(triphenylphosphine)palladium (0), bis(triphenylphosphine)palladium (II) dichloride, 1,1'-bis(diphenylphosphino)ferrocene palladium (II) dichloride, tris(dibenzylideneacetone)dipalladium (0), and bis(di-tert)-butyl (4-dimethylaminophenyl) phosphine)palladium (II) dichloride; and polymer-immobilized organic palladium complexes such as polymer-supported bis(acetate)triphenylphosphine palladium (II) and polymer-supported di(acetate)dicyclohexylphenylphosphine palladium (II), which may be used in combination.

The amount of the palladium catalyst used is preferably 0.00001 to 1-fold molar amount and more preferably 0.001 to 0.2-fold molar amount with respect to the compound represented by General Formula (2).

Examples of the ligand optionally used in the reaction include trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite, and tributylphosphite; tricycloalkylphosphites such as tricyclohexylphosphite; triarylphosphite such as triphenylphosphite; imidazolium salts such as 1,3-bis(2,4,6-trimethylphenyl) imidazolium chloride; diketones such as acetylacetone and octafluoroacetylacetone; amines such as trimethylamine, triethylamine, tripropylamine, triisopropylamine, and tributylamine; 1,1'-bis(diphenylphosphino)ferrocene; 2,2'-bis(diphenylphosphino)-1,1'-binaphthyl; 2-dicyclohexylphosphino-2',6'-dimethoxybiphenyl; 2-dicyclohexylphosphino-2',4',6'-triisopropylbiphenyl; 2-(di-tert-butylphosphino)-2',4',6'-triisopropylbiphenyl; 2-dicyclohexylphosphino-2'-(N,N-dimethylamino)biphenyl; 4,5-bis(diphenylphosphino)-9,9-dimethylxanthene; and 2-(di-tert-butylphosphino)biphenyl, which may be used in combination.

The amount of the ligand used is 0.00001 to 1-fold molar amount and preferably 0.02 to 0.5-fold molar amount with respect to the compound represented by General Formula (2).

The amount of the compound represented by General Formula (3) used is preferably 1 to 50-fold molar amount and more preferably 1 to 2-fold molar amount with respect to the compound represented by General Formula (2).

The reaction may be carried out preferably at 40° C. to 170° C. for 1 minute to 24 hours under an atmosphere of an inert gas (for example, nitrogen or argon).

The reaction may be carried out under microwave irradiation.

[Production Method 1]

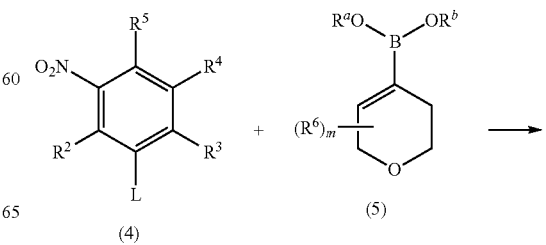

-continued $$\text{(6)}$$

(In the formulae, $R^a$ and $R^b$ are the same as or different from each other and each represent a hydrogen atom or a $C_{1-6}$ alkyl group, or $R^a$ and $R^b$ together form an ethylene group which may be substituted with one or more $C_{1-6}$ alkyl groups; and $R^2$, $R^3$, $R^4$, $R^5$, $R^6$, m, and L are as defined above.)

For example, 1-bromo-2-fluoro-3-nitrobenzene and 1-bromo-2,5-difluoro-3-nitrobenzene are known as the compound represented by General Formula (4).

For example, 3,6-dihydro-2H-pyran-4-boronic acid pinacol ester is known as the compound represented by General Formula (5).

In addition, the compound represented by General Formula (5) can be produced from the corresponding halogeno form by a method known per se.

The compound represented by General Formula (6) can be produced by reacting the compound represented by General Formula (4) with the compound represented by General Formula (5) in the presence or absence of a base, in the presence of a palladium catalyst, and in the presence or absence of a ligand, according to the production method 1.

[Production Method B]

$$\text{(6)} \longrightarrow \text{(3a)}$$

(In the formulae, $R^2$, $R^3$, $R^4$, $R^5$, $R^6$, and m are as defined above).

The compound represented by General Formula (3a) can be produced by reducing the compound represented by General Formula (6).

The reaction may be carried out by the method described in Comprehensive Organic Transformations, Richard C. Larock et al., 2nd Edition, pp. 823 to 827, 1999, John Wiley & Sons, Inc.) or a method similar thereto.

Specific examples of such a method include a catalytic hydrogenation reaction using a metal catalyst and a reduction reaction using a metal such as iron or zinc in the presence or absence of an acid and in the presence or absence of a salt.

<<Contact Hydrogenation Reaction Using Metal Catalyst>>

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be mixed and used.

Preferred solvents include ethers, esters, alcohols, and amides.

The amount of the solvent used is not particularly limited, and is preferably 1 to 100 times (v/w), more preferably 1 to 10 times (v/w), and still more preferably 1 to 5 times (v/w) with respect to the compound represented by General Formula (6).

Examples of the metal catalyst used in the reaction include metal palladium such as palladium-carbon and palladium black; palladium salts such as palladium oxide and palladium hydroxide; and nickel metals such as Raney nickel and platinum salts such as platinum oxide.

The amount of the metal catalyst used is preferably 0.001 to 5-fold amount (W/W) and more preferably 0.01 to 1-fold amount (W/W) with respect to the compound represented by General Formula (6).

Examples of the reducing agent include hydrogen; formic acid; formates such as sodium formate, ammonium formate, and triethylammonium formate; and cyclohexene and cyclohexadiene.

The amount of the reducing agent used is preferably 2 to 100-fold molar amount and more preferably 2 to 10-fold molar amount with respect to the compound represented by General Formula (6).

The reaction may be carried out at 0° C. to 200° C., preferably 0° C. to 100° C. for 1 minute to 24 hours.

<<Reduction Reaction Using Metal>>>

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be mixed and used.

Preferred solvents include alcohols and water.

The amount of the solvent used is not particularly limited, and is preferably 1 to 100 times (v/w), more preferably 1 to 10 times (v/w), and still more preferably 1 to 5 times (v/w) with respect to the compound represented by General Formula (6).

Examples of the metal used in the reaction include iron, zinc, tin, and tin (II) chloride.

The amount of the metal used is preferably 1 to 50-fold molar amount and more preferably 1 to 10-fold molar amount with respect to the compound represented by General Formula (6).

Examples of the acid used in the reaction include hydrogen chloride, hydrogen bromide, and acetic acid.

The amount of the acid used is preferably 0.001 to 100-fold amount (W/V) and more preferably 0.01 to 20-fold amount (W/V) with respect to the compound represented by General Formula (6).

Examples of the salt used in the reaction include ammonium chloride.

The amount of the salt used is preferably 0.01 to 10-fold molar amount and more preferably 0.1 to 5-fold molar amount with respect to the compound represented by General Formula (6).

The reaction may be carried out at 0° C. to 200° C., preferably 0° C. to 100° C. for 1 minute to 24 hours.

[Production Method C]

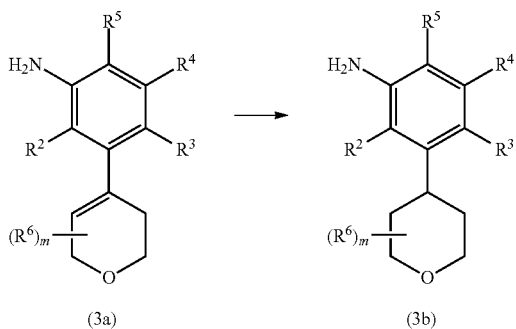

(In the formulae, $R^2$, $R^3$, $R^4$, $R^5$, $R^6$, and m are as defined above).

The compound represented by General Formula (3b) can be produced by reducing the compound represented by General Formula (3a), according to the production method B.

[Production Method D]

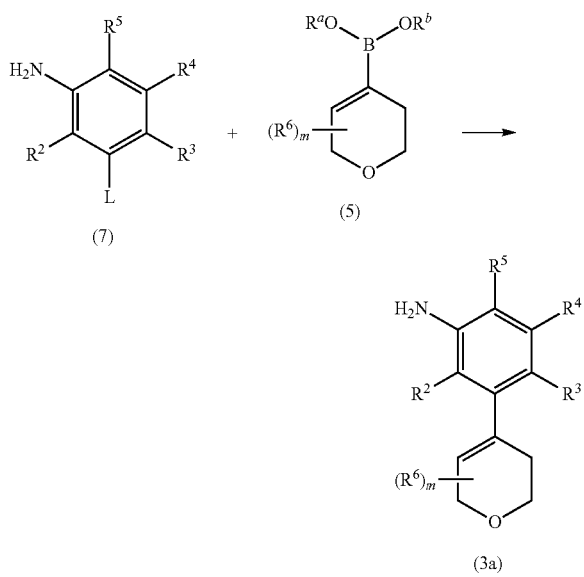

(In the formulae, $R^2$, $R^3$, $R^4$, $R^5$, $R^6$, $R^a$, $R^b$, m, and L are as defined above.)

For example, 3-bromo-2-methoxyaniline and 3-bromo-2-methylaniline are known as the compound represented by General Formula (7).

The compound represented by General Formula (3a) can be produced by reacting the compound represented by General Formula (7) with the compound represented by General Formula (5) in the presence or absence of a base, in the presence of a palladium catalyst, and in the presence or absence of a ligand, according to the production method 1.

Among the compounds used in the above-mentioned production methods, a compound that can take the form of a salt can also be used as a salt. Examples of the salt include salts similar to those of the compound represented by General Formula (1).

In a case where isomers (for example, an optical isomer, a geometric isomer, and a tautomer) are present for the compounds used in the above-mentioned production methods, these isomers can also be used. In addition, in a case where solvates, hydrates, and various forms of crystals are present, these solvates, hydrates, and various forms of crystals can also be used.

In addition, among the compounds used in the above-mentioned production methods, in a case of a compound having a group that can be protected, for example, an amino group, a hydroxyl group, or a carboxyl group, such a group can be protected with a normal protective group in advance, and after the reaction, the protective group can be removed by a method known per se.

In a case where the compound of the present invention is used as a pharmaceutical composition, a pharmaceutical aid such as an excipient, a carrier, or a diluent commonly used for formulation may be appropriately mixed. The pharmaceutical aid can be administered orally or parenterally in the form of a tablet, a capsule, a powder, a syrup, a granule, a pill, a suspension, an emulsion, a solution, a powdery preparation, a suppository, an eye drop, a nasal drop, an ear drop, a patch, an ointment, an injection, or the like according to a conventional method. In addition, a method of administration, a given dose, and a frequency of administration can be appropriately selected according to the age, weight, and condition of the patient. Usually, for an adult, 0.01 to 1,000 mg/kg/day may be administered singly or in several divided doses by oral or parenteral administration (for example, injection, drip infusion, or rectal administration).

The compound of the present invention or a salt thereof has an excellent anti-tumor activity and can be used for the treatment of a tumor.

The treatment refers to preventing, treating, or the like of a variety of diseases.

The treatment agent refers to a substance which is provided for the purpose of preventing or treating a variety of diseases.

The preventing refers to inhibition of disease onset, reduction of disease onset risk, delay of disease onset, or the like.

The treating refers to improvement of, inhibition of progression of, or the like of a target disease or condition.

The tumor refers to a benign tumor or a malignant tumor.

The benign tumor refers to a tumor in which a tumor cell and a sequence thereof have a morphology close to that of a normal cell from which such a tumor cell is derived and which is not invasive or metastatic.

The malignant tumor refers to a tumor in which the morphology and sequence of a tumor cell are different from those of a normal cell from which such a tumor cell is derived and which is invasive or metastatic.

The anti-tumor agent of the present invention is preferably used as an antineoplastic agent, and is preferably used as a cancer treatment agent (preferably a blood cancer treatment agent).

Examples of the blood cancer include acute lymphocytic leukemia (ALL), acute myelogenous leukemia (AML), acute promyelogenous leukemia (APL), chronic lymphocytic leukemia (CLL), chronic myelogenous leukemia (CML), chronic neutrophilic leukemia (CNL), acute undifferentiated leukemia (AUL), anaplastic large cell lymphoma (ALCL), prolymphocytic leukemia (PLL), juvenile myelomonocytic leukemia (JMML), adult T-cell leukemia (ATL), myelodysplastic syndrome (MDS), myeloproliferative disease (MPD), lymphoblastic lymphoma (LBL), and adult T-cell leukemia/lymphoma (ATLL).

The compound of the present invention or a salt thereof can also be used as a dihydroorotate dehydrogenase inhibitor.

The compound of the present invention or a salt thereof can be used as a treatment agent (for example, an anti-tumor agent or an antirheumatic agent) for a disease associated with dihydroorotate dehydrogenase such as tumor or rheumatism.

The dihydroorotate dehydrogenase inhibitor of the present invention can be used in the same manner as in the above-mentioned pharmaceutical composition and anti-tumor agent of the present invention.

EXAMPLES

Hereinafter, the present invention will be described with reference to Reference Examples and Examples, but the present invention is not limited thereto.

Unless otherwise specified, purification by column chromatography was carried out using an automated purification apparatus ISOLERA (manufactured by Biotage AB) or a medium-pressure liquid chromatograph YFLC-Wprep2XY.N (manufactured by Yamazen Corporation).

Unless otherwise specified, SNAPKP-Sil Cartridge (manufactured by Biotage AB), HI-FLASH COLUMN W001, W002, W003, W004, or W005 (manufactured by Yamazen Corporation), and CHROMATOREX Q-PACK Cartridge (manufactured by Fuji Silysia Chemical Ltd.) were used as carriers in silica gel column chromatography.

In preparative thin layer chromatography, PLC glass plate silica gel $F_{60}$ (manufactured by Merck & Co., Inc.) was used.

The mixing ratio in the eluent was a volume ratio. For example, "hexane:ethyl acetate gradient elution=50:50 to 0:100" means that an eluent of 50% hexane/50% ethyl acetate was finally changed to an eluent of 0% hexane/100% ethyl acetate.

Initiator Sixty (manufactured by Biotage AB) was used as a microwave reactor.

The NMR spectrum was measured using Bruker AV300 (manufactured by Bruker Corporation, 300 MHz), Bruker AV400 (manufactured by Bruker Corporation, 400 MHz), and Bruker Fourier-400 (manufactured by Bruker Corporation, 400 MHz) and using tetramethylsilane as an internal reference. All δ values are shown in ppm.

The MS spectrum was measured using ACQUITY SQD LC/MS System (manufactured by Waters Corporation, ionization method: Electro Spray Ionization (ESI) method), Micromass ZQ2000 LCMS System (manufactured by Waters Corporation, ionization method: ESI), Model M-8000 (manufactured by Hitachi, Ltd., ionization method: ESI method), or LCMS-2010EV (manufactured by Shimadzu Corporation, ionization method: method of carrying out ESI and Atmospheric Pressure Chemical Ionization (APCI) at the same time).

The retention time (RT) was measured using SQD (manufactured by Waters Corporation) and 2695 Separations Module (manufactured by Waters Corporation), and was shown in minutes (min).

The measurement was carried out under the following conditions.

Method A
Column: BEHC 18 1.7 μm, 2.1×30 mm (manufactured by Waters Corporation)
Solvent: liquid A: 0.1% formic acid-water
liquid B: 0.1% formic acid-acetonitrile
Gradient cycle: 0.00 min (liquid A/liquid B=95/5), 2.00 min (liquid A/liquid B=5/95), 3.00 min (liquid A/liquid B=5/95), 3.01 min (liquid A/liquid B=100/0), 3.80 min (liquid A/liquid B=100/0)
Flow rate: 0.5 mL/min
Column temperature: room temperature
Detection wavelength: 254 nm Method B
Column: XBridge C18 5 μm, 3.0×50 mm (manufactured by Waters Corporation)
Solvent: liquid A: 0.05% trifluoroacetic acid-water
liquid B: 0.05% trifluoroacetic acid-acetonitrile
Gradient cycle: 0.00 min (liquid A/liquid B=90/10), 1.00 min (liquid A/liquid B=90/10), 1.50 min (liquid A/liquid B=70/30), 4.50 min (liquid A)/liquid B=30/70), 5.00 min (liquid A/liquid B=10/90), 6.00 min (liquid A/liquid B=10/90), 6.20 min (liquid A/liquid B=90/10), 7.00 min (liquid A/liquid B=90/10)
Flow rate: 1.27 mL/min
Column temperature: 30° C.
Detection wavelength: 254 nm Abbreviations in Examples have the following meanings.
RT (min): retention time (minutes)

Reference Example 1

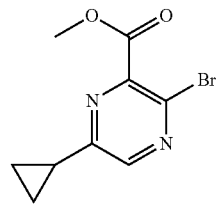

The following compounds were obtained according to the method described in US2011/306589A.

Methyl 3-bromo-6-cyclopropylpyrazine-2-carboxylate

LCMS (Method A)
MS (ESI m/z): 258 (M+H)
RT (min): 1.31

Reference Example 2

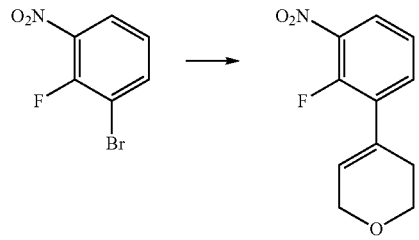 [SMILES: O=[N+]([O-])c1cccc(Br)c1F ; O=[N+]([O-])c1cccc(C2=CCOCC2)c1F]

A mixture of 1-bromo-2-fluoro-3-nitrobenzene (1.0 g), 3,6-dihydro-2H-pyran-4-boronic acid pinacol ester (1.1 g), bis(di-tert-butyl(4-dimethylaminophenyl)phosphine)dichloropalladium (II) (0.16 g), potassium phosphate (1.9 g), 1,2-dimethoxyethane (10 mL), and water (2.0 mL) was irradiated with microwaves (microwave reactor, 110° C., 30 minutes, 2.45 GHz, 0 to 240 W). An aqueous sodium chloride solution was added to the reaction liquid which was then extracted twice with ethyl acetate. The solvent of the organic layer was distilled off under reduced pressure, and the obtained residue was purified by silica gel column chromatography to obtain 4-(2-fluoro-3-nitrophenyl)-3,6-dihydro-2H-pyran (0.95 g) as a brown solid.

1H-NMR (CDCl$_3$) δ: 7.93-7.88 (m, 1H), 7.56-7.51 (m, 1H), 7.29-7.22 (m, 1H), 6.11-6.07 (m, 1H), 4.37-4.32 (m, 2H), 3.94 (t, 2H, J=5.6 Hz), 2.56-2.48 (m, 2H).

Reference Example 3

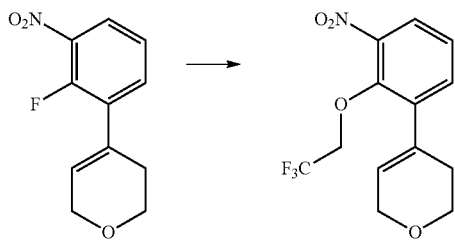 [SMILES: O=[N+]([O-])c1cccc(C2=CCOCC2)c1F ; O=[N+]([O-])c1cccc(C2=CCOCC2)c1OCC(F)(F)F]

60% sodium hydride (22 mg) was added to a mixture of 4-(2-fluoro-3-nitrophenyl)-3,6-dihydro-2H-pyran (60 mg), 2,2,2-trifluoroethanol (34 μL), and N,N-dimethylformamide (0.50 mL) under ice cooling, and the mixture was stirred at room temperature for 5 minutes. Water was added to the reaction liquid which was then extracted twice with ethyl acetate. The solvent of the organic layer was distilled off under reduced pressure, toluene was added, and the solvent was then distilled off under reduced pressure. Toluene was further added and the solvent was distilled off under reduced pressure to obtain 4-(3-nitro-2-(2,2,2-trifluoroethoxy)phenyl)-3,6-dihydro-2H-pyran (80 mg) as a brown oil.

1H-NMR (CDCl3) δ: 7.76 (dd, 1H, J=7.9, 2.0 Hz), 7.45 (dd, 1H, J=7.6, 1.7 Hz), 7.29 (dd, 1H, J=7.9, 7.6 Hz), 6.04-6.01 (m, 1H), 4.36 (q, 2H, J=8.3 Hz), 4.34-4.30 (m, 2H), 3.93 (t, 2H, J=5.3 Hz), 2.53-2.45 (m, 2H).

Reference Example 4

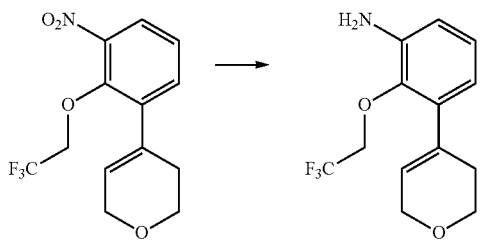 [SMILES: O=[N+]([O-])c1cccc(C2=CCOCC2)c1OCC(F)(F)F ; Nc1cccc(C2=CCOCC2)c1OCC(F)(F)F]

A mixture of 4-(3-nitro-2-(2,2,2-trifluoroethoxy)phenyl)-3,6-dihydro-2H-pyran (80 mg), ammonium chloride (29 mg), isopropyl alcohol (1.0 mL), and water (0.50 mL) was stirred at 90° C., and iron (150 mg) was added thereto, followed by stirring for 40 minutes. After cooling to room temperature, the insoluble matter was removed, and an aqueous sodium chloride solution was added, followed by extraction twice with ethyl acetate. The solvent of the organic layer was distilled off under reduced pressure to obtain 3-(3,6-dihydro-2H-pyran-4-yl)-2-(2,2,2-trifluoroethoxy)aniline (68 mg) as a brown oil.

LCMS (Method A)
MS (ESI m/z): 274 (M+H)
RT (min): 1.33

Reference Example 5

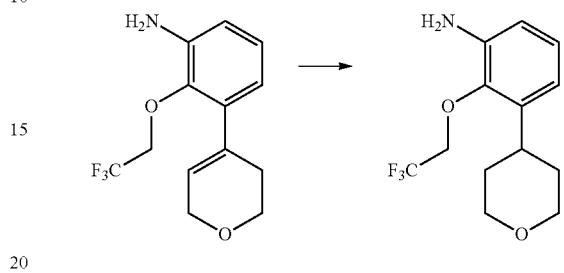

A mixture of 3-(3,6-dihydro-2H-pyran-4-yl)-2-(2,2,2-trifluoroethoxy)aniline (50 mg), 10% palladium on carbon (29 mg), ammonium formate (0.46 g), and methanol (2.0 mL) was stirred with heating under reflux for 1.5 hours. 10% palladium on carbon (20 mg) and ammonium formate (0.23 g) were added to the mixture which was then stirred for 1.5 hours. After cooling to room temperature, solid matter was removed by filtration through Celite. Water was added to the filtrate which was then extracted twice with ethyl acetate. The solvent of the organic layer was distilled off under reduced pressure to obtain 3-(tetrahydro-2H-pyran-4-yl)-2-(2,2,2-trifluoroethoxy)aniline (32 mg) as a yellow oil.

LCMS (Method A)
MS (ESI m/z): 276 (M+H)
RT (min): 1.33

Reference Example 6

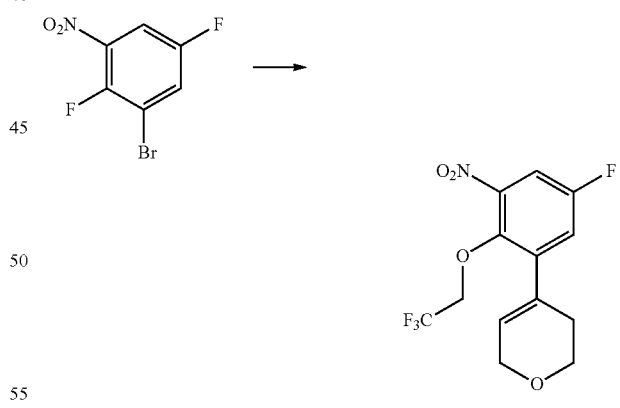

60% sodium hydride (0.12 g) was added to a mixture of 1-bromo-2,5-difluoro-3-nitrobenzene (0.60 g), 2,2,2-trifluoroethanol (0.24 mL), and N,N-dimethylformamide (6.0 mL) under ice cooling, and the mixture was stirred for 1 hour. Water was added to the reaction liquid which was then extracted with ethyl acetate. The organic layer was washed with water and a saturated aqueous sodium chloride solution and dried over magnesium sulfate. The solvent was distilled off under reduced pressure to obtain a residue. A mixture of the obtained residue (0.80 g), 3,6-dihydro-2H-pyran-4-boronic acid pinacol ester (0.61 g), [1,1'-bis(diphenylphosphino)ferrocene]palladium (II) dichloride dichloromethane adduct (0.10 g), sodium carbonate (0.80 g), 1,2-dimethoxyethane (9.6 mL), and water (3.2 mL) was stirred with heating under reflux for 1 hour and 15 minutes. After cooling to room temperature, water was added to the reaction liquid which was then extracted with ethyl acetate. The organic layer was washed with a saturated aqueous sodium chloride solution and dried over magnesium sulfate. The solvent was distilled off under reduced pressure, and the obtained residue was purified by silica gel column chromatography (hexane: ethyl acetate gradient elution=90:10 to 80:20) to obtain 4-(5-fluoro-3-nitro-2-(2,2,2-trifluoroethoxy)phenyl)-3,6-dihydro-2H-pyran (0.35 g) as a light brown solid.

1H-NMR (CDCl3) δ: 7.50 (dd, 1H, J=7.3, 3.3 Hz), 7.20 (dd, 1H, J=7.9, 3.3 Hz), 6.10-6.06 (m, 1H), 4.37-4.29 (m, 4H), 3.93 (t, 2H, J=5.3 Hz), 2.51-2.44 (m, 2H).

Reference Example 7

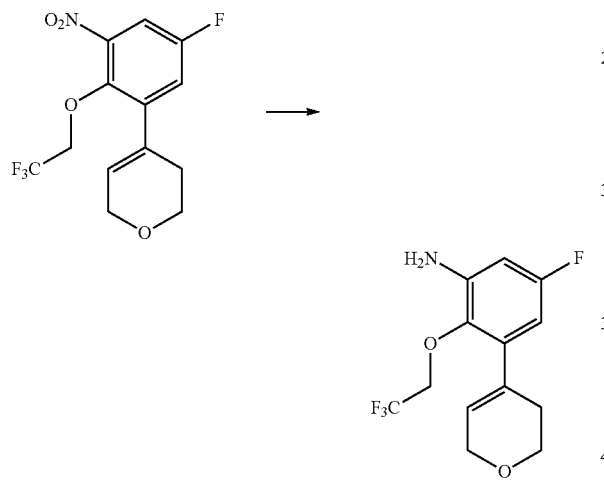

3-(3,6-dihydro-2H-pyran-4-yl)-5-fluoro-2-(2,2,2-trifluoroethoxy)aniline (0.22 g) was obtained as a white solid from 4-(5-fluoro-3-nitro-2-(2,2,2-trifluoroethoxy)phenyl)-3,6-dihydro-2H-pyran (0.35 g) in the same manner as in Reference Example 4.

LCMS (Method A)
MS (ESI m/z): 292 (M+H)
RT (min): 1.44

Reference Example 8

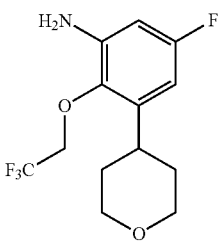

5-fluoro-3-(tetrahydro-2H-pyran-4-yl)-2-(2,2,2-trifluoroethoxy)aniline (32 mg) was obtained as a white solid from 3-(3,6-dihydro-2H-pyran-4-yl)-5-fluoro-2-(2,2,2-trifluoroethoxy)aniline (0.15 g) in the same manner as in Reference Example 5.

LCMS (Method A)
MS (ESI m/z): 294 (M+H)
RT (min): 1.41

Reference Example 9

(S)-4-(3-nitro-2-((1,1,1-trifluoropropan-2-yl)oxy)phenyl)-3,6-dihydro-2H-pyran (100 mg) was obtained as a yellow oil from 4-(2-fluoro-3-nitrophenyl)-3,6-dihydro-2H-pyran (70 mg) and (S)-1,1,1-trifluoro-2-propanol (43 mg) in the same manner as in Reference Example 3.

1H-NMR (CDCl3) δ: 7.73 (dd, 1H, J=7.9, 1.3 Hz), 7.42 (dd, 1H, J=7.6, 1.7 Hz), 7.24 (dd, 1H, J=7.9, 7.6 Hz), 6.00-5.96 (m, 1H), 4.56-4.42 (m, 1H), 4.35-4.29 (m, 2H), 3.92 (t, 2H, J=5.3 Hz), 2.61-2.37 (m, 2H), 1.42 (d, 3H, J=6.6 Hz).

Reference Example 10

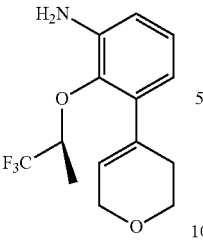

(S)-3-(3,6-dihydro-2H-pyran-4-yl)-2-((1,1,1-trifluoropropan-2-yl)oxy)aniline (80 mg) was obtained as a colorless oil from (S)-4-(3-nitro-2-((1,1,1-trifluoropropan-2-yl)oxy)phenyl)-3,6-dihydro-2H-pyran (100 mg) in the same manner as in Reference Example 4.

LCMS (Method A)
MS (ESI m/z): 288 (M+H)
RT (min): 1.43

Reference Example 11

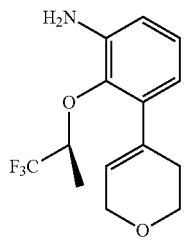 

(S)-3-(tetrahydro-2H-pyran-4-yl)-2-((1,1,1-trifluoropropan-2-yl)oxy)aniline (21 mg) was obtained as a white solid from (S)-3-(3,6-dihydro-2H-pyran-4-yl)-2-((1,1,1-trifluoropropan-2-yl)oxy)aniline (40 mg) in the same manner as in Reference Example 5.

LCMS (Method A)
MS (ESI m/z): 290 (M+H)
RT (min): 1.42

Reference Example 12

 

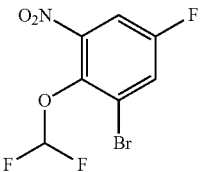

Trifluoroacetic anhydride (1.5 mL) was added to a mixture of 2-bromo-4-fluorophenol (2.0 g), copper nitrate trihydrate (1.3 g), and acetonitrile (60 mL) under ice cooling, followed by stirring for 50 minutes. After adding a mixed solution of 50% aqueous potassium hydroxide solution (17 mL) and water (23 mL) and water (20 mL), diethyl (bromodifluoromethyl)phosphonate (3.7 mL) was added dropwise over 10 minutes, followed by stirring at room temperature for 1 hour and 15 minutes. Diisopropyl ether and water were added to the reaction liquid. The organic layer was separated, washed with water and a saturated aqueous sodium chloride solution, and dried over magnesium sulfate. The solvent was distilled off under reduced pressure, and the obtained residue was purified by silica gel column chromatography (hexane:ethyl acetate gradient elution=100:00 to 80:20) to obtain 1-bromo-2-(difluoromethoxy)-5-fluoro-3-nitrobenzene (3.2 g) as a brown oil.

1H-NMR (CDCl3) δ: 7.68-7.62 (m, 2H), 6.66 (t, 1H, J=85.7 Hz).

Reference Example 13

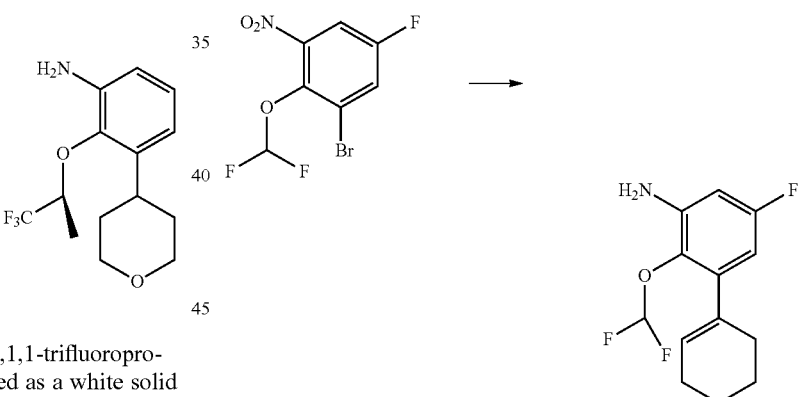

(A) A mixture of 1-bromo-2-(difluoromethoxy)-5-fluoro-3-nitrobenzene (0.80 g), 3,6-dihydro-2H-pyran-4-boronic acid pinacol ester (0.93 g), bis(di-tert-butyl(4-dimethylaminophenyl)phosphine)dichloropalladium (II) (0.10 g), potassium phosphate (1.2 g), 1,2-dimethoxyethane (12 mL), and water (4.0 mL) was stirred at 100° C. for 1 hour under a nitrogen atmosphere. After cooling to room temperature, an aqueous sodium chloride solution was added to the reaction liquid which was then extracted with ethyl acetate. The organic layer was washed with a saturated aqueous sodium chloride solution and dried over magnesium sulfate. The solvent was distilled off under reduced pressure to obtain a residue.

(B) A mixture of iron (0.78 g), ammonium chloride (0.15 g), isopropyl alcohol (16 mL), and water (8.0 mL) was stirred at 50° C. for 30 minutes. After cooling to room temperature, a solution of the residue obtained in (A) in isopropyl alcohol (8.0 mL) was added thereto, followed by stirring at 90° C. for 1 hour and 15 minutes. The mixture was cooled to room temperature, and ethyl acetate, sodium bicarbonate water, and Celite were added thereto, followed by stirring at room temperature and filtration through Celite. The organic layer was separated, washed with an aqueous sodium chloride solution, and dried over magnesium sulfate. The solvent was distilled off under reduced pressure, and the obtained residue was purified by silica gel column chromatography (hexane:ethyl acetate gradient elution=90:10 to 80:20) to obtain 2-(difluoromethoxy)-3-(3,6-dihydro-2H-pyran-4-yl)-5-fluoroaniline (0.41 g) as a white solid.

MS (ESI m/z): 260 (M+H)
RT (min): 1.31

Reference Example 14

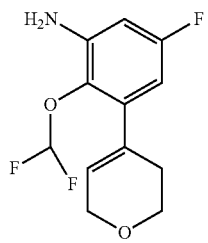

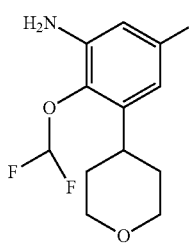

2-(difluoromethoxy)-5-fluoro-3-(tetrahydro-2H-pyran-4-yl)aniline (0.16 g) was obtained from 2-(difluoromethoxy)-3-(3,6-dihydro-2H-pyran-4-yl)-5-fluoroaniline (0.27 g) in the same manner as in Reference Example 5.

LCMS (Method A)
MS (ESI m/z): 262 (M+H)
RT (min): 1.28

Reference Example 15

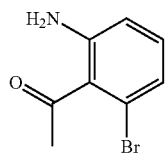

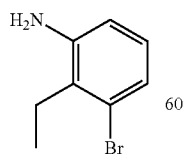

A mixture of 1-(2-amino-6-bromophenyl)ethan-1-one (0.15 g), hydrazine monohydrate (0.18 g), and diethylene glycol (3.0 mL) was stirred at 100° C. for 2 hours. After cooling to room temperature, a 50% aqueous potassium hydroxide solution (0.16 g) was added thereto, followed by stirring at 180° C. for 3 hours. After cooling to room temperature, water was added to the reaction liquid which was then extracted with toluene. The organic layer was washed twice with water, washed with an aqueous sodium chloride solution, and dried over magnesium sulfate. The solvent was distilled off under reduced pressure, and the obtained residue was purified by silica gel column chromatography (hexane:ethyl acetate gradient elution=100:0 to 80:20) to obtain 3-bromo-2-ethylaniline (0.12 g) as a colorless oil.

LCMS (Method A)
MS (ESI m/z): 200 (M+H)
RT (min): 1.39

Reference Example 16

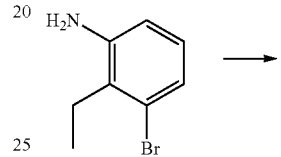

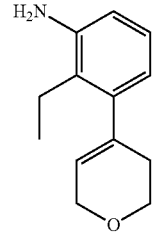

3-(3,6-dihydro-2H-pyran-4-yl)-2-ethylaniline (41 mg) was obtained as a yellow solid from 3-bromo-2-ethylaniline (0.12 g) in the same manner as in Reference Example 2.

LCMS (Method A)
MS (ESI m/z): 204 (M+H)
RT (min): 0.87

Reference Example 17

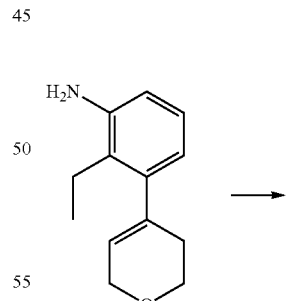

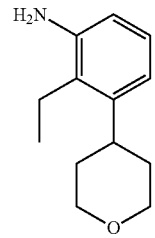

2-ethyl-3-(tetrahydro-2H-pyran-4-yl)aniline (19 mg) was obtained from 3-(3,6-dihydro-2H-pyran-4-yl)-2-ethylaniline (21 mg) in the same manner as in Reference Example 5.
LCMS (Method A)
MS (ESI m/z): 206 (M+H)
RT (min): 0.72

Reference Example 18

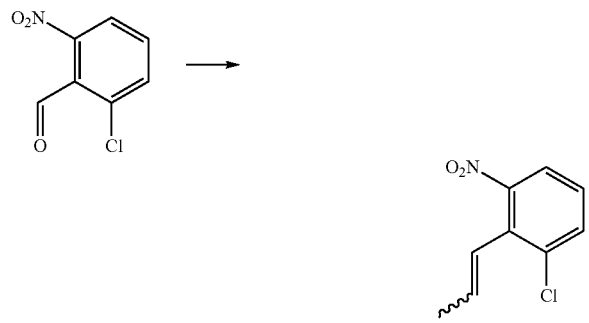

A mixture of 2-chloro-6-nitrobenzaldehyde (1.0 g), potassium carbonate (1.5 g), ethyltriphenylphosphonium iodide (2.7 g), and tetrahydrofuran (10 mL) was stirred with heating under reflux for 4.5 hours. Isopropyl alcohol (10 mL) was added to the mixture which was then stirred with heating under reflux for 5 hours. After cooling to room temperature, an aqueous ammonium chloride solution was added to the reaction liquid which was then extracted with toluene. The organic layer was washed with a 10% aqueous methanol solution, washed with a saturated aqueous sodium chloride solution, and dried over magnesium sulfate. The solvent was distilled off under reduced pressure, and the obtained residue was purified by silica gel column chromatography (hexane:ethyl acetate gradient elution=100:0 to 90:10) to obtain 1-chloro-3-nitro-2-(propa-1-en-1-yl)benzene (0.74 g) as a yellow oil.

1H-NMR (CDCl3) δ: 8.31-7.08 (m, 3H), 6.48-6.42 (m, 1H), 6.05-5.85 (m, 1H), 1.91-1.43 (m, 3H).

Reference Example 19

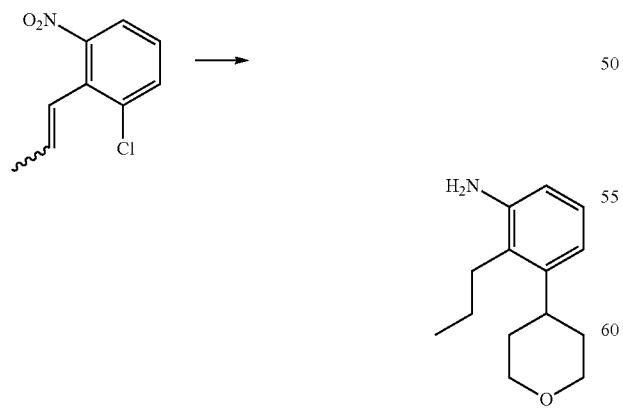

A mixture of 1-chloro-3-nitro-2-(propa-1-en-1-yl)benzene (0.74 g), 3,6-dihydro-2H-pyran-4-boronic acid pinacol ester (0.99 g), bis(di-tert-butyl(4-dimethylaminophenyl)phosphine)dichloropalladium (II) (0.27 g), potassium phosphate (2.0 g), 1,2-dimethoxyethane (11 mL), and water (3.7 mL) was irradiated with microwaves (microwave reactor, 100° C., 1 hour, 2.45 GHz, 0 to 240 W). An aqueous sodium chloride solution was added to the reaction liquid which was then extracted with ethyl acetate. The organic layer was dried over magnesium sulfate. The solvent was distilled off under reduced pressure, and the obtained residue was purified by silica gel column chromatography (hexane:ethyl acetate gradient elution=100:0 to 80:20) to obtain a brown oil (0.61 g). A mixture of the obtained oil (0.30 g), 10% palladium on carbon (0.30 g), ammonium formate (3.9 g), and methanol (24 mL) was stirred with heating under reflux for 2 hours under a nitrogen atmosphere. After cooling to room temperature, water and ethyl acetate were added to the reaction liquid, and solid matter was removed by filtration through Celite. The organic layer was separated, washed with a saturated aqueous sodium chloride solution, and then dried over magnesium sulfate. The solvent was distilled off under reduced pressure, and the obtained residue was purified by silica gel column chromatography (hexane:ethyl acetate gradient elution=100:0 to 80:20) to obtain 2-propyl-3-(tetrahydro-2H-pyran-4-yl)aniline (0.24 g) as a white solid.
LCMS (Method A)
MS (ESI m/z): 220 (M+H)
RT (min): 0.89

Reference Example 20

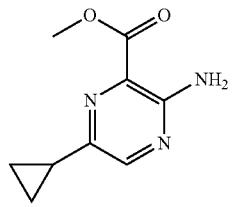

The following compounds were obtained according to the method described in US2011/306589A.
Methyl 3-amino-6-cyclopropylpyrazine-2-carboxylate
LCMS (Method A)
MS (ESI m/z): 194 (M+H)
RT (min): 0.92

Reference Example 21

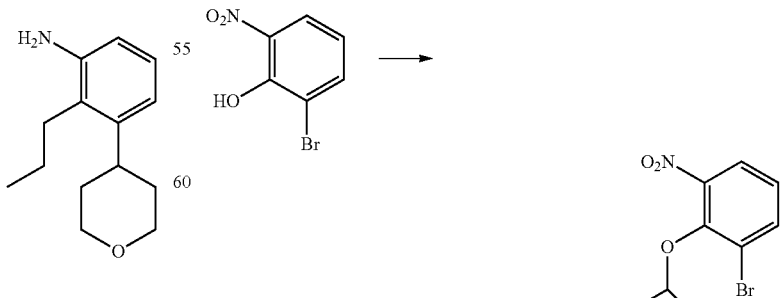

Diethyl (bromodifluoromethyl)phosphonate (2.7 g) was added dropwise to a mixture of 2-bromo-6-nitrophenol (2.0 g), acetonitrile (30 mL), water (10 mL), and a 50% aqueous potassium hydroxide solution (10 g), followed by stirring at room temperature for 30 minutes. Diethyl (bromodifluoromethyl)phosphonate (0.49 g) was added to the mixture which was then stirred at room temperature for 10 minutes. Diethyl (bromodifluoromethyl)phosphonate (0.49 g) was added to the mixture which was then stirred at room temperature for 10 minutes. Water was added to the reaction liquid which was then extracted twice with toluene. The solvent was distilled off under reduced pressure to obtain 1-bromo-2-(difluoromethoxy)-3-nitrobenzene (2.9 g) as a brown oil.

1H-NMR (DMSO-D6) δ: 8.16 (dd, 1H, J=8.0, 1.3 Hz), 8.11 (dd, 1H, J=8.0, 1.3 Hz), 7.54 (t, 1H, J=7.9 Hz), 7.26 (t, 1H, J=71.6 Hz).

Reference Example 22

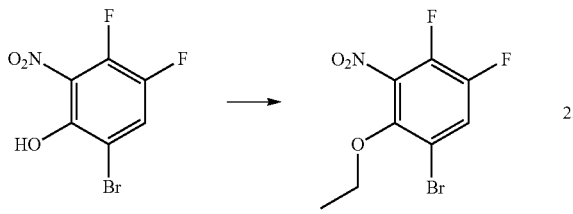

A mixture of 6-bromo-3,4-difluoro-2-nitrophenol (0.10 g), potassium carbonate (0.16 g), iodoethane (64 μL), and N,N-dimethylformamide (2.0 mL) was irradiated with microwaves (microwave reactor, 90° C., 1 hour, 2.45 GHz, 0 to 240 W). Iodoethane (64 μL) was added to the mixture which was then irradiated with microwaves (microwave reactor, 90° C., 1 hour, 2.45 GHz, 0 to 240 W). The reaction liquid was collected by filtration, and the filtrate was distilled off under reduced pressure. The obtained residue was purified by silica gel column chromatography to obtain 1-bromo-2-ethoxy-4,5-difluoro-3-nitrobenzene (87 mg) as a yellow oil.

1H-NMR (CDCl3) δ: 7.79 (dd, 1H, J=9.2, 7.9 Hz), 4.22 (q, 2H, J=7.0 Hz), 1.50 (t, 3H, J=7.0 Hz).

Reference Example 23

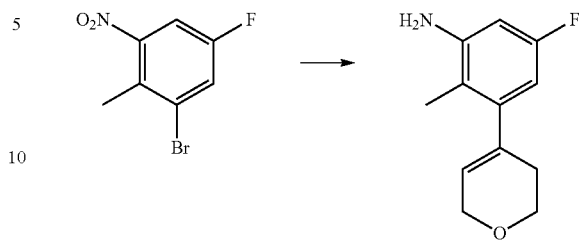

3-(3,6-dihydro-2H-pyran-4-yl)-5-fluoro-2-methylaniline was obtained in the same manner as in Reference Example 13.

LCMS (Method A)
MS (ESI m/z): 208 (M+H)
RT (min): 1.12

Reference Example 24

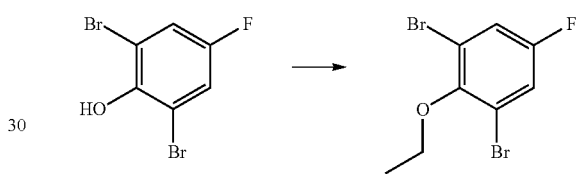

1,3-dibromo-2-ethoxy-5-fluorobenzene was synthesized in the same manner as in Reference Example 22.

1H-NMR (CDCl3) δ: 7.27 (d, 2H, J=7.9 Hz), 4.05 (q, 2H, J=7.0 Hz), 1.48 (t, 3H, J=7.3 Hz).

Reference Example 25

A compound C was synthesized from compounds A and B in the same manner as in Reference Example 3. Reference Example 25-5 was carried out by changing the reaction temperature to 70° C.

TABLE 1

| Reference Example No. | A | B | C | NMR |
|---|---|---|---|---|
| 25-1 | (structure with OH, F, F) | (O2N, F, dihydropyran structure) | (O2N, O, F, F, dihydropyran structure) | 1H-NMR (CDCl3) δ: 7.74 (dd, 1H, J = 7.9, 1.3 Hz), 7.43 (dd, 1H, J = 7.6, 1.7 Hz), 7.26 (dd, 1H, J = 7.9, 7.6 Hz) 6:09 (tt, 1H, J = 55.2, 3.9 Hz), 6.03 – 5.99 (m, 1H), 4.36 – 4.31 (m, 2H), 4.20 (td, 2H, J = 13.0, 4.2 Hz), 3.94 (t, 2H, J = 5.3 Hz), 2.53 – 2.45 (m, 2H). |

TABLE 1-continued

| Reference Example No. | A | B | C | NMR |
|---|---|---|---|---|
| 25-2 | | | | 1H-NMR (CDCl3) δ: 7.73 (dd, 1H, J = 7.9, 1.3 Hz), 7.42 (dd, 1H, J = 7.6, 1.7 Hz), 7.24 (dd, 1H, J = 7.9, 7.6 Hz), 6.00 – 5.96 (m, 1H), 4.56 – 4.42 (m, 1H), 4.35 – 4.29 (m, 2H), 3.92 (t, 2H, J = 5.3 Hz), 2.61 – 2.37 (m, 2H), 1.42 (d. 3H, J = 6.6 Hz). |
| 25-3 | | | | 1H-NMR (CDCl3) δ: 7.70 (dd, 1H, J = 7.9, 1.3 Hz), 7.41 (dd, 1H, J = 7.9, 2.0 Hz.), 7.23 (t, 1H, J = 7.9 Hz), 6.02 – 5.97 (m, 1H), 4.35 – 4.29 (m, 2H), 4.20 (t, 2H, J = 6.3 Hz). 3.93 (t, 2H, J = 5.3 Hz), 2.70 – 2.55 (m, 2H), 2.53 – 2.44 (m, 2H). |
| 25-4 | | | | 1H-NMR (CDCl3) δ: 7.84 – 7.79 (m, 2H), 7.17 (t, 1H, J = 7.9 Hz), 4.74 – 4.66 (m, 1H), 1.58 (d, 3H, J = 6.6 Hz). |
| 25-5 | | | | 1H-NMR (CDCl3) δ: 7.49 (dd, 1H, J = 7.9, 1.3 Hz), 7.37 (dd, 1H. J = 7.9, 1.3 Hz), 7.01 (t, 1H, J = 7.9 Hz), 4.41 (q, 2H, J = 8.1 Hz). |

Reference Example 26

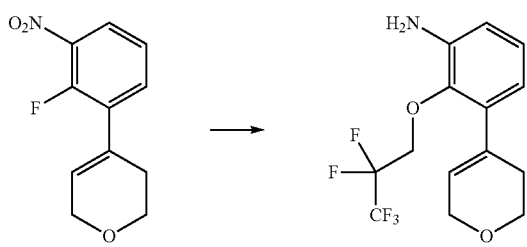 [SMILES: O=[N+]([O-])c1cccc(C2=CCOCC2)c1F ; Nc1cccc(C2=CCOCC2)c1OCC(F)(F)C(F)(F)F]

60% sodium hydride (25 mg) was added to a mixture of 4-(2-fluoro-3-nitrophenyl)-3,6-dihydro-2H-pyran (70 mg), 2,2,3,3,3-pentafluoro-1-propanol (94 mg), N,N-dimethylformamide (1.0 mL), and tetrahydrofuran (0.5 mL) under ice cooling, followed by stirring at room temperature for 10 minutes. Water was added to the reaction liquid which was then extracted twice with ethyl acetate. The solvent of the organic layer was distilled off under reduced pressure, toluene was added, and the solvent was then distilled off under reduced pressure. Toluene was further added and the solvent was distilled off under reduced pressure. A mixture of the obtained residue, ammonium chloride (34 mg), iso-propyl alcohol (1.0 mL), and water (0.50 mL) was stirred at 90° C., and iron (175 mg) was added to the mixture which was then stirred for 40 minutes. After cooling to room temperature, the insoluble matter was removed, and an aqueous sodium chloride solution was added, followed by extraction twice with ethyl acetate. The solvent of the organic layer was distilled off under reduced pressure, and 3-(3,6-dihydro-2H-pyran-4-yl)-2-(2,2,3,3,3-pentafluoropropoxy)aniline (90 mg) was obtained as a yellow oil.

LCMS (Method A)
MS (ESI m/z): 324 (M+H)
RT (min): 1.54

Reference Example 27

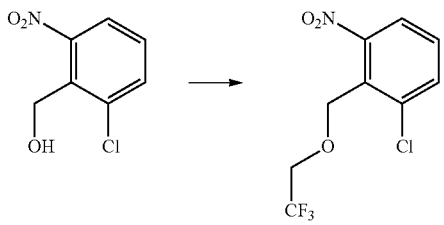 [SMILES: O=[N+]([O-])c1cccc(Cl)c1CO ; O=[N+]([O-])c1cccc(Cl)c1COCC(F)(F)F]

60% sodium hydride (52 mg) was added to a mixture of (2-chloro-6-nitrophenyl)methanol (0.20 g) and N,N-dimethylformamide (2.0 mL) under ice cooling, followed by stirring for 5 minutes. After adding 2,2,2-trifluoroethyl triflate (325 mg) and stirring for 30 minutes, the mixture was stirred at room temperature for 30 minutes. Under ice cooling, 60% sodium hydride (52 mg) and 2,2,2-trifluoroethyl triflate (325 mg) were added to the mixture which was then stirred. Water was added to the mixture which was then extracted with ethyl acetate. The organic layer was washed with water and an aqueous sodium chloride solution, and dried over magnesium sulfate. The solvent was distilled off under reduced pressure, and the obtained residue was purified by silica gel column chromatography (hexane:ethyl acetate gradient elution=100:0 to 80:20). The obtained purified product was purified by silica gel column chromatography (hexane:ethyl acetate gradient elution=100:0 to 90:10) to obtain 1-chloro-3-nitro-2-((2,2,2-trifluoroethoxy)methyl)benzene (86 mg) as a colorless oil.

1H-NMR (CDCl3) δ: 7.74 (d, 1H, J=7.9 Hz), 7.66 (d, 1H, J=7.2 Hz), 7.45 (t, 1H, J=8.3 Hz), 5.06 (s, 2H), 3.91 (q, 2H, J=8.6 Hz).

Reference Example 28

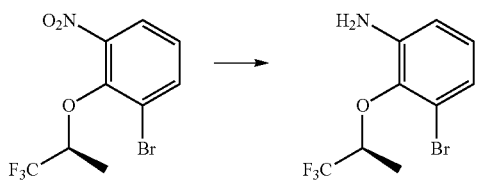 [SMILES: C[C@H](Oc1c(Br)cccc1[N+](=O)[O-])C(F)(F)F ; C[C@H](Oc1c(N)cccc1Br)C(F)(F)F]

(S)-3-bromo-2-((1,1,1-trifluoropropan-2-yl)oxy)aniline was synthesized in the same manner as in Reference Example 4.
LCMS (Method A)
MS (ESI m/z): 283 (M+H)
RT (min): 1.61

Reference Example 29

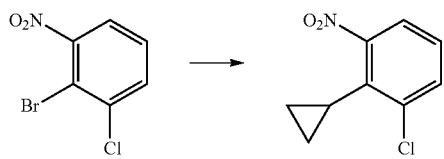 [SMILES: O=[N+]([O-])c1cccc(Cl)c1Br ; O=[N+]([O-])c1cccc(Cl)c1C1CC1]

A mixture of 2-bromo-1-chloro-3-nitrobenzene (0.10 g), cyclopropylboric acid (40 mg), bis(di-tert-butyl(4-dimethylaminophenyl)phosphine)dichloropalladium (II) (30 mg), potassium phosphate (0.18 g), 1,2-dimethoxyethane (3.0 mL), and water (0.50 mL) was irradiated with microwaves (microwave reactor, 140° C., 1 hour, 2.45 GHz, 0 to 240 W). An aqueous sodium chloride solution was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 85:15) to obtain 1-chloro-2-cyclopropyl-3-nitrobenzene (60 mg) as a yellow oil.

1H-NMR (CDCl3) δ: 7.58-7.51 (m, 2H), 7.29 (t, 1H, J=7.6 Hz), 2.05-1.96 (m, 1H), 1.15-1.06 (m, 2H), 0.57-0.49 (m, 2H).

Reference Example 30

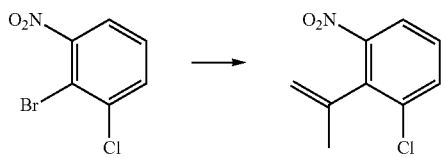

A mixture of 2-bromo-1-chloro-3-nitrobenzene (0.10 g), 2-isopropenyl-4,4,5,5-tetramethyl-1,3,2-dioxaborolane (78 mg), bis(di-tert-butyl(4-dimethylaminophenyl)phosphine) dichloropalladium (II) (30 mg), potassium phosphate (0.18 g), 1,2-dimethoxyethane (3.0 mL), and water (0.50 mL) was irradiated with microwaves (microwave reactor, 100° C., 30 minutes, 2.45 GHz, 0 to 240 W). An aqueous sodium chloride solution was added to the reaction liquid which was then extracted twice with ethyl acetate. The solvent of the organic layer was distilled off under reduced pressure, and the obtained residue was purified by silica gel column chromatography to obtain 1-chloro-3-nitro-2-(propa-1-en-2-yl)benzene (81 mg) as a yellow oil.

1H-NMR (CDCl3) δ: 7.73-7.69 (m, 1H), 7.64-7.59 (m, 1H), 7.35 (t, 1H, J=8.3 Hz), 5.27-5.24 (m, 1H), 4.86-4.84 (m, 1H), 2.19 (s, 3H).

Reference Example 31

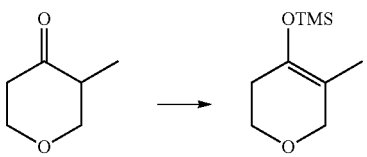

A mixture of 3-methyltetrahydro-4H-pyran-4-one (0.10 g), trimethylsilyl trifluoromethanesulfonate (0.24 μL), triethylamine (0.24 μL), and dichloromethane (1.0 mL) was stirred under ice cooling for 30 minutes. An aqueous sodium chloride solution was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 90:10) to obtain trimethyl ((5-methyl-3,6-dihydro-2H-pyran-4-yl)oxy)silane (84 mg) as a colorless oil.

1H-NMR (CDCl3) δ: 4.01-3.98 (m, 2H), 3.81 (t, 2H, J=5.6 Hz), 2.18-2.10 (m, 2H), 1.50 (s, 3H), 0.19 (s, 9H).

Reference Example 32

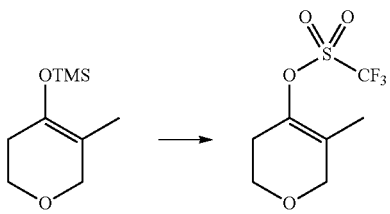

A 1.1 mol/L methyllithium diethyl ether solution (0.12 mL) was added to a mixture of trimethyl ((5-methyl-3,6-dihydro-2H-pyran-4-yl)oxy)silane (60 mg) and tetrahydrofuran (1.0 mL) under ice cooling, followed by stirring for 20 minutes. N-phenylbis(trifluoromethanesulfonimide) (0.23 g) was added to the mixture which was then stirred for 30 minutes. Water was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 80:20) to obtain 5-methyl-3,6-dihydro-2H-pyran-4-yltrifluoromethanesulfonate (50 mg) as a colorless oil.

1H-NMR (CDCl3) δ: 4.13-4.09 (m, 2H), 3.88 (t, 2H, J=5.6 Hz), 2.50-2.42 (m, 2H), 1.72 (s, 3H).

Reference Example 33

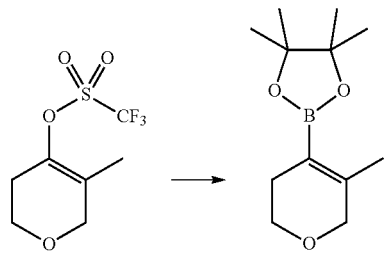

A mixture of 5-methyl-3,6-dihydro-2H-pyran-4-yltrifluoromethanesulfonate (50 mg), bis(pinacolato)diboron (77 mg), [1,1'-bis(diphenylphosphino)ferrocene]palladium (II) dichloride dichloromethane adduct (17 mg), potassium acetate (60 mg), and dimethoxyethane (2.0 mL) was irradiated with microwaves (microwave reactor, 90° C., 30 minutes, 2.45 GHz, 0 to 240 W). Water was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 85:15) to obtain 4,4,5,5-tetramethyl-2-(5-methyl-3,6-dihydro-2H-pyran-4-yl)-1,3,2-dioxaborolane (30 mg) as a colorless oil.

1H-NMR (CDCl3) δ: 4.01-3.97 (m, 2H), 3.70 (t, 2H, J=5.6 Hz), 2.24-2.16 (m, 2H), 1.84 (s, 3H), 1.27 (s, 12H).

Reference Example 34

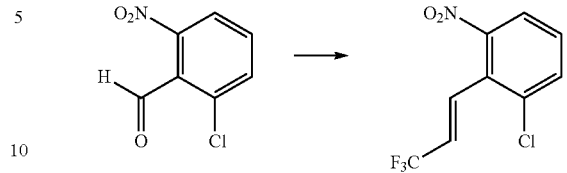

A mixture of 2-chloro-6-nitrobenzaldehyde (0.10 g), diphenyl(2,2,2-trifluoroethyl)phosphine oxide (0.31 g), tetrahydrofuran (1.0 mL), and 1.0 mol/L tetrabutylammonium fluoride tetrahydrofuran solution (0.54 mL) was stirred at room temperature for 4 hours. A 1.0 mol/L tetrabutylammonium fluoride tetrahydrofuran solution (5.4 mL) was added to the mixture which was then stirred overnight at room temperature. Water was added to the reaction liquid which was then extracted with ethyl acetate. The organic layer was washed with an aqueous sodium chloride solution and dried over magnesium sulfate. The solvent of the organic layer was distilled off under reduced pressure, and the obtained residue was purified by silica gel column chromatography (hexane:ethyl acetate gradient elution=100:0 to 90:10) to obtain (E)-1-chloro-3-nitro-2-(3,3,3-trifluoropropa-1-en-1-yl)benzene (93 mg) as a colorless oil.

1H-NMR (CDCl3) δ: 7.88 (d, 1H, J=8.6 Hz), 7.73 (d, 1H, J=7.9 Hz), 7.47 (t, 1H, J=8.3 Hz), 7.35-7.26 (m, 1H), 5.98 (dq, 1H, J=17.3, 5.5 Hz).

Reference Example 35

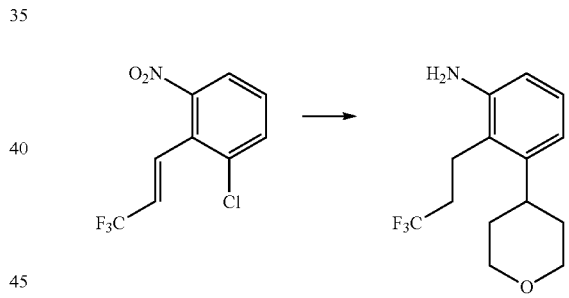

3-(tetrahydro-2H-pyran-4-yl)-2-(3,3,3-trifluoropropyl)aniline was synthesized in the same manner as in Reference Example 19.

LCMS (Method A)
MS (ESI m/z): 274 (M+H)
RT (min): 1.25

Reference Example 36

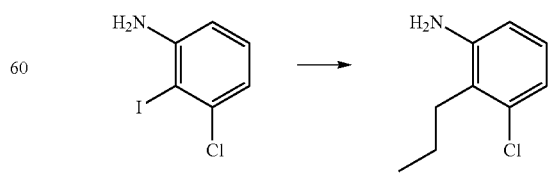

A mixture of 3-chloro-2-iodoaniline (0.50 g), potassium carbonate (0.82 g), N-propylboronic acid (0.26 g), 2-dicyclohexylphosphino-2',6'-diisopropoxybiphenyl (0.18 g), palladium (II) acetate (45 mg), toluene (10 mL), and water (0.5 mL) was stirred at 90° C. for 8 hours. Water was added to the reaction liquid which was then extracted with ethyl acetate. The organic layer was washed with an aqueous sodium chloride solution and dried over magnesium sulfate. The solvent of the organic layer was distilled off under reduced pressure, and the obtained residue was purified by silica gel column chromatography (hexane:ethyl acetate gradient elution=100:0 to 90:10) to obtain 3-chloro-2-propylaniline (0.29 g) as a brown oil.

LCMS (Method A)

MS (ESI m/z): 170 (M+H)

RT (min): 1.51

Reference Example 37

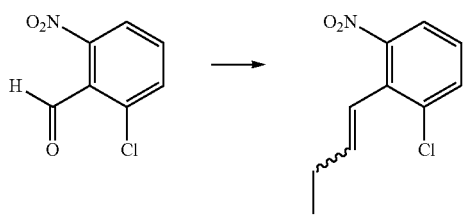

A mixture of 2-chloro-6-nitrobenzaldehyde (1.0 g), potassium carbonate (1.5 g), triphenylpropylphosphonium bromide (2.5 g), and 2-propanol (10 mL) was stirred at 80° C. for 4 hours. Water was added to the reaction liquid which was then extracted with ethyl acetate. The organic layer was washed with an aqueous sodium chloride solution and dried over magnesium sulfate. The solvent of the organic layer was distilled off under reduced pressure, and the obtained residue was purified by silica gel column chromatography (hexane:ethyl acetate gradient elution=100:0 to 95:5) to obtain 2-(but-1-en-1-yl)-1-chloro-3-nitrobenzene (1.2 g) as a colorless oil.

1H-NMR (CDCl3) δ: 7.74-7.13 (m, 3H), 6.42-6.35 (m, 1H), 5.99-5.81 (m, 1H), 2.29-1.77 (m, 2H), 1.13-0.87 (m, 3H).

Reference Example 38

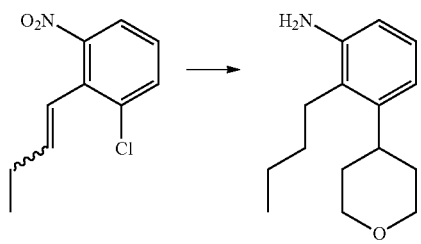 [SMILES: CCC=Cc1c(Cl)cccc1[N+](=O)[O-] ; CCCCc1c(N)cccc1C1CCOCC1]

2-butyl-3-(tetrahydro-2H-pyran-4-yl)aniline was synthesized in the same manner as in Reference Example 19.

LCMS (Method A)

MS (ESI m/z): 234 (M+H)

RT (min): 1.09

Reference Example 39

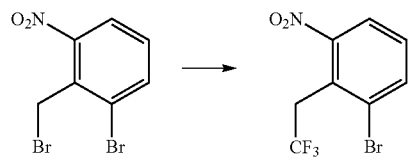 [SMILES: O=[N+]([O-])c1cccc(Br)c1CBr ; O=[N+]([O-])c1cccc(Br)c1CC(F)(F)F]

A mixture of 1-bromo-2-(bromomethyl)-3-nitrobenzene (1.0 g), copper iodide (78 mg), methyl difluoro(fluorosulfonyl)acetate (0.86 mL), and N,N-dimethylformamide (10 mL) was stirred at 70° C. for 3 hours. Copper iodide (78 mg) and methyl difluoro(fluorosulfonyl)acetate (0.86 mL) were added to the mixture which was then stirred for 2 hours. Methyl difluoro(fluorosulfonyl)acetate (0.86 mL) was added to the mixture which was then stirred for 1 hour. After cooling to room temperature, water was added to the reaction liquid which was then extracted twice with ethyl acetate. The organic layer was washed with water and an aqueous sodium chloride solution, and dried over sodium sulfate. The solvent of the organic layer was distilled off under reduced pressure, and the obtained residue was purified by silica gel column chromatography (hexane:ethyl acetate gradient elution=95:5 to 90:10) to obtain 1-bromo-3-nitro-2-(2,2,2-trifluoroethyl)benzene (0.62 g) as a vermilion solid.

1H-NMR (CDCl3) δ: 7.93-7.83 (m, 2H), 7.40 (t, 1H, J=8.4 Hz), 4.27 (q, 2H, J=10.0 Hz).

Reference Example 40

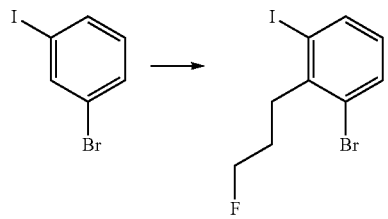 [SMILES: Brc1cccc(I)c1 ; FCCCc1c(Br)cccc1I]

A 20% lithium diisopropylamide hexane-tetrahydrofuran-toluene solution (12 mL) was added to a mixture of 1-bromo-3-iodobenzene (3.5 g), 1-fluoro-3-iodopropane (2.2 mL), and tetrahydrofuran (35 mL) at −60° C., followed by stirring for 3 hours. An aqueous ammonium chloride solution was added to the reaction liquid which was then extracted with ethyl acetate. The organic layer was washed with an aqueous sodium chloride solution and dried over magnesium sulfate. The solvent of the organic layer was distilled off under reduced pressure, and the obtained residue was purified by silica gel column chromatography (hexane:ethyl acetate gradient elution=100:0 to 95:5) to obtain 1-bromo-2-(3-fluoropropyl)-3-iodobenzene (1.7 g).

1H-NMR (CDCl3) δ: 7.79 (d, 1H, J=7.9 Hz), 7.54 (d, 1H, J=7.9 Hz), 6.73 (t, 1H, J=7.9 Hz), 4.58 (dt, 2H, J=46.9, 5.9 Hz), 3.20-3.08 (m, 2H), 2.07-1.89 (m, 2H).

Reference Example 41

The compound B was synthesized from the compound A in the same manner as in Reference Example 2. In Reference Example 41-5,2-(5,6-dihydro-2H-pyran-3-yl)-4,4,5,5-tetramethyl-1,3,2-dioxaborolane was used instead of 3,6-dihydro-2H-pyran-4-boronic acid pinacol ester.

TABLE 2

| Reference Example No. | A | B | LCMS Method | RT (min) | MS (M + H) | NMR |
|---|---|---|---|---|---|---|
| 41-1 | | | — | — | — | 1H-NMR (DMSO-D6) δ : 7.96 (dd, 1H, J = 7.9, 1.3 Hz), 7.69 (dd, 1H, J = 7.6, 1.7 Hz), 7.55 (t, 1H, J = 7.9 Hz), 7.04 (t, 1H, J = 72.3 Hz), 6.02 (s, 1H), 4.23-4.18 (m, 2H), 3.80 (t, 2H, J = 5.6 Hz), 2.43-2.35 (m, 2H). |
| 41-2 | | | — | — | — | 1H-NMR (CDCl3) δ : 7.69-7.61 (m, 1H), 5.97-5.93 (m, 1H), 4.37-4.32 (m, 2H), 4.04 (q, 2H, J = 6.8 Hz), 3.94 (t, 2H, J = 5.3 Hz), 2.48-2.40 (m, 2H), 1.38 (t, 3H, J = 6.9 Hz). |
| 41-3 | | | — | — | — | 1H-NMR (CDCl3) δ : 7.20 (dd, 1H, J = 7.9, 3.3 Hz), 6.85 (dd, 1H, J = 8.9, 3.0 Hz), 5.98-5.94 (m, 1H), 4.31 (q, 2H, J = 2.9 Hz), 3.94-3.85 (m, 4H), 2.53-2.49 (m, 2H), 1.38 (t, 3H, J - 6.9 Hz). |
| 41-4 | | | — | — | — | 1H-NMR (CDCl3) δ : 7.77 (dd, 1H, J = 7.6, 1.7 Hz), 7.50-7.39 (m, 2H), 5.76 (br s, 1H), 4.88 (s, 2H), 4.33-4.28 (m, 2H), 3.97-3.80 (m, 4H), 2.40-2.32 (m, 2H). |
| 41-5 | | | A | 1.48 | 288 | — |
| 41-6 | | | — | — | — | 1H-NMR (CDCl3) δ : 7.62-7.51 (m, 1H), 7.38-7.29 (m, 2H), 5.76 (s, 1H), 4.41-4.31 (m, 2H), 4.04-3.88 (m, 2H), 2.63-2.44 (m, 2H), 2.20-2.07 (m, 1H), 1.06-0.90 (m, 2H), 0.55-0.41 (m, 2H). |

TABLE 2-continued

| Reference Example No. | A | B | LCMS Method | RT (min) | MS (M + H) | NMR |
|---|---|---|---|---|---|---|
| 41-7 | (2-nitro-6-chlorophenyl isopropenyl) | (2-nitro-6-(3,6-dihydro-2H-pyran-4-yl)phenyl isopropenyl) | — | — | — | 1H-NMR (CDCl3) δ : 7.66-7.57 (m, 1H), 7.40-7.31 (m, 2H), 5.75 (s, 1H), 5.21 (s, 1H), 4.87 (s, 1H), 4.33-4.24 (m, 2H), 2.93-3.82 (m, 2H), 2.46-2.33 (m, 2H), 2.09 (s, 3H). |
| 41-8 | (2-amino-6-chlorophenyl propyl) | (2-amino-6-(3,6-dihydro-2H-pyran-4-yl)phenyl propyl) | A | 1.03 | 218 | — |
| 41-9 | (2-nitro-6-bromophenyl CH2CF3) | (2-nitro-6-(3,6-dihydro-2H-pyran-4-yl)phenyl CH2CF3) | — | — | — | 1H-NMR (CDCl3) δ : 7.82 (dd, 1H, J = 8.0, 1.6 Hz), 7.48 (t, 1H, J = 7.6 Hz), 7.42 (dd, 1H, J = 7.6, 1.6 Hz), 5.73 (m, 1H), 4.32 (dd, 2H, J = 10.8, 2.8 Hz), 4.06 (q, 2H, J = 10.4 Hz), 3.94 (t, 2H, J = 10.8 Hz), 2.34-2.30 (m, 2H). |
| 41-10 | (2-nitro-6-bromophenyl CH2CH2OH) | (2-nitro-6-(3,6-dihydro-2H-pyran-4-yl)phenyl CH2CH2OH) | — | — | — | 1H-NMR (CDCl3) δ : 7.74-7.72 (m, 1H), 7.35-7.33 (m, 2H), 5.71-5.69 (m, 1H), 4.30 (q, 2H, J = 2.8 Hz), 3.94 (t, J = 5.2 Hz), 3.80 (t, 2H, J = 6.8 Hz), 3.18 (t, 2H, J = 6.8 Hz), 2.37-2.33 (m, 2H), 1.64 (br s, 1H). |
| 41-11 | (2-nitro-6-bromophenyl OMe) | (2-nitro-6-(3,6-dihydro-2H-pyran-4-yl)phenyl OMe) | — | — | — | 1H-NMR (CDCl3) δ : 7.66 (dd, 1H, J = 8.2, 2.0 Hz), 7.39 (dd, 1H, J = 7.8, 2.0 Hz), 7.18 (t, 1H, J = 8.0 Hz), 5.99-5.97 (m, 1H), 4.33 (dd, 2H, J = 5.4, 2.8 Hz), 3.93 (t, 2H, J = 10.8 Hz), 3.86 (s, 3H), 2.54-2.49 (m, 2H). |
| 41-12 | (2-nitro-6-chlorophenyl OEt) | (2-nitro-6-(3,6-dihydro-2H-pyran-4-yl)phenyl OEt) | — | — | — | 1H-NMR (CDCl3) δ : 7.65 (dd, 1H, J = 8.0, 1.6 Hz), 7.38 (dd, 1H, J = 7.6, 1.6 Hz), 7.16 (t, J = 8.0 Hz), 5.98-5.96 (m, 1H), 4.33 (q, 2H, J = 2.58 Hz), 4.04 (q, 2H, J = 7.2 Hz), 3.92 (t, 2H, J = 5.2 Hz), 2.55-2.50 (m, 2H), 1.36 (t, 3H, J = 7.2 Hz). |

TABLE 2-continued

| Reference Example No. | A | B | LCMS Method | RT (min) | MS (M + H) | NMR |
|---|---|---|---|---|---|---|
| 41-13 | 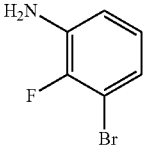 | 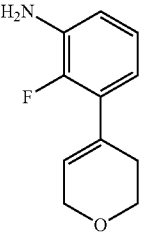 | — | — | — | 1H-NMR (CDCl3) δ : 6.84-6.80 (m, 1H), 6.69-6.64 (m, 1H), 6.47-6.43 (m, 1H), 5.98-5.97 (m, 1H), 5.09 (s, 2H), 4.19 (q, 2H, J = 2.8 Hz), 3.78 (t, 2H, J = 5.6 Hz), 2.39-2.36 (m, 2H). |
| 41-14 | 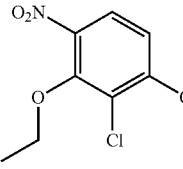 | 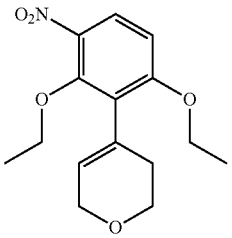 | — | — | — | 1H-NMR (CDCl3) δ : 7.85 (d, 1H, J = 9.2 Hz), 6.66 (d, 1H, J = 9.2 Hz), 5.75-5.73 (m, 1H), 4.32 (q, 2H, J = 2.8 Hz), 4.09 (q, 2H, J = 6.8 Hz), 4.01 (q, 2H, J = 6.8 Hz), 3.92, (t, 2H, J = 5.6 Hz), 2.36-2.04 (m, 2H), 1.43 (t, 3H, J = 6.8 Hz), 1.38 (t, 3H, J = 6.8 Hz). |
| 41-15 | 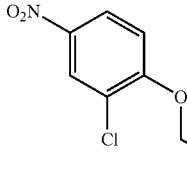 | 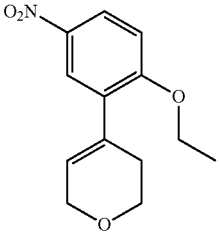 | — | — | — | 1H-NMR (CDCl3) δ : 8.14 (dd, 1H, J = 8.8, 2.8 Hz), 8.09 (d, 1H, J = 3.2 Hz), 6.90 (d, 1H, J = 9.2 Hz), 5.99-5.96 (m, 1H0, 4.34 (q, 2H, J = 2.8 Hz), 4.15 (q, 2H, J = 6.8 Hz), 3.90 (t, 2H, J = 5.2 Hz), 2.55-2.50 (m, 2H), 1.48 (t, 3H, J = 6.8 Hz). |
| 41-16 | 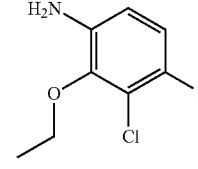 | 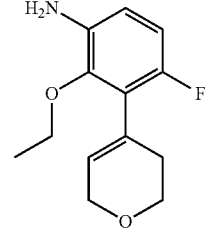 | — | — | — | 1H-NMR (CDCl3) δ : 6.67 (t, 1H, J = 8.8 Hz), 6.59 (dd, 1H, J = 8.8, 5.6 Hz), 5.84-5.83 (m, 1H), 4.32 (q, 2H, J = 2.8 Hz), 3.93 (t, 2H, J = 5.2 Hz), 3.90 (q, 2H, J = 7.2 Hz), 3.67 (br s, 2H), 2.46-2.43 (m, 2H), 1.35 (t, 3H, J = 7.2 Hz). |
| 41-17 | 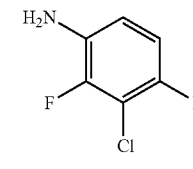 | 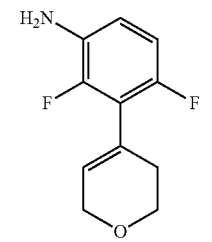 | — | — | — | 1H-NMR (CDCl3) δ : 6.70 (dt, 1H, J = 8.8, 1.6 Hz), 6.62 (dt, 1H, J = 8.8, 5.2 Hz), 5.88-5.86 (m, 1H), 4.32 (q, 2H, J = 2.8 Hz), 3.93 (t, 2H, J = 5.6 Hz), 3.58 (br s, 2H), 2.44-2.41 (m, 2H). |
| 41-18 | 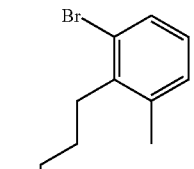 | 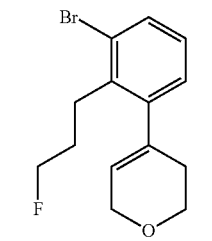 | — | — | — | 1H-NMR (CDCl3) δ : 7.47 (t, 1H, J = 4.6 Hz), 7.06-7.01 (m, 2H), 5.61 (s, 1H), 4.50 (dt, 2H, J = 47.3, 5.8 Hz), 4.28 (q, 2H, J = 2.6 Hz), 3.92 (t, 2H, J = 5.3 Hz), 2.89-2.84 (m, 2H), 2.37-2.26 (m, 2H), 2.07-1.87 (m, 2H). |

TABLE 2-continued

| Reference Example No. | A | B | LCMS Method | RT (min) | MS (M + H) | NMR |
|---|---|---|---|---|---|---|
| 41-19 | 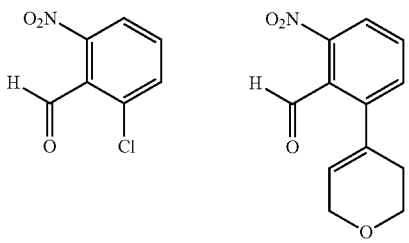 | | — | — | — | 1H-NMR (CDCl3) δ : 10.33 (s, 1H), 7.92 (dd, 1H, J = 8.1, 1.0 Hz), 7.63 (t, 1H, J = 7.9 Hz), 7.56 (dd, 1H, J = 7.6, 1.2 Hz), 5.73-5.69 (m, 1H), 4.29 (q, 2H, J = 2.8 Hz), 3.93 (t, 2H, J = 5.4 Hz), 2.45-2.38 (m, 2H). |

Reference Example 42

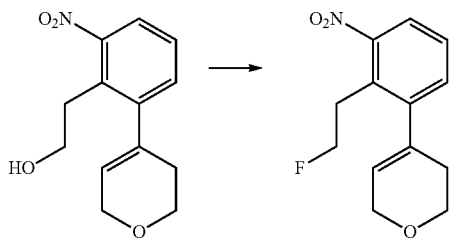 [SMILES: O=[N+]([O-])c1cccc(C2=CCOCC2)c1CCO ; O=[N+]([O-])c1cccc(C2=CCOCC2)c1CCF]

Diethylaminosulfur trifluoride (0.23 mL) was added to a mixture of 2-(2-(3,6-dihydro-2H-pyran-4-yl)-6-nitrophenyl) ethan-1-ol (0.35 g) and dichloromethane (8.0 mL) under ice cooling, followed by stirring overnight. An aqueous sodium hydrogen carbonate solution was added to the mixture which was then extracted with dichloromethane. The organic layer was washed with an aqueous sodium chloride solution and dried over sodium sulfate. The solvent was distilled off under reduced pressure, and the obtained residue was purified by silica gel column chromatography (hexane:ethyl acetate gradient elution=90:10 to 80:20) to obtain 4-(2-(2-fluoroethyl)-3-nitrophenyl)-3,6-dihydro-2H-pyran (0.16 g) as a yellow oil.

1H-NMR (CDCl3) δ: 7.80-7.78 (m, 1H), 7.38 (d, 1H, J=1.6 Hz), 7.36 (s, 1H), 5.70-5.68 (m, 1H), 4.59 (dt, 2H, J=47.2, 6.4 Hz), 4.31 (q, 2H, J=2.8 Hz), 3.94 (t, 2H, J=5.2 Hz), 3.36 (dt, 2H, J=21.6, 6.4 Hz), 2.36-2.31 (m, 2H).

Reference Example 43

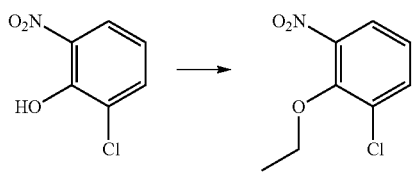

1-chloro-2-ethoxy-3-nitrobenzene was obtained in the same manner as in Reference Example 22.

1H-NMR (DMSO-D6) δ: 7.92 (dd, 1H, J=8.0, 1.6 Hz), 7.88 (dd, 1H, J=8.0, 1.6 Hz), 7.38 (t, 1H, J=8.0 Hz), 4.16 (q, 2H, J=7.2 Hz), 1.35 (t, 3H, J=7.2 Hz).

Reference Example 44

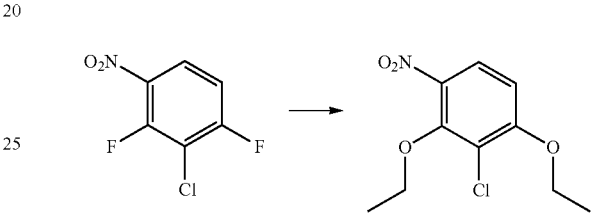

A 20% sodium ethoxide-ethanol solution (270 g) was added dropwise over 20 minutes to a mixture of 2-chloro-1,3-difluoro-4-nitrobenzene (50 g) and ethanol (510 mL) under ice cooling. After stirring at 50° C. for 20 minutes, the mixture was ice-cooled and water (2.5 L) was added thereto. The precipitated solid was collected by filtration and dried to obtain 2-chloro-1,3-diethoxy-4-nitrobenzene (63 g) as a white solid.

1H-NMR (CDCl3) δ: 7.88 (d, 1H, J=9.2 Hz), 6.74 (d, 1H, J=9.2 Hz), 4.21 (q, 2H, J=7.2 Hz), 4.20 (q, 2H, J=6.8 Hz), 1.52 (t, 3H, J=7.2 Hz), 1.49 (t, 3H, J=6.8 Hz).

Reference Example 45

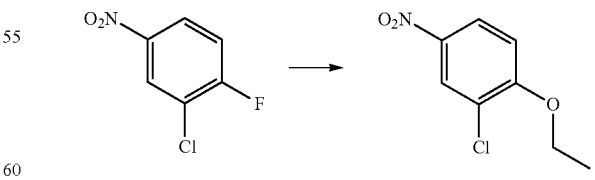

2-chloro-1-ethoxy-4-nitrobenzene was synthesized in the same manner as in Reference Example 44.

1H-NMR (DMSO-D6) δ: 8.31 (d, 1H, J=2.8 Hz), 8.23 (dd, 1H, J=9.2, 2.8 Hz), 7.36 (d, 1H, J=9.2 Hz), 4.29 (q, 2H, J=6.8 Hz), 1.41 (t, 3H, J=6.8 Hz).

Reference Example 46

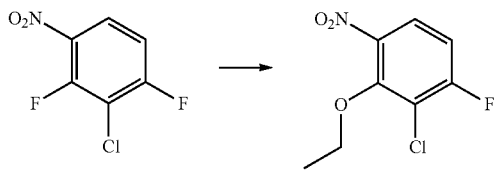

A 20% sodium ethoxide-ethanol solution (1.8 g) was added dropwise to a mixture of 2-chloro-1,3-difluoro-4-nitrobenzene (1.0 g) and ethanol (15 mL) under ice cooling. After stirring at room temperature for 1 hour, water was added to the mixture which was then extracted with ethyl acetate. The organic layer was washed with an aqueous sodium chloride solution and dried over sodium sulfate. The solvent was distilled off under reduced pressure, and the obtained residue was purified by silica gel column chromatography (hexane:ethyl acetate gradient elution=100:0 to 95:5) to obtain 2-chloro-3-ethoxy-1-fluoro-4-nitrobenzene (0.50 g) as a pale yellow oil.

1H-NMR (CDCl3) δ: 7.82 (dd, 1H, J=9.2, 5.6 Hz), 7.05 (dd, 1H, J=9.2, 7.2 Hz), 4.26 (q, 2H, J=7.2 Hz), 1.49 (t, 3H, J=7.2 Hz).

Reference Example 47

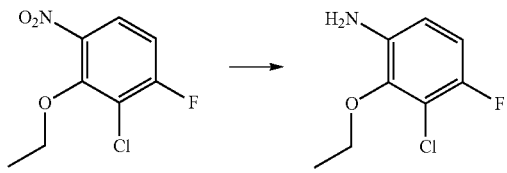

3-chloro-2-ethoxy-4-fluoroaniline was synthesized in the same manner as in Reference Example 4.

1H-NMR (CDCl3) δ: 6.75 (t, 1H, J=8.8 Hz), 6.58 (dd, 1H, J=8.8, 5.4 Hz), 4.07 (q, 2H, J=7.2 Hz), 3.74 (br s, 2H), 1.44 (t, 3H).

Reference Example 48

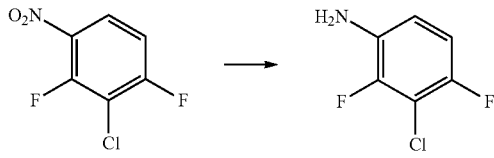 [SMILES: O=[N+]([O-])c1ccc(F)c(Cl)c1F ; Nc1ccc(F)c(Cl)c1F]

3-chloro-2,4-difluoroaniline was synthesized in the same manner as in Reference Example 4.

1H-NMR (CDCl3) δ: 6.79 (dt, 1H, J=8.8, 2.0 Hz), 6.63 (dt, 1H, J=9.2, 5.2 Hz), 3.66 (br s, 2H).

Reference Example 49

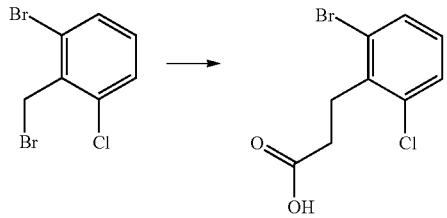 [SMILES: Clc1cccc(Br)c1CBr ; O=C(O)CCc1c(Cl)cccc1Br]

Diethyl malonate (2.7 g) was added to a mixture of 60% sodium hydride (0.68 g) and tetrahydrofuran (40 mL) under ice cooling, followed by stirring at room temperature for 1 hour. A mixture of 1-bromo-2-(bromomethyl)-3-chlorobenzene (4.0 g) and tetrahydrofuran (8.0 mL) was added thereto under ice cooling, followed by stirring at room temperature for 1 hour and 30 minutes. 0.50 mol/L hydrochloric acid (40 mL) was added thereto under ice cooling, and the organic solvent was distilled off under reduced pressure. The mixture was extracted with ethyl acetate, and the solvent was distilled off under reduced pressure. Ethanol (30 mL), a 5.0 mol/L aqueous sodium hydroxide solution (14 mL), and water (16 mL) were added to the residue which was then stirred with heating under reflux for 1 hour and 30 minutes. After cooling to room temperature, the organic solvent was distilled off under reduced pressure. Water (100 mL) was added, the mixture was washed with ethyl acetate, and the pH was adjusted to 1 with concentrated hydrochloric acid. The mixture was extracted twice with ethyl acetate, and the organic layer was washed with an aqueous sodium chloride solution and dried over sodium sulfate. The solvent was distilled off under reduced pressure, xylene (65 mL) was added, and the mixture was stirred overnight with heating under reflux. After cooling to room temperature, the solvent was distilled off under reduced pressure. Hexane was added thereto, followed by stirring. The solid was collected by filtration and dried to obtain 3-(2-bromo-6-chlorophenyl) propionic acid (3.0 g) as a white solid.

1H-NMR (CDCl3) δ: 7.48 (dd, 1H, J=7.9, 1.1 Hz), 7.33 (dd, 1H, J=7.9, 1.1 Hz), 7.03 (t, 1H, J=7.9 Hz), 3.35-3.28 (m, 2H), 2.68-2.62 (m, 2H).

Reference Example 50

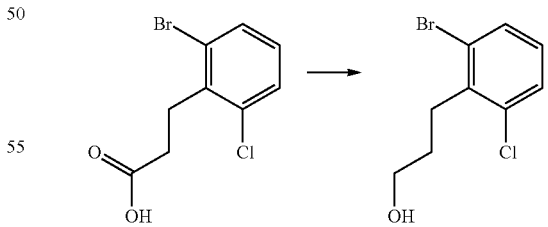

A 1.0 mol/L borane tetrahydrofuran solution (16 mL) was added to a mixture of 3-(2-bromo-6-chlorophenyl)propionic acid (3.0 g) and tetrahydrofuran (30 mL) under ice cooling, followed by stirring for 2 hours. Water, an aqueous sodium carbonate solution, and ethyl acetate were added to the mixture which was then filtered through Celite. The organic layer was washed with an aqueous sodium chloride solution and dried over sodium sulfate. The solvent of the organic layer was distilled off under reduced pressure, and the obtained residue was purified by silica gel column chromatography (hexane:ethyl acetate gradient elution=100:0 to 80:20) to obtain 3-(2-bromo-6-chlorophenyl)propan-1-ol (2.8 g) as a colorless oil.

1H-NMR (CDCl3) δ: 7.46 (dd, 1H, J=8.1, 1.2 Hz), 7.32 (dd, 1H, J=8.1, 1.2 Hz), 6.99 (t, 1H, J=8.1 Hz), 3.79-3.71 (m, 2H), 3.09-3.01 (m, 2H), 1.92-1.83 (m, 2H).

Reference Example 51

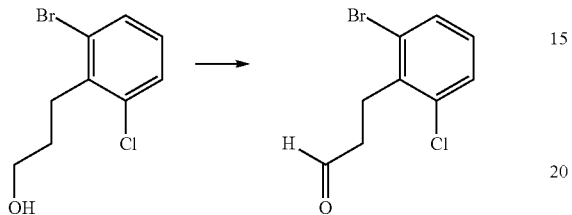

A Dess-Martin reagent (1.0 g) was added to a mixture of 3-(2-bromo-6-chlorophenyl)propan-1-ol (0.50 g) and dichloromethane (15 mL) under ice cooling, followed by stirring at room temperature for 1 hour. An aqueous sodium hydrogen carbonate solution and an aqueous sodium thiosulfate solution were added thereto under ice cooling, followed by extraction with ethyl acetate. The organic layer was washed with an aqueous sodium chloride solution and dried over sodium sulfate. The solvent of the organic layer was distilled off under reduced pressure, and the obtained residue was purified by silica gel column chromatography (hexane:ethyl acetate gradient elution=95:5 to 90:10) to obtain 3-(2-bromo-6-chlorophenyl)propanal (0.45 g) as a colorless oil.

1H-NMR (CDCl3) δ: 9.88 (t, 1H, J=1.2 Hz), 7.47 (dd, 1H, J=8.1, 1.1 Hz), 7.33 (dd, 1H, J=7.9, 1.1 Hz), 7.03 (t, 1H, J=8.1 Hz), 3.32-3.26 (m, 2H), 2.77-2.71 (m, 2H).

Reference Example 52

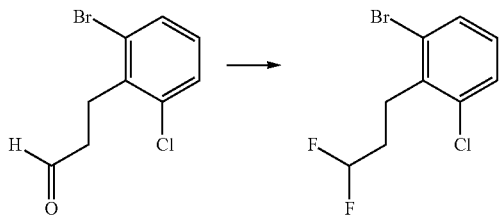 [SMILES: O=CCCc1c(Cl)cccc1Br ; FC(F)CCc1c(Cl)cccc1Br]

A mixture of 3-(2-bromo-6-chlorophenyl)propanal (0.44 g), (diethylamino)difluorosulfonium tetrafluoroborate (0.61 g), dichloromethane (15 mL), and triethylamine trihydrofluoride (0.43 g) was stirred at room temperature for 4 hours. An aqueous sodium hydrogen carbonate solution was added to the reaction liquid which was then extracted twice with methylene chloride. Sodium sulfate and silica gel were added to the organic layer, followed by stirring, and the solid matter was filtered. The solvent was distilled off under reduced pressure to obtain 1-bromo-3-chloro-2-(3,3-difluoropropyl)benzene (0.47 g) as a yellow oil.

1H-NMR (CDCl3) δ: 7.48 (dd, 1H, J=8.1, 1.2 Hz), 7.34 (dd, 1H, J=8.1, 1.2 Hz), 7.03 (t, 1H, J=7.9 Hz), 5.93 (tt, 1H, J=56.4, 4.3 Hz), 3.17-3.10 (m, 2H), 2.20-2.04 (m, 2H).

Reference Example 53

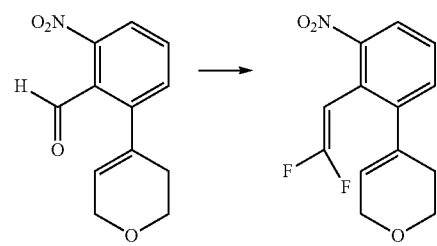 [SMILES: O=Cc1c(C2=CCOCC2)cccc1[N+](=O)[O-] ; O=[N+]([O-])c1cccc(C2=CCOCC2)c1C=C(F)F]

A: A mixture of 2-(3,6-dihydro-2H-pyran-4-yl)-6-nitrobenzaldehyde (0.20 g), triphenylphosphine (0.45 g), and N-methylpyrrolidine (6.0 mL) was stirred at 100° C., and sodium chlorodifluoroacetate (0.31 g) was added thereto, followed by stirring for 5 minutes. Triphenylphosphine (0.23 g) and sodium chlorodifluoroacetate (0.13 g) were added to the mixture which was then stirred for 10 minutes. After cooling to room temperature, water was added to the reaction liquid which was then extracted with ethyl acetate. The organic layer was washed with an aqueous sodium chloride solution and dried over magnesium sulfate. The solvent of the organic layer was distilled off under reduced pressure.

B: A mixture of 2-(3,6-dihydro-2H-pyran-4-yl)-6-nitrobenzaldehyde (0.89 g), triphenylphosphine (2.0 g), and N-methylpyrrolidine (24 mL) was stirred at 100° C., and sodium chlorodifluoroacetate (1.2 g) was added thereto, followed by stirring for 5 minutes. After cooling to room temperature, water was added to the reaction liquid which was then extracted with ethyl acetate. The organic layer was washed with water and an aqueous sodium chloride solution, and dried over magnesium sulfate. The solvent of the organic layer was distilled off under reduced pressure.

The residues obtained in A and B were combined and purified by silica gel column chromatography (hexane:ethyl acetate gradient elution=90:10 to 80:20) to obtain 4-(2-(2,2-difluorovinyl)-3-nitrophenyl)-3,6-dihydro-2H-pyran (0.34 mg) as a brown solid.

1H-NMR (CDCl3) δ: 7.86-7.81 (m, 1H), 7.47-7.43 (m, 2H), 5.75 (br s, 1H), 5.56 (dd, 1H, J=25.4, 1.5 Hz), 4.30 (q, 2H, J=2.7 Hz), 3.91 (t, 2H, J=5.3 Hz), 2.39-2.32 (m, 2H).

Reference Example 54

The compound B was synthesized from the compound A in the same manner as in Reference Example 4.

TABLE 3

| Reference Example No. | A | B | Method | RT (min) | MS (M + H) | NMR |
|---|---|---|---|---|---|---|
| 54-1 | | | A | 1.21 | 242 | — |
| 54-2 | | | A | 1.29 | 256 | — |
| 54-3 | | | A | 1.16 | 256 | — |
| 54-4 | | | A | 1.43 | 288 | — |
| 54-5 | | | A | 1.33 | 288 | — |

TABLE 3-continued
| Reference Example No. | A | B | LCMS Method | RT (min) | MS (M + H) | NMR |
|---|---|---|---|---|---|---|
| 54-6 | 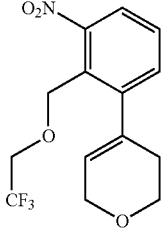 | 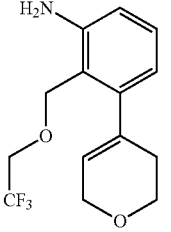 | A | 1.31 | 288 | — |
| 54-7 | 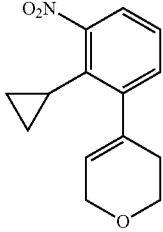 | 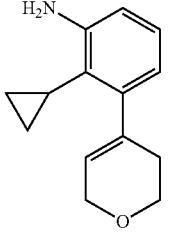 | A | 0.88 | 216 | — |
| 54-8 | 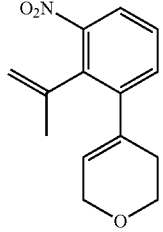 | 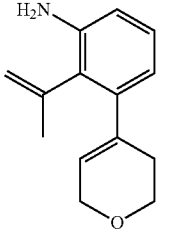 | A | 1.00 | 216 | — |
| 54-9 | 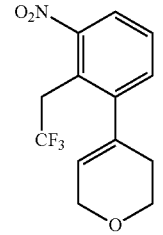 | 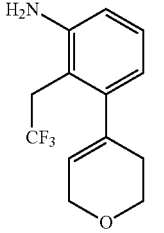 | B | 2.83 | 258 | 1H-NMR (CDCl3) δ : 7.12 (t, 1H, J = 7.6 Hz), 6.67 (dd, 1H, J = 8.0, 1.2 Hz), 6.62 (dd, 1H, J = 7.6, 1.2 Hz), 5.60 (m, 1H), 4.28 (dd, 2H, J = 5.6, 2.8 Hz), 3.90 (t, 2H, J = 5.2 Hz), 3.80 (br, s, 2H), 3.51 (q, 2H, J = 10.8 Hz), 2.31-2.28 (m, 2H). |
| 54-10 | 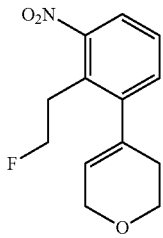 | 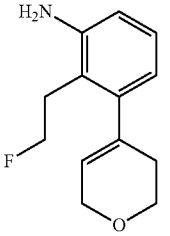 | B | 1.85 | 222 | — |
| 54-11 | 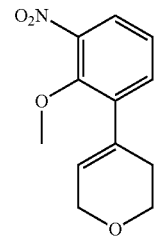 | 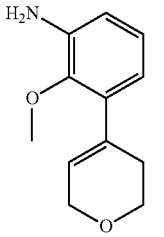 | — | — | — | 1H-NMR (CDCl3) δ : 6.88 (t, 1H, J = 7.6 Hz), 6.68 (dd, 1H, J = 8.0 1.6 Hz), 6.57 (dd, 1H, J = 7.6, 1.6 Hz), 5.93-5.91 (m, 1H), 4.31 (q, 2H, J = 2.8 Hz), 3.91 (t, 2H, J = 5.6 Hz), 3.85 (br s, 2H), 3.70 (s, 3H), 2.55-2.50 (m, 2H). |

TABLE 3-continued

| Reference Example No. | A | B | LCMS Method | RT (min) | MS (M + H) | NMR |
|---|---|---|---|---|---|---|
| 54-12 | [structure: 3-aminophenyl with CH2CF3 and dihydropyran] | [structure: 3-amino-2-ethoxyphenyl with dihydropyran] | — | — | — | 1H-NMR (CDCl3) δ : 6.75 (t, 1H, J = 7.6 Hz), 6.60 (dd, 1H, J = 8.0, 1.6 Hz), 6.34 (dd, 1H, J = 7.6, 1.6 Hz), 5.86-5.84 (m, 1H), 4.82 (s, 2H), 4.18 (q, 2H, J = 2.8 Hz), 3.78 (t, 2H, J = 5.6 Hz), 3.73 (q, 2H, J = 6.8 Hz), 2.41-2.38 (m, 2H), 1.26 (t, 3H, J = 6.8 Hz). |
| 54-13 | [structure: nitro diethoxy phenyl with dihydropyran] | [structure: amino diethoxy phenyl with dihydropyran] | — | — | — | 1H-NMR (CDCl3) δ : 6.61 (d, 1H, J = 8.4 Hz), 6.52 (d, 1H, J = 8.8 Hz), 5.74-5.72 (m, 1H), 4.32 (q, 2H, J = 2.8 Hz), 3.93-3.85 (m, 6H), 3.58 (br s, 2H), 2.47-2.42 (m, 2H), 1.34 (q, 6H, J = 7.2 Hz). |
| 54-14 | [structure: nitro ethoxy phenyl with dihydropyran] | [structure: amino ethoxy phenyl with dihydropyran] | — | — | — | 1H-NMR (DMSO-D6) δ : 6.68 (d, 1H, J = 8.4 Hz), 6.44-6.40 (m, 2H), 5.78-5.77 (m, 1H), 4.62 (br s, 2H), 4.16 (q, 2H, J = 2.8 Hz), 3.84 (q, 2H, J = 7.2 Hz), 3.74 (t, 2H, J = 5.6 Hz), 2.40-2.36 (m, 2H), 1.25 (t, 3H, J = 6.8 Hz). |
| 54-15 | [structure: nitrophenyl with CH=CF2 and dihydropyran] | [structure: aminophenyl with CH=CF2 and dihydropyran] | B | 2.37 | 238 | — |

Reference Example 55

The compound B was synthesized from the compound A in the same manner as in Reference Example 5.

TABLE 4

| Reference Example No. | A | B | LCMS Method | RT (min) | MS (M + H) | NMR |
|---|---|---|---|---|---|---|
| 55-1 | [structure: 3-amino-2-cyclopropylphenyl with dihydropyran] | [structure: 3-amino-2-cyclopropylphenyl with tetrahydropyran] | A | 0.77 | 218 | — |

TABLE 4-continued

| Reference Example No. | A | B | Method | LCMS RT (min) | MS (M + H) | NMR |
|---|---|---|---|---|---|---|
| 55-2 | H₂N-phenyl(isopropenyl)(3,6-dihydro-2H-pyran-4-yl) | H₂N-phenyl(isopropyl)(tetrahydro-2H-pyran-4-yl) | A | 0.82 | 220 | — |
| 55-3 | H₂N-phenyl(CH₂CF₃)(3,6-dihydro-2H-pyran-4-yl) | H₂N-phenyl(CH₂CF₃)(tetrahydro-2H-pyran-4-yl) | B | 2.56 | 260 | — |
| 55-4 | H₂N-phenyl(CH₂CH₂F)(3,6-dihydro-2H-pyran-4-yl) | H₂N-phenyl(CH₂CH₂F)(tetrahydro-2H-pyran-4-yl) | B | 1.13 | 224 | — |
| 55-5 | H₂N-phenyl(CH=CF₂)(3,6-dihydro-2H-pyran-4-yl) | H₂N-phenyl(CH₂CHF₂)(tetrahydro-2H-pyran-4-yl) | B | 2.09 | 242 | — |
| 55-6 | H₂N-phenyl(OCHF₂)(3,6-dihydro-2H-pyran-4-yl) | H₂N-phenyl(OCHF₂)(tetrahydro-2H-pyran-4-yl) | A | 1.18 | 244 | — |

Reference Example 56

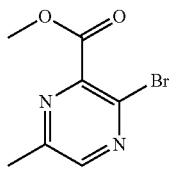

The following compounds were obtained according to the method described in WO2019/043407A.

Methyl 3-bromo-6-methylpyrazine-2-carboxylate

LCMS (Method A)
MS (ESI m/z): 230 (M+H)
RT (min): 0.96

Reference Example 57

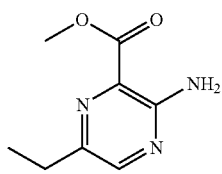

The following compounds were obtained according to the method described in WO2017/221008A.

Methyl 3-amino-6-ethylpyrazine-2-carboxylate

LCMS (Method A)
MS (ESI m/z): 182 (M+H)
RT (min): 0.78

Reference Example 58

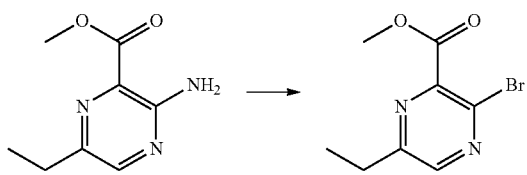

Bromotrimethylsilane (0.85 mL) was added to a mixture of methyl 3-amino-6-ethylpyrazine-2-carboxylate (0.39 g) and dibromomethane (3.9 mL) under water cooling. After stirring at room temperature, pentyl nitrite (0.64 mL) was added to the mixture which was then stirred at 10° C. to 20° C. for 1 hour. An aqueous sodium hydrogen carbonate solution was added thereto, and the organic layer was separated. Chloroform was added to the aqueous layer for extraction. The organic layers were combined, the solvent was distilled off under reduced pressure, and the obtained residue was purified by silica gel column chromatography (hexane:ethyl acetate gradient elution=100:0 to 90:10) to obtain methyl 3-bromo-6-ethylpyrazine-2-carboxylate (0.42 g) as a light brown oil.

LCMS (Method A)
MS (ESI m/z): 246 (M+H)
RT (min): 1.17

Reference Example 59

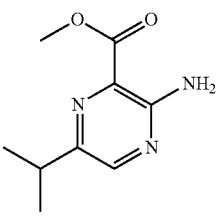

The following compounds were obtained according to the method described in US2011/306589A.

Methyl 3-amino-6-isopropylpyrazine-2-carboxylate

LCMS (Method A)
MS (ESI m/z): 196 (M+H)
RT (min): 0.98

Reference Example 60

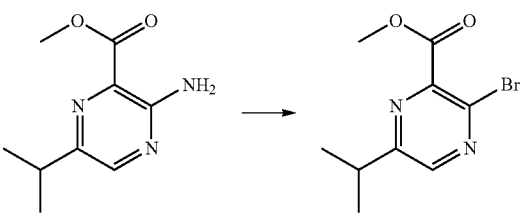

Methyl 3-bromo-6-isopropylpyrazine-2-carboxylate was obtained in the same manner as in Reference Example 58.

LCMS (Method A)
MS (ESI m/z): 259 (M+H)
RT (min): 1.37

Example 1

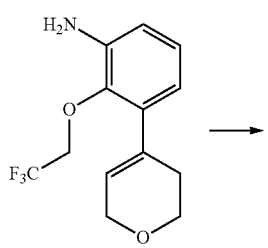

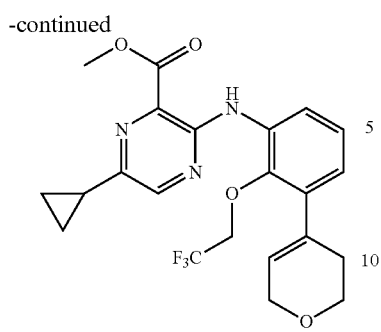

A mixture of 3-(3,6-dihydro-2H-pyran-4-yl)-2-(2,2,2-trifluoroethoxy)aniline (34 mg), methyl 3-bromo-6-cyclopropylpyrazine-2-carboxylate (45 mg), tris(dibenzylideneacetone)dipalladium (0) (25 mg), 4,5-bis(diphenylphosphino)-9,9-dimethylxanthene (31 mg), cesium carbonate (88 mg), and toluene (2.0 mL) was irradiated with microwaves (microwave reactor, 140° C., 1.5 hours, 2.45 GHz, 0 to 240 W). Water was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 80:20) to obtain methyl 6-cyclopropyl-3-((3-(3,6-dihydro-2H-pyran-4-yl)-2-(2,2,2-trifluoroethoxy)phenyl)amino)pyrazine-2-carboxylate (60 mg) as a yellow solid.

LCMS (Method A)
MS (ESI m/z): 450 (M+H)
RT (min): 1.90

Example 2

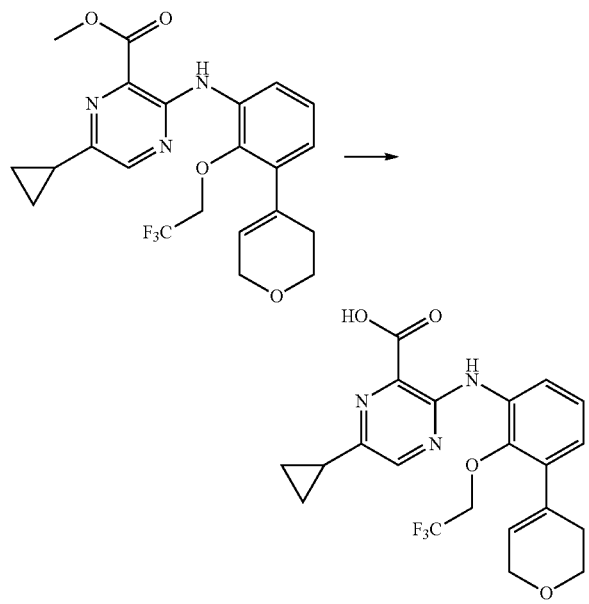

A mixture of methyl 6-cyclopropyl-3-((3-(3,6-dihydro-2H-pyran-4-yl)-2-(2,2,2-trifluoroethoxy)phenyl)amino)pyrazine-2-carboxylate (60 mg), a 5 mmol/L aqueous sodium hydroxide solution (53 μL), tetrahydrofuran (0.50 mL), and ethanol (0.50 mL) was stirred at 50° C. for 1 hour. After cooling to room temperature, the pH was adjusted to 6 with 1 mmol/L hydrochloric acid. An aqueous sodium chloride solution was added to the mixture which was then extracted twice with ethyl acetate. The solvent of the organic layer was distilled off under reduced pressure, and the obtained residue was purified by silica gel column chromatography (hexane:ethyl acetate gradient elution=100:0 to 70:30) to obtain 6-cyclopropyl-3-((3-(3,6-dihydro-2H-pyran-4-yl)-2-(2,2,2-trifluoroethoxy)phenyl)amino)pyrazine-2-carboxylic acid (39 mg) as a yellow solid.

1H-NMR (DMSO-D6) δ: 13.41 (br s, 1H), 10.54 (br s, 1H), 8.43 (s, 1H), 8.34 (dd, 1H, J=8.6, 1.3 Hz), 7.17 (dd, 1H, J=7.9, 8.6 Hz), 6.90 (dd, 1H, J=7.9, 1.3 Hz), 5.97 (s, 1H), 4.42 (q, 2H, J=9.0 Hz), 4.24-4.17 (m, 2H), 3.82 (t, 2H, J=5.3 Hz), 2.42 (br s, 2H), 2.21-2.11 (m, 1H), 1.01-0.91 (m, 4H).

LCMS (Method A)
MS (ESI m/z): 436 (M+H)
RT (min): 1.74

Example 3

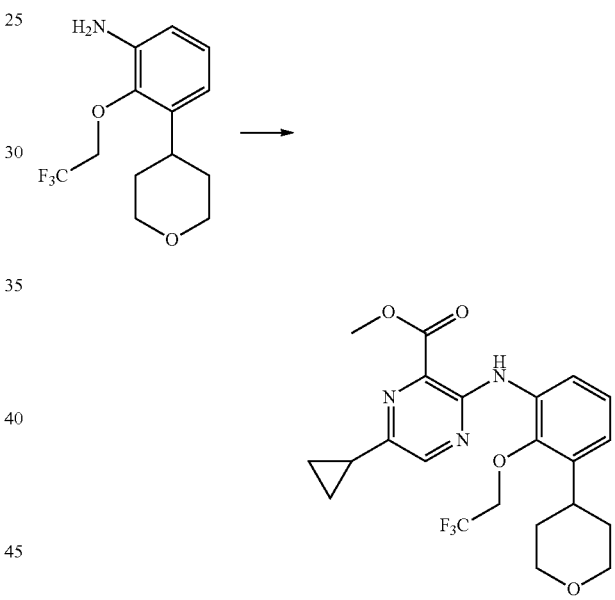

A mixture of 3-(tetrahydro-2H-pyran-4-yl)-2-(2,2,2-trifluoroethoxy)aniline (30 mg), methyl 3-bromo-6-cyclopropylpyrazine-2-carboxylate (33 mg), tris(dibenzylideneacetone)dipalladium (0) (20 mg), 4,5-bis(diphenylphosphino)-9,9-dimethylxanthene (24 mg), cesium carbonate (67 mg), and toluene (2.0 mL) was irradiated with microwaves (microwave reactor, 140° C., 1 hour, 2.45 GHz, 0 to 240 W). Water was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 80:20) to obtain methyl 6-cyclopropyl-3-((3-(tetrahydro-2H-pyran-4-yl)-2-(2,2,2-trifluoroethoxy)phenyl)amino)pyrazine-2-carboxylate (18 mg) as a yellow oil.

LCMS (Method A)
MS (ESI m/z): 452 (M+H)
RT (min): 1.88

Example 4

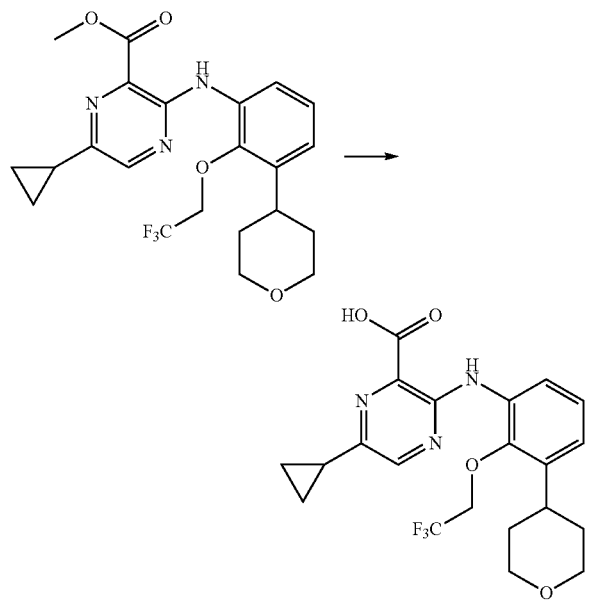

A mixture of methyl 6-cyclopropyl-3-((3-(tetrahydro-2H-pyran-4-yl)-2-(2,2,2-trifluoroethoxy)phenyl)amino)pyrazine-2-carboxylate (18 mg), a 5 mmol/L aqueous sodium hydroxide solution (16 μL), tetrahydrofuran (0.50 mL), and ethanol (0.50 mL) was stirred at 50° C. for 15 minutes. After cooling to room temperature, the pH was adjusted to 3 with 1 mmol/L hydrochloric acid. An aqueous sodium chloride solution was added to the mixture which was then extracted twice with ethyl acetate. The solvent of the organic layer was distilled off under reduced pressure, and the obtained residue was purified by silica gel column chromatography (hexane: ethyl acetate gradient elution=100:0 to 0:100) to obtain 6-cyclopropyl-3-((3-(tetrahydro-2H-pyran-4-yl)-2-(2,2,2-trifluoroethoxy)phenyl)amino)pyrazine-2-carboxylic acid (18 mg) as a yellow solid.

1H-NMR (DMSO-D6) δ: 13.45 (br s, 1H), 10.53 (br s, 1H), 8.41 (s, 1H), 8.27-8.20 (m, 1H), 7.22-7.13 (m, 1H), 7.04-6.97 (m, 1H), 4.53 (q, 2H, J=9.0 Hz), 4.03-3.92 (m, 2H), 3.49-3.38 (m, 2H), 3.24-3.11 (m, 1H), 2.21-2.11 (m, 1H), 1.76-1.62 (m, 4H), 1.01-0.89 (m, 4H).

LCMS (Method A)
MS (ESI m/z): 438 (M+H)
RT (min): 1.70

Example 5

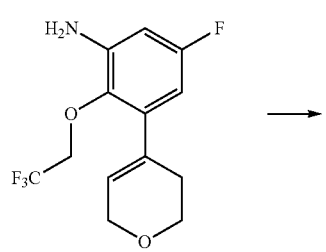

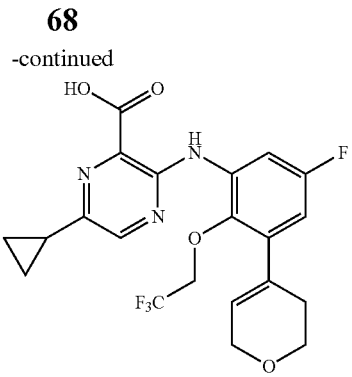

A mixture of 3-(3,6-dihydro-2H-pyran-4-yl)-5-fluoro-2-(2,2,2-trifluoroethoxy)aniline (50 mg), methyl 3-bromo-6-cyclopropylpyrazine-2-carboxylate (44 mg), tris(dibenzylideneacetone)dipalladium (0) (24 mg), 4,5-bis(diphenylphosphino)-9,9-dimethylxanthene (30 mg), cesium carbonate (0.11 g), and toluene (2.0 mL) was irradiated with microwaves (microwave reactor, 140° C., 1.5 hours, 2.45 GHz, 0 to 240 W). Methanol (4.0 mL) and a 5 mmol/L aqueous sodium hydroxide solution (0.15 mL) were added to the reaction liquid which was then stirred at 50° C. for 30 minutes. After cooling to room temperature, water and ethyl acetate were added thereto, and an aqueous citric acid solution was added to adjust the pH to 2. The organic layer was separated, washed with a saturated aqueous sodium chloride solution, and then dried over magnesium sulfate. The solvent was distilled off under reduced pressure, and the obtained residue was purified by silica gel column chromatography (hexane:ethyl acetate gradient elution=90:10 to 70:30) to obtain 6-cyclopropyl-3-((3-(3,6-dihydro-2H-pyran-4-yl)-5-fluoro-2-(2,2,2-trifluoroethoxy)phenyl)amino) pyrazine-2-carboxylic acid (46 mg) as a yellow solid.

1H-NMR (CDCl3) δ: 10.49 (s, 1H), 8.46 (s, 1H), 8.29 (dd, 1H, J=10.9, 3.0 Hz), 6.61 (dd, 1H, J=8.6, 3.3 Hz), 6.04 (s, 1H), 4.32 (d, 2H, J=2.6 Hz), 4.22 (q, 2H, J=8.4 Hz), 3.93 (t, 2H, J=5.6 Hz), 2.50 (s, 2H), 2.20-2.03 (m, 1H), 1.15-0.96 (m, 4H).

LCMS (Method A)
MS (ESI m/z): 454 (M+H)
RT (min): 1.81

Example 6

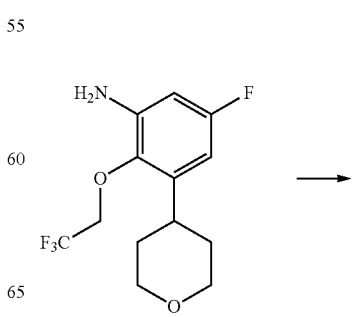

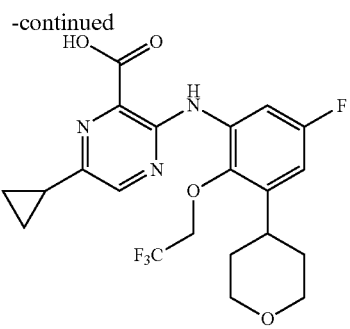

A mixture of 5-fluoro-3-(tetrahydro-2H-pyran-4-yl)-2-(2,2,2-trifluoroethoxy)aniline (32 mg), methyl 3-bromo-6-cyclopropylpyrazine-2-carboxylate (31 mg), tris(dibenzylideneacetone)dipalladium (0) (15 mg), 4,5-bis(diphenylphosphino)-9,9-dimethylxanthene (19 mg), cesium carbonate (71 mg), and toluene (1.6 mL) was irradiated with microwaves (microwave reactor, 130° C., 1 hour, 2.45 GHz, 0 to 240 W). Methanol (1.6 mL) and a 5 mmol/L aqueous sodium hydroxide solution (0.12 mL) were added to the reaction liquid which was then stirred at 50° C. for 30 minutes. Water and ethyl acetate were added to the reaction liquid, and an aqueous citric acid solution was added to adjust the pH to 2. The organic layer was separated, washed with water and a saturated aqueous sodium chloride solution, and dried over sodium sulfate. The solvent was distilled off under reduced pressure, and the obtained residue was purified by silica gel column chromatography (hexane:ethyl acetate gradient elution=90:10 to 50:50) to obtain 6-cyclopropyl-3-((5-fluoro-3-(tetrahydro-2H-pyran-4-yl)-2-(2,2,2-trifluoroethoxy)phenyl)amino) pyrazine-2-carboxylic acid (6.5 mg) as a yellow solid.

1H-NMR (CD3OD) δ: 8.36 (s, 1H), 8.26 (dd, 1H, J=10.9, 3.0 Hz), 6.69 (dd, 1H, J=9.6, 3.0 Hz), 4.41 (q, 2H, J=8.8 Hz), 4.06 (d, 2H, J=11.2 Hz), 3.61-3.50 (m, 3H), 2.20-2.10 (m, 1H), 1.79-1.71 (m, 4H), 1.07-0.98 (m, 4H).

LCMS (Method A)
MS (ESI m/z): 456 (M+H)
RT (min): 1.77

Example 7

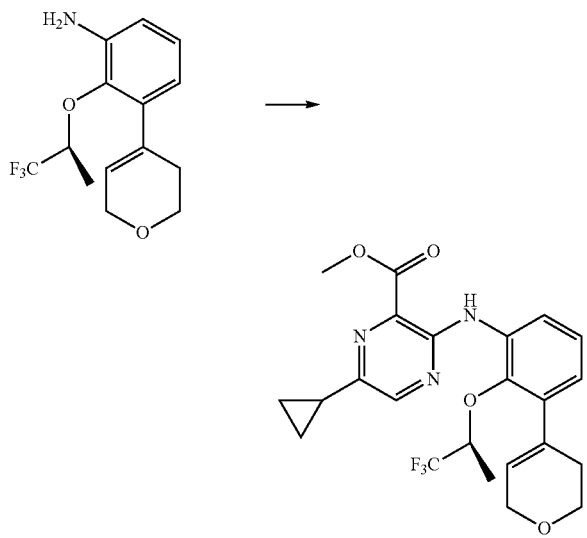

A mixture of (S)-3-(3,6-dihydro-2H-pyran-4-yl)-2-((1,1,1-trifluoropropan-2-yl)oxy)aniline (40 mg), methyl 3-bromo-6-cyclopropylpyrazine-2-carboxylate (52 mg), tris(dibenzylideneacetone)dipalladium (0) (29 mg), 4,5-bis(diphenylphosphino)-9,9-dimethylxanthene (36 mg), cesium carbonate (0.10 g), and toluene (2.0 mL) was irradiated with microwaves (microwave reactor, 140° C., 1.5 hours, 2.45 GHz, 0 to 240 W). Water was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 80:20) to obtain methyl (S)-6-cyclopropyl-3-((3-(3,6-dihydro-2H-pyran-4-yl)-2-((1,1,1-trifluoropropan-2-yl)oxy)phen yl)amino)pyrazine-2-carboxylate (46 mg) as a yellow oil.

LCMS (Method A)
MS (ESI m/z): 464 (M+H)
RT (min): 1.95

Example 8

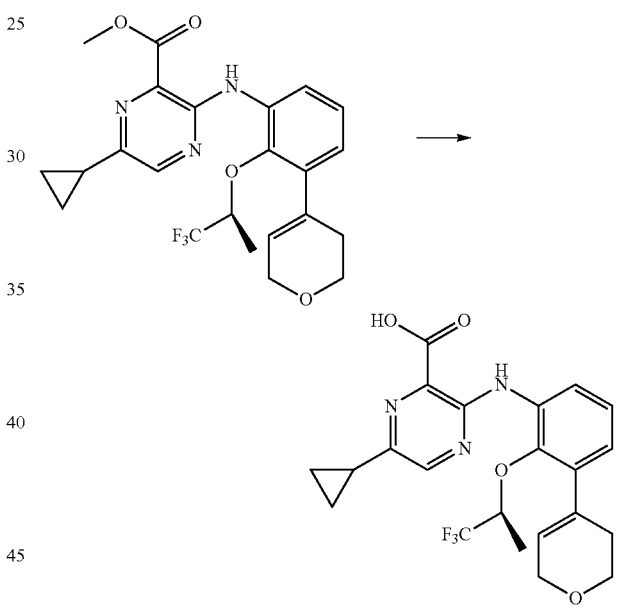

A mixture of methyl (S)-6-cyclopropyl-3-((3-(3,6-dihydro-2H-pyran-4-yl)-2-((1,1,1-trifluoropropan-2-yl)oxy)phen yl)amino)pyrazine-2-carboxylate (46 mg), a 5 mmol/L aqueous sodium hydroxide solution (40 μL), tetrahydrofuran (0.50 mL), and ethanol (0.50 mL) was stirred at 50° C. for 15 minutes. After cooling to room temperature, the pH was adjusted to 6 with 1 mmol/L hydrochloric acid. An aqueous sodium chloride solution was added to the mixture which was then extracted twice with ethyl acetate. The solvent of the organic layer was distilled off under reduced pressure, and the obtained residue was purified by silica gel column chromatography (hexane:ethyl acetate gradient elution=80:20 to 0:100) to obtain (S)-6-cyclopropyl-3-((3-(3,6-dihydro-2H-pyran-4-yl)-2-((1,1,1-trifluoropropan-2-yl)oxy)phen yl)amino)pyrazine-2-carboxylic acid (43 mg) as a yellow solid.

1H-NMR (DMSO-D6) δ: 13.45 (br s, 1H), 10.51 (br s, 1H), 8.42 (s, 1H), 8.34 (dd, 1H, J=8.6, 1.3 Hz), 7.16 (dd, 1H, J=7.9, 8.6 Hz), 6.91-6.88 (m, 1H), 5.96 (s, 1H), 4.73-4.57

(m, 1H), 4.23-4.16 (m, 2H), 3.82 (t, 2H, J=5.3 Hz), 2.47-2.35 (m, 2H), 2.20-2.11 (m, 1H), 1.28 (d, 3H, J=6.6 Hz), 1.01-0.90 (m, 4H).
LCMS (Method A)
MS (ESI m/z): 450 (M+H)
RT (min): 1.80

Example 9

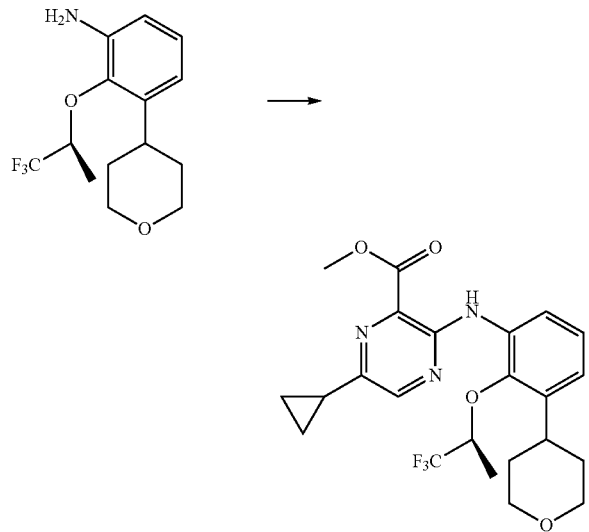

A mixture of (S)-3-(tetrahydro-2H-pyran-4-yl)-2-((1,1,1-trifluoropropan-2-yl)oxy)aniline (21 mg), methyl 3-bromo-6-cyclopropylpyrazine-2-carboxylate (22 mg), tris(dibenzylideneacetone)dipalladium (0) (13 mg), 4,5-bis(diphenylphosphino)-9,9-dimethylxanthene (16 mg), cesium carbonate (45 mg), and toluene (2.0 mL) was irradiated with microwaves (microwave reactor, 140° C., 1 hour, 2.45 GHz, 0 to 240 W). Water was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 70:30) to obtain methyl (S)-6-cyclopropyl-3-((3-(tetrahydro-2H-pyran-4-yl)-2-((1,1,1-trifluoropropan-2-yl)oxy)phenyl) amino)pyrazine-2-carboxylate (24 mg) as a yellow solid.
LCMS (Method A)
MS (ESI m/z): 466 (M+H)
RT (min): 1.91

Example 10

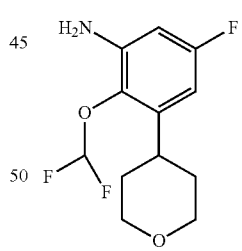

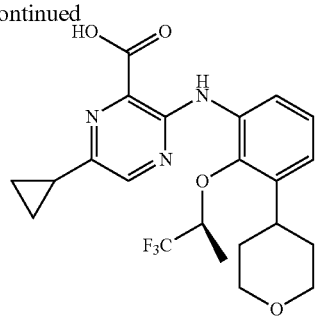

A mixture of methyl (S)-6-cyclopropyl-3-((3-(tetrahydro-2H-pyran-4-yl)-2-((1,1,1-trifluoropropan-2-yl)oxy)phenyl) amino)pyrazine-2-carboxylate (24 mg), a 5 mmol/L aqueous sodium hydroxide solution (21 µL), tetrahydrofuran (0.50 mL), and ethanol (0.50 mL) was stirred at 50° C. for 35 minutes. After cooling to room temperature, the pH was adjusted to 6 with 1 mmol/L hydrochloric acid. An aqueous sodium chloride solution was added to the mixture which was then extracted twice with ethyl acetate. The solvent of the organic layer was distilled off under reduced pressure, and the obtained residue was purified by silica gel column chromatography (hexane:ethyl acetate gradient elution=100:0 to 0:100) to obtain (S)-6-cyclopropyl-3-((3-(tetrahydro-2H-pyran-4-yl)-2-((1,1,1-trifluoropropan-2-yl)oxy) phenyl) amino)pyrazine-2-carboxylic acid (22 mg) as a yellow solid.
1H-NMR (DMSO-D6) δ: 13.45 (br s, 1H), 10.34 (br s, 1H), 8.38 (s, 1H), 8.12-8.07 (m, 1H), 7.20-7.12 (m, 1H), 7.06-7.00 (m, 1H), 4.78-4.68 (m, 1H), 4.04-3.92 (m, 2H), 3.47-3.36 (m, 2H), 3.22-3.10 (m, 1H), 2.20-2.09 (m, 1H), 1.79-1.56 (m, 4H), 1.30 (d, 3H, J=6.6 Hz), 1.00-0.89 (m, 4H).
LCMS (Method A)
MS (ESI m/z): 452 (M+H)
RT (min): 1.74

Example 11

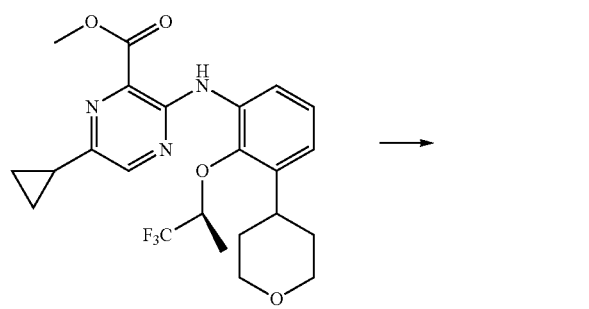

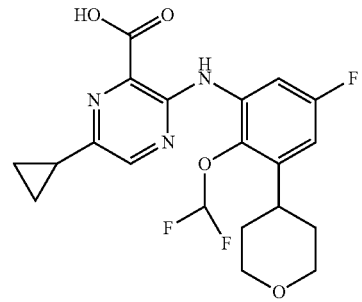 [SMILES: O=C(O)c1nc(C2CC2)cnc1Nc1cc(F)cc(C2=CCOCC2)c1OC(F)F]

A mixture of 2-(difluoromethoxy)-5-fluoro-3-(tetrahydro-2H-pyran-4-yl)aniline (32 mg), methyl 3-bromo-6-cyclopropylpyrazine-2-carboxylate (35 mg), tris(dibenzylideneacetone)dipalladium (0) (17 mg), 4,5-bis(diphenylphosphino)-9,9-dimethylxanthene (21 mg), cesium carbonate (80 mg), and toluene (1.6 mL) was irradiated with microwaves (microwave reactor, 130° C., 1 hour, 2.45 GHz, 0 to 240 W). Methanol (1.6 mL) and a 5 mmol/L aqueous sodium hydroxide solution (0.12 mL) were added to the reaction liquid which was then stirred at 50° C. for 40 minutes. After cooling to room temperature, water and ethyl acetate were added thereto, and an aqueous citric acid solution was added to adjust the pH to 2. The organic layer was separated, washed with water and a saturated aqueous sodium chloride solution, and dried over sodium sulfate. The solvent was distilled off under reduced pressure, and the obtained residue was purified by silica gel column chromatography (hexane:ethyl acetate gradient elution=90:10 to 50:50) to obtain 6-cyclopropyl-3-((2-(difluoromethoxy)-5-fluoro-3-(tetrahydro-2H-pyran-4-yl)phenyl)amino)pyrazine-2-carboxylic acid (11 mg) as a yellow solid.

1H-NMR (CD3OD) δ: 8.32-8.27 (m, 2H), 6.97-6.44 (m, 2H), 4.04 (d, 2H, J=12.6 Hz), 3.61-3.50 (m, 3H), 2.24-2.05 (m, 1H), 1.73-1.70 (m, 4H), 1.07-0.95 (m, 4H).
LCMS (Method A)
MS (ESI m/z): 424 (M+H)
RT (min): 1.69

Example 12

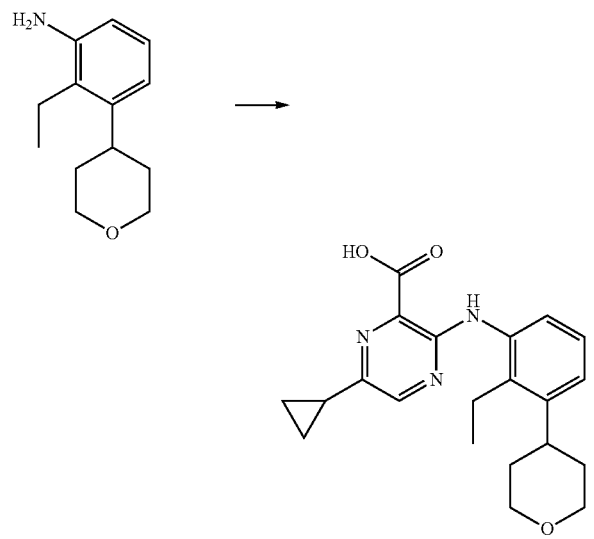

A mixture of 2-ethyl-3-(tetrahydro-2H-pyran-4-yl)aniline (19 mg), methyl 3-bromo-6-cyclopropylpyrazine-2-carboxylate (29 mg), tris(dibenzylideneacetone)dipalladium (0) (13 mg), 4,5-bis(diphenylphosphino)-9,9-dimethylxanthene (16 mg), cesium carbonate (60 mg), and toluene (0.76 mL) was irradiated with microwaves (microwave reactor, 130° C., 1 hour, 2.45 GHz, 0 to 240 W). Methanol (1.0 mL) and a 5 mmol/L aqueous sodium hydroxide solution (92 µL) were added to the reaction liquid which was then stirred at 50° C. for 30 minutes. After cooling to room temperature, water and ethyl acetate were added thereto, and an aqueous citric acid solution was added to adjust the pH to 2. The organic layer was separated, washed with water and a saturated aqueous sodium chloride solution, and dried over magnesium sulfate. The solvent was distilled off under reduced pressure, and the obtained residue was purified by silica gel column chromatography (hexane:ethyl acetate gradient elution=90:10 to 50:50) to obtain 6-cyclopropyl-3-((2-ethyl-3-(tetrahydro-2H-pyran-4-yl)phenyl)amino)pyrazine-2-carboxylic acid (12 mg) as a yellow solid.

1H-NMR (CDCl3) δ: 9.70 (s, 1H), 8.31 (s, 1H), 7.65 (d, 1H, J=7.9 Hz), 7.25-7.23 (m, 1H), 7.13 (d, 1H, J=6.6 Hz), 4.10 (dd, 2H, J=11.2, 4.0 Hz), 3.56 (t, 2H, J=10.9 Hz), 3.08-2.96 (m, 1H), 2.71 (t, 2H, J=8.3 Hz), 2.10-1.99 (m, 1H), 1.96-1.81 (m, 2H), 1.72-1.63 (m, 2H), 1.62-1.49 (m, 2H), 1.09-0.91 (m, 4H), 1.05 (t, 3H, J=7.3 Hz).
LCMS (Method A)
MS (ESI m/z): 368 (M+H)
RT (min): 1.63

Example 13

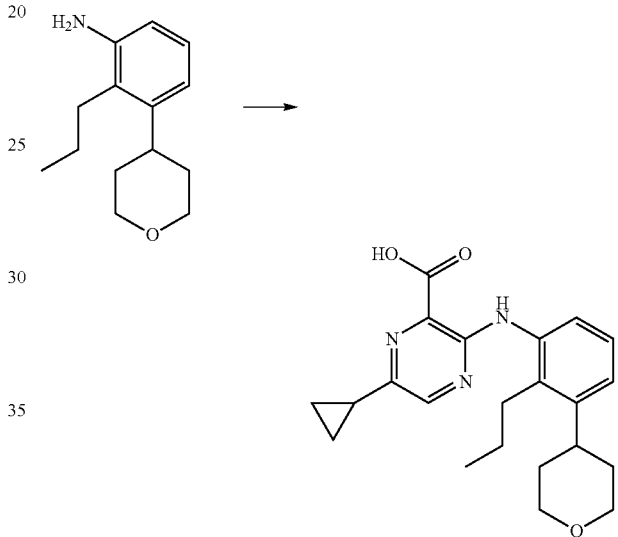

A mixture of 2-propyl-3-(tetrahydro-2H-pyran-4-yl)aniline (0.24 g), methyl 3-bromo-6-cyclopropylpyrazine-2-carboxylate (0.31 g), tris(dibenzylideneacetone)dipalladium (0) (0.15 g), 4,5-bis(diphenylphosphino)-9,9-dimethylxanthene (0.19 g), cesium carbonate (0.71 g), and toluene (12 mL) was irradiated with microwaves (microwave reactor, 140° C., 1.5 hours, 2.45 GHz, 0 to 240 W). Methanol (12 mL) and a 5 mmol/L aqueous sodium hydroxide solution (1.1 mL) were added to the reaction liquid which was then stirred at 50° C. for 30 minutes. After cooling to room temperature, water and ethyl acetate were added thereto, and an aqueous citric acid solution was added to adjust the pH to 3. The organic layer was separated, washed with a saturated aqueous sodium chloride solution, and then dried over magnesium sulfate. The solvent was distilled off under reduced pressure, and the obtained residue was purified by silica gel column chromatography (hexane:ethyl acetate gradient elution=90:10 to 70:30) to obtain 6-cyclopropyl-3-((2-propyl-3-(tetrahydro-2H-pyran-4-yl)phenyl)amino)pyrazine-2-carboxylic acid (0.22 g) as a yellow solid.

1H-NMR (CDCl3) δ: 9.70 (s, 1H), 8.31 (s, 1H), 7.65 (d, 1H, J=7.9 Hz), 7.25-7.23 (m, 1H), 7.13 (d, 1H, J=6.6 Hz), 4.10 (dd, 2H, J=11.2, 4.0 Hz), 3.56 (t, 2H, J=10.9 Hz), 3.08-2.96 (m, 1H), 2.71 (t, 2H, J=8.3 Hz), 2.10-1.99 (m, 1H), 1.96-1.81 (m, 2H), 1.72-1.63 (m, 2H), 1.62-1.49 (m, 2H), 1.09-0.91 (m, 4H), 1.05 (t, 3H, J=7.3 Hz).

LCMS (Method A)
MS (ESI m/z): 382 (M+H)
RT (min): 1.74

Example 14

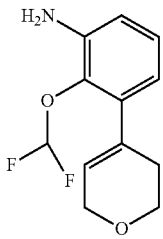

A mixture of 2-(difluoromethoxy)-3-(3,6-dihydro-2H-pyran-4-yl)aniline (60 mg), methyl 3-bromo-6-cyclopropylpyrazine-2-carboxylate (64 mg), potassium phosphate (0.21 g), [1,3-bis(2,6-di-3-pentylphenyl)imidazol-2-ylidene](3-chloropyridyl)dichloropalladium (II) (40 mg), and tert-butyl alcohol (2.4 mL) was irradiated with microwaves (microwave reactor, 135° C., 1 hour, 2.45 GHz, 0 to 240 W). Water and ethyl acetate were added to the reaction liquid, and the pH was adjusted to 2.7 with 1 mol/L hydrochloric acid. The organic layer was separated, washed with an aqueous sodium chloride solution, and dried over sodium sulfate. The solvent of the organic layer was distilled off under reduced pressure, and the obtained residue was purified by silica gel column chromatography (hexane:ethyl acetate gradient elution=90:10 to 50:50) to obtain 6-cyclopropyl-3-((2-(difluoromethoxy)-3-(3,6-dihydro-2H-pyran-4-yl)phenyl)amino)pyrazine-2-carboxylic acid (25 mg) as a yellow solid.

1H-NMR (CDCl3) δ: 10.40 (br s, 1H), 8.40 (s, 1H), 8.36 (d, 1H, J=7.9 Hz), 7.28-7.21 (m, 1H), 6.95 (d, 1H, J=6.6 Hz), 6.42 (t, 1H, J=74.3 Hz), 5.94 (s, 1H), 4.31 (d, 2H, J=2.6 Hz), 3.91 (t, 2H, J=5.3 Hz), 2.50 (s, 2H), 2.13-2.05 (m, 1H), 1.12-0.94 (m, 4H).

LCMS (Method A)
MS (ESI m/z): 404 (M+H)
RT (min): 1.65

Example 15

The compound C was synthesized from the compounds A and B in the same manner as in Example 1.

TABLE 5
| Example No. | A | B | C | LCMS Method | RT (min) | MS (M + H) | NMR |
|---|---|---|---|---|---|---|---|
| 15-1 | 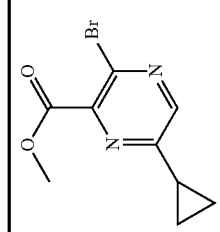 | 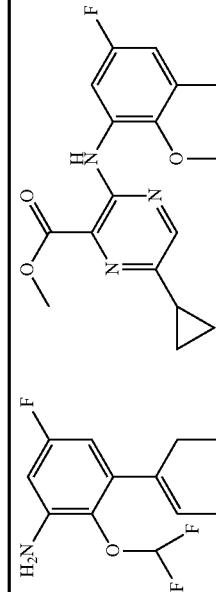 | 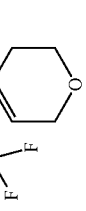 | A | 1.91 | 436 | — |
| 15-2 | 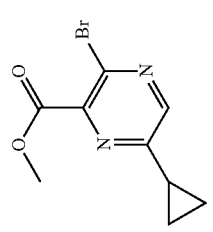 | 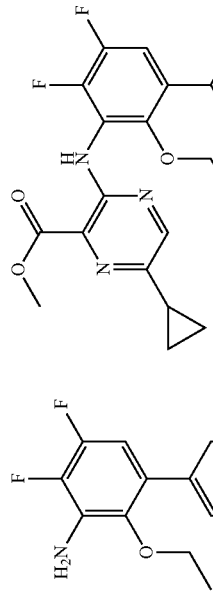 | 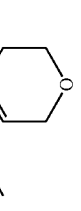 | A | 2.06 | 432 | — |
| 15-3 | 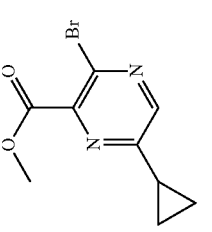 | 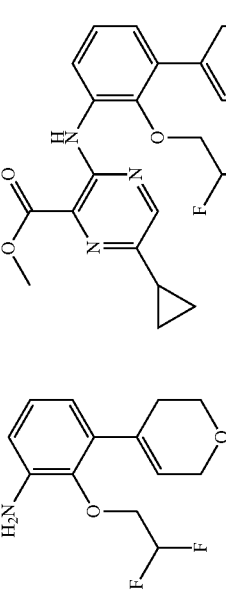 | 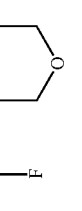 | A | 1.89 | 432 | — |

TABLE 5-continued

| Example No. | A | B | C | LCMS Method | RT (min) | MS (M+H) | NMR |
|---|---|---|---|---|---|---|---|
| 15-4 | | | | A | 1.91 | 384 | — |
| 15-5 | | | | A | 2.04 | 414 | — |
| 15-6 | | | | A | 1.97 | 464 | — |

TABLE 5-continued

| Example No. | A | B | C | LCMS Method | RT (min) | MS (M+H) | NMR |
|---|---|---|---|---|---|---|---|
| 15-7 | | | | A | 2.00 | 500 | — |
| 15-8 | | | | A | 2.03 | 464 | — |
| 15-9 | | | | A | 1.88 | 380 | — |

TABLE 5-continued
| Example No. | A | B | C | LCMS Method | RT (min) | MS (M + H) | NMR |
|---|---|---|---|---|---|---|---|
| 15-10 | 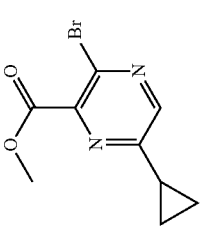 | 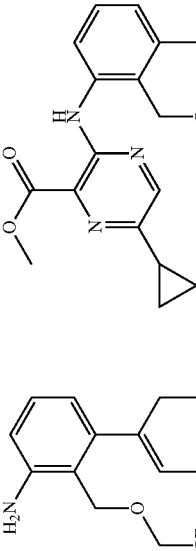 |  | A | 1.91 | 484 | — |
| 15-11 | 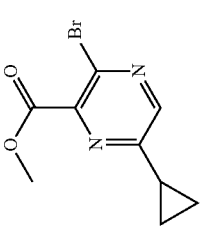 | 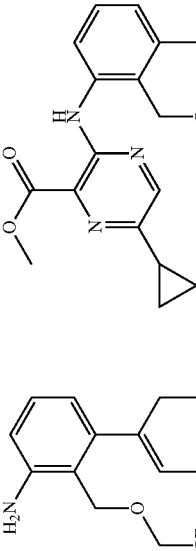 |  | A | 2.00 | 484 | — |
| 15-12 | 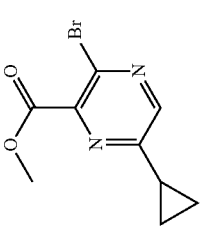 | 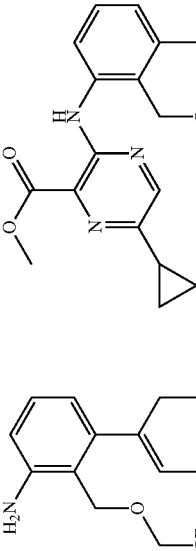 |  | A | 1.87 | 394 | — |

TABLE 5-continued
| Example No. | A | B | C | LCMS Method | RT (min) | MS (M + H) | NMR |
|---|---|---|---|---|---|---|---|
| 15-13 | | | | A | 1.84 | 396 | — |
| 15-14 | | | | A | 1.97 | 402 | — |
| 15-15 | | | | A | 1.84 | 450 | — |
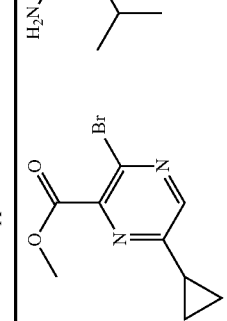
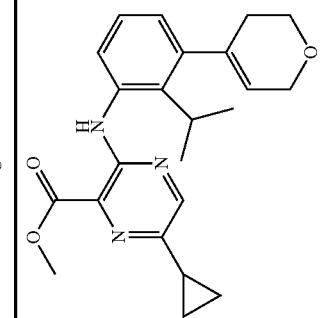
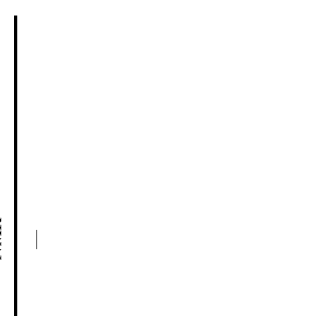
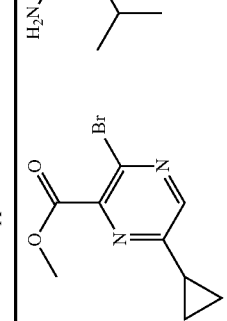
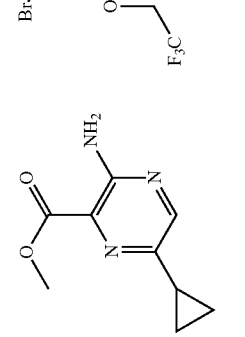
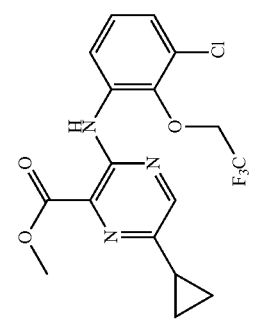
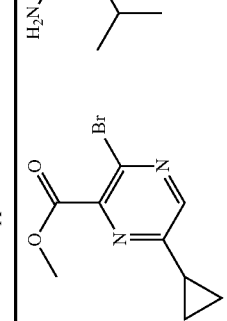
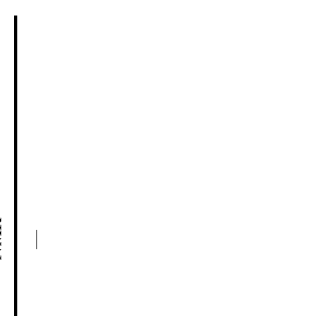
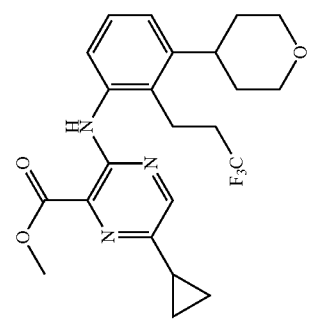

TABLE 5-continued
| Example No. | A | B | C | LCMS Method | RT (min) | MS (M + H) | NMR |
|---|---|---|---|---|---|---|---|
| 15-16 | 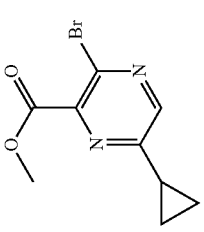 | 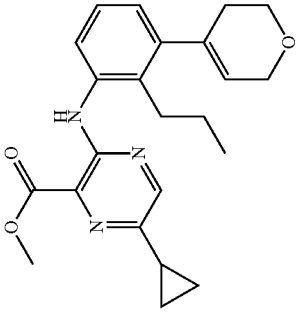 | 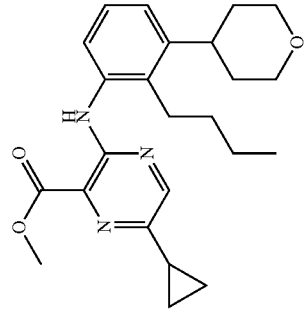 | A | 1.98 | 394 | — |
| 15-17 | 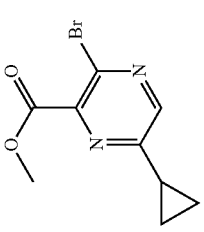 | 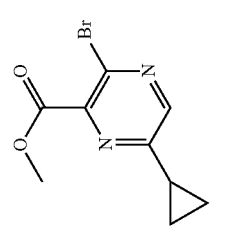 | 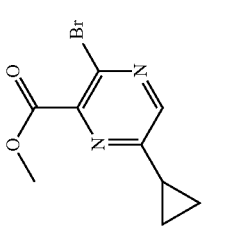 | A | 2.02 | 410 | — |
| 15-18 | 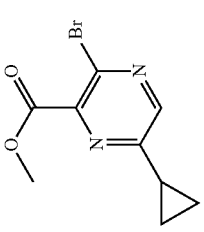 | 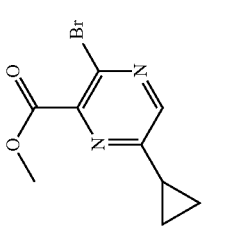 | 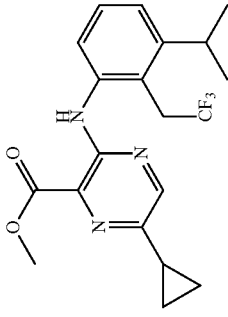 | B | 4.57 | 436 | — |

TABLE 5-continued
| Example No. | A | B | C | LCMS Method | RT (min) | MS (M + H) | NMR |
|---|---|---|---|---|---|---|---|
| 15-19 |  | 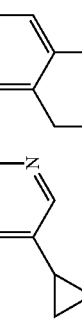 |  | B | 4.29 | 400 | — |
| 15-20 |  | 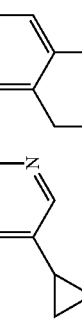 |  | — | — | — | 1H-NMR (CDCl3) δ : 10.70 (br s, 1H, 8.48 (dd, 1H, J = 8.0, 1.6 Hz), 8.22 (s, 1H), 7.09 (t, 1H, J = 8.0 Hz), 6.85 (dd, 1H, J = 8.0, 1.6 Hz), 5.98-5.96 (m, 1H), 4.33 (q, 2H, J = 2.8 Hz), 4.02 (s, 3H), 3.93 (t, 2H, J = 5.6 Hz), 3.82 (s, 3H), 2.59-2.56 (m, 2H), 2.13-2.07 (m, 1H), 1.05-0.94 (m, 4H). |
| 15-21 |  | 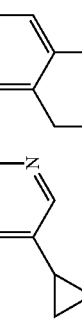 |  | B | 5.17 | 396 | — |

TABLE 5-continued

| Example No. | A | B | C | LCMS Method | RT (min) | MS (M + H) | NMR |
|---|---|---|---|---|---|---|---|
| 15-22 | | | | — | — | — | 1H-NMR (CDCl3) δ : 10.29 (bd, 1H, J = 3.2 Hz), 8.31 (dt, 1H, J = 7.8, 1.8 Hz), 8.21 (s, 1H), 7.10 (dt, 1H, J = 8.0, 0.8 Hz), 8.94 (dt, 1H, J = 7.8, 1.8 Hz), 6.08-8.05 (m, 1H), 4.33 (q, 2H, J = 2.8 Hz), 4.02 (s, 3H), 3.93 (t, 2H, J = 5.6 Hz), 2.56-2.53 (m, 2H), 2.12-2.07 (m, 1H), 1.05-0.95 (m, 4H). |
| 15-23 | | | | B | 5.27 | 440 | — |
| 15-24 | | | | B | 4.83 | 396 | — |

TABLE 5-continued
| Example No. | A | B | C | LCMS Method | RT (min) | MS (M + H) | NMR |
|---|---|---|---|---|---|---|---|
| 15-25 | 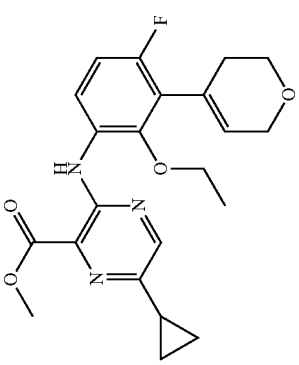 | 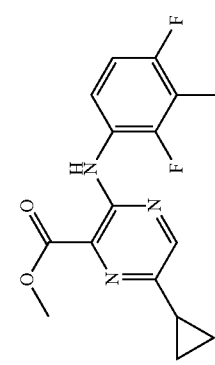 | 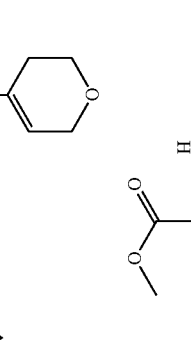 | — | — | — | 1H-NMR (CDCl3) δ : 10.51 (br s, 1H), 8.37 (dd, 1H, J = 9.2, 6.0 Hz), 8.19 (s, 1H), 6.85 (t, 1H, J = 9.2 Hz), 5.90 (m, 1H), 4.34 (q, 2H, J = 2.8 Hz), 4.01 (s, 3H), 3.98 (q, 2H, J = 7.2 Hz), 3.94 (t, 2H, J = 5.6 Hz), 2.50-2.48 (m, 2H), 2.12-2.06 (m, 1H), 1.45 (t, 3H, J = 7.2 Hz), 1.04-0.96 (m, 4H). |
| 15-26 | 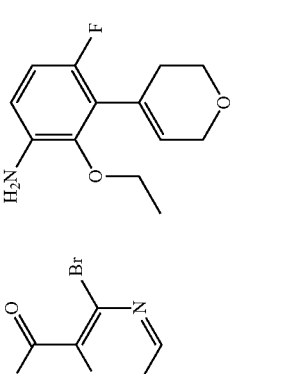 | 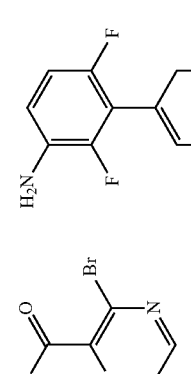 | 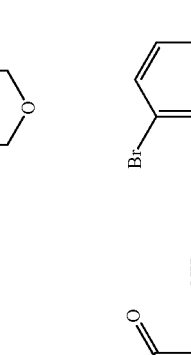 | — | — | — | 1H-NMR (CDCl3) δ : 10.09 (bd, 1H, J = 2.4 Hz), 8.18 (s, 1H), 8.18 (dt, 1H, J = 9.0, 5.6 Hz), 6.89 (dt, 1H, J = 9.2, 2.0 Hz), 5.92 (br s, 1H), 4.33 (q, 2H, J = 2.8 Hz), 4.01 (s, 3H), 3.93 (t, 2H, J = 5.2 Hz), 2.46-2.45 (m, 2H), 2.11-2.06 (m, 1H), 1.05-0.97 (m, 4H). |
| 15-27 |  |  | 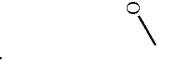 | A | 1.82 | 412 | — |

TABLE 5-continued
| Example No. | A | B | C | LCMS Method | LCMS RT (min) | LCMS MS (M + H) | NMR |
|---|---|---|---|---|---|---|---|
| 15-28 | 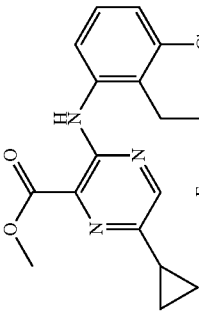 | 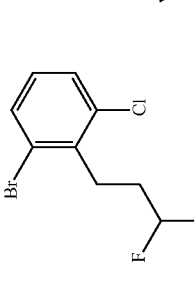 | 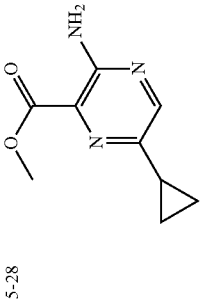 | B | 5.17 | 382 | — |
| 15-29 | 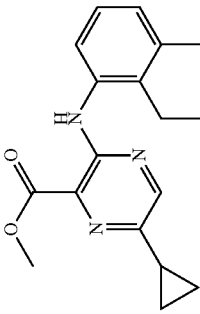 | 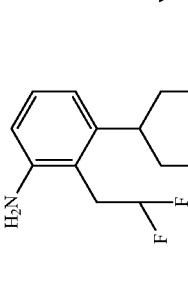 | 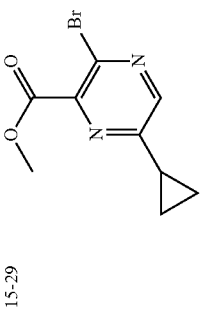 | B | 4.32 | 418 | — |
| 15-30 | 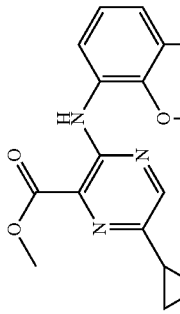 | 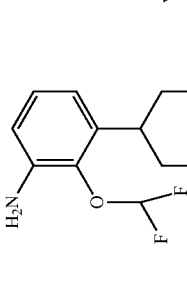 | 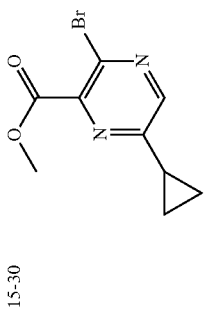 | A | 1.76 | 420 | — |

TABLE 5-continued

| Example No. | A | B | C | LCMS Method | RT (min) | MS (M + H) | NMR |
|---|---|---|---|---|---|---|---|
| 15-31 | | | | A | 1.93 | 452 | — |
| 15-32 | | | | A | 1.78 | 438 | — |
| 15-33 | | | | A | 1.64 | 424 | — |

Example 16

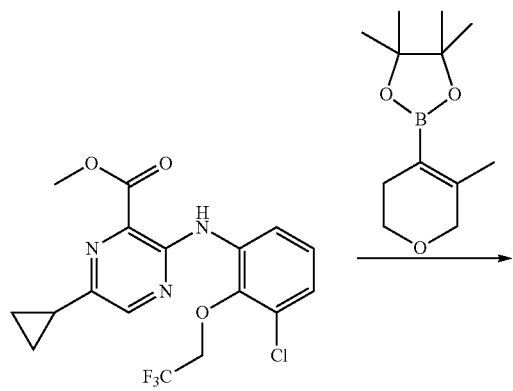

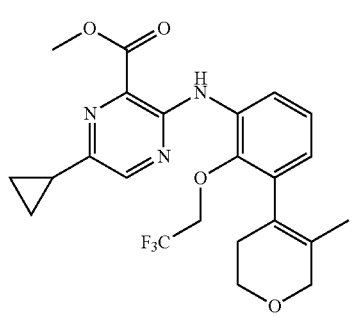 [SMILES: COC(=O)c1nc(C2CC2)cnc1Nc1cccc(C2=C(C)COCC2)c1OCC(F)(F)F]

Methyl 6-cyclopropyl-3-((3-(5-methyl-3,6-dihydro-2H-pyran-4-yl)-2-(2,2,2-trifluoroethoxy)phenyl)amino) pyrazine-2-carboxylate was synthesized in the same manner as in Reference Example 2, by changing 3,6-dihydro-2H-pyran-4-boronic acid pinacol ester to 4,4,5,5-tetramethyl-2-(5-methyl-3,6-dihydro-2H-pyran-4-yl)-1,3,2-dioxaborolane.

LCMS (Method A)
MS (ESI m/z): 464 (M+H)
RT (min): 1.96

Example 17

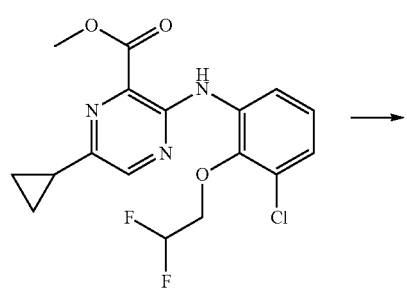

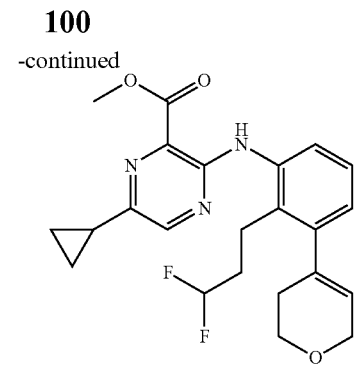

Methyl 6-cyclopropyl-3-((2-(3,3-difluoropropyl)-3-(3,6-dihydro-2H-pyran-4-yl)phenyl)amino)pyrazin e-2-carboxylate was synthesized in the same manner as in Reference Example 2, by changing 1,2-dimethoxyethane to toluene.

LCMS (Method B)
MS (ESI m/z): 430 (M+H)
RT (min): 4.79

Example 18

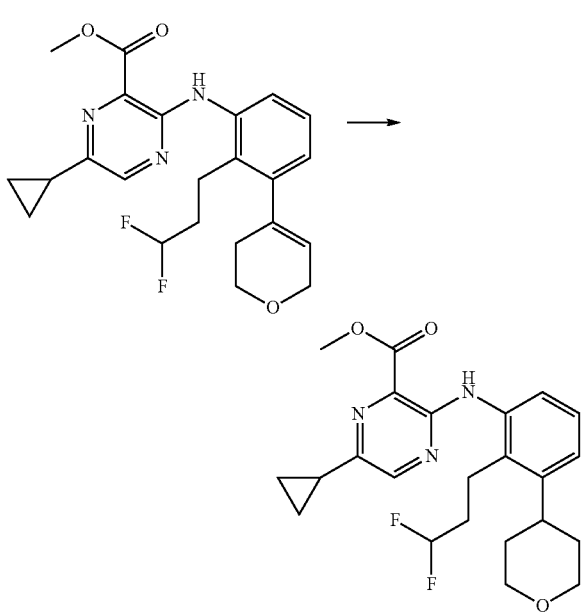

Methyl 6-cyclopropyl-3-((2-(3,3-difluoropropyl)-3-(tetrahydro-2H-pyran-4-yl)phenyl)amino)pyrazine-2-carboxylate was synthesized in the same manner as in Reference Example 5.

LCMS (Method B)
MS (ESI m/z): 432 (M+H)
RT (min): 4.60

Example 19

The compound B was synthesized from the compound A in the same manner as in Example 2.

TABLE 6

| Example No. | A | B | LCMS Method | RT (min) | MS (M + H) | NMR |
|---|---|---|---|---|---|---|
| 19-1 | | | A | 1.73 | 422 | 1H-NMR (CDCl3) δ : 10.62 (s, 1H), 8.45 (s, 1H), 8.37 (dd, 1H, J = 10.9, 3.0 Hz), 6.66-6.62 (m, 1H), 6.41 (t, 1H, J = 142.7 Hz), 5.98 (s, 1H), 4.31 (d, 2H), J = 2.6 Hz), 3.91 (t, 2H, J = 5.6 Hz), 2.47 (s, 2H), 2.20-2.03 (m, 1H), 1.19-0.89 (m, 4H). |
| 19-2 | | | A | 1.87 | 418 | 1H-NMR (DMSO-D6) δ : 10.91 (br s, 1H), 8.59 (dd, 1H, J = 13.9, 6.6 Hz), 8.47 (s, 1H), 5.97 (s, 1H), 4.33-4.17 (m, 2H), 3.98-3.79 (m, 4H), 2.37 (br s, 2H), 2.21-2.12 (m, 1H), 1.38 (t, 3H, J = 6.9 Hz), 1.06-0.90 (m, 4H). |
| 19-3 | | | A | 1.73 | 418 | 1H-NMR (DMSO-D6) δ : 10.74 (br s, 1H), 8.47-8.41 (m, 2H), 7.14 (t, 1H, J = 7.9 Hz), 586 (dd. 1H, J = 7.9, 1.3 Hz), 6.35 (tt, 1H, J = 55.2, 4.0 Hz), 5.98 (s, 1H), 4.22-4.22 (m, 2H), 4.09 (td, 2H, J = 13.5, 4.0 Hz), 3.83 (t, 2H, J = 5.3 Hz), 2.43 (br s, 2H), 2.20-2.12 (m, 1H), 0.99-0.91 (m, 4H). |

TABLE 6-continued

| Example No. | A | B | LCMS Method | RT (min) | MS (M + H) | NMR |
|---|---|---|---|---|---|---|
| 19-4 | | | A | 1.72 | 370 | 1H-NMR (CDCl3) δ : 9.92 (br s, 1H), 8.41 (s, 1H), 7.94 (dd, 1H, J = 11.2, 2.6 Hz), 6.84 (dd, 1H, J = 8.9, 3.0 Hz), 5.65 (s, 1H), 4.30 (t, 2H, J = 3.0 Hz), 3.93 (t, 2H, J = 5.3 Hz), 2.37-2.29 (m, 2H), 2.28 (s, 3H), 2.14-2.05 (m, 1H), 1.13-0.94 (m, 4H). |
| 19-5 | | | A | 1.85 | 400 | 1H-NMR (MeOD) δ : 8.49-8.40 (m, 1H), 8.35 (s, 1H), 6.55-6.51 (m, 1H), 6.01 (s, 1H), 4.29 (s, 2H), 3.99-3.83 (m, 4H), 2.54 (s, 2H), 2.21-2.08 (m, 1H), 1.43 (t, 3H, J = 6.9 Hz), 1.09-0.82 (m, 4H). |
| 19-6 | | | A | 1.79 | 450 | 1H-NMR (DMSO-D6) δ : 13.45 (br s, 1H), 10.53 (br s, 1H), 8.42 (s, 1H), 8.34 (dd, 1H, J = 8.6, 1.3 Hz), 7.15 (dd, 1H, J = 8.6, 7.9 Hz), 6.89 (dd, 1H, J = 7.9, 1.3 Hz), 5.96 (br s, 1H), 4.71-4.58 (m, 1H), 4.22-4.17 (m, 2H), 3.82 (t, 2H, J = 5.3 Hz), 2.44 (br s, 2H), 2.21-2.10 (m, 1H), 1.28 (d, 3H, J = 5.9 Hz), 0.99-0.90 (m, 4H). |

TABLE 6-continued

| Example No. | A | B | LCMS Method | RT (min) | MS (M + H) | NMR |
|---|---|---|---|---|---|---|
| 19-7 | | | A | 1.82 | 4.86 | 1H-NMR (DMSO-D6) δ : 13.45 (br s, 1H), 10.40 (br s, 1H), 8.41 (s, 1H), 8.27-8.22 (m, 1H), 7.21-7.14 (m, 1H), 694-6.89 (m, 1H), 5.95 (br s, 1H), 4.44 (t, 2H, J = 14.2 Hz), 4.21-4.15 (m, 2H), 3.81 (t, 2H, J = 5.3 Hz), 2.40 (br s, 2H), 2.22-2.10 (m, 1H), 0.95-0.93 (m, 2H). |
| 19-8 | | | A | 1.87 | 450 | 1H-NMR (DMSO-D6) δ : 13.39 (br s, 1H), 10.40 (br s, 1H), 8.52 (dd, 1H, J = 8.3, 1.3 Hz), 8.45 (s, 1H), 7.13 (dd, 1H, J = 8.3, 7.9 Hz), 6.84 (dd, 1H, J = 7.9, 1.3 Hz), 5.97 (br s, 1H), 4.23-4.17 (m, 2H), 3.97 (t, 2H, J = 5.9 Hz), 3.82 (t, 2H, J = 5.3 Hz), 2.96-2.84 (m, 2H), 2.42 (br s, 2H), 2.23-2.12 (m, 1H), 1.00-0.91 (m, 4H). |
| 19-9 | | | A | 1.70 | 355 | 1H-NMR (CDCl3) δ : 9.77 (s, 1H), 8.34 (s, 1H), 7.80 (d, 1H, J = 7.9 Hz), 7.21 (t, 1H, J = 7.9 Hz), 6.93 (d, 1H, J = 7.9 Hz), 5.63 (s, 1H), 4.30 (q, 2H, J = 2.6 Hz), 3.93 (t, 2H, J = 5.3 Hz), 2.73 (q, 2H, J = 7.5 Hz), 2.42-2.30 (m, 2H), 2.08-2.03 (m, 1H), 1.20 (t, 3H, J = 7.7 Hz), 1.07-0.96 (m, 4H). |

TABLE 6-continued

| Example No. | A | B | LCMS Method | RT (min) | MS (M + H) | NMR |
|---|---|---|---|---|---|---|
| 19-10 | | | A | 1.75 | 450 | 1H-NMR (CDCl3) δ : 10.19 (s, 1H), 8.37 (s, 1H), 8.00 (d, 1H, J = 7.9 Hz), 7.35 (t, 1H, J = 7.9 Hz), 6.98 (d, 1H, J = 6.6 Hz), 5.75 (s, 1H), 4.73 (s, 2H), 4.32-4.28 (m, 2H), 4.13 (q, 2H, J = 9.0 Hz), 3.93 (t, 2H, J = 5.6 Hz), 2.43-2.36 (m, 2H), 2.12-2.03 (m, 1H), 1.13-0.94 (m, 4H). |
| 19-11 | | | A | 1.83 | 450 | 1H-NMR (DMSO-D6) δ : 13.46 (br s, 1H), 10.56 (br s, 1H), 8.41 (s, 1H), 8.35 (dd, 1H, J = 8.3, 1.7 Hz), 7.15 (dd, 1H, J = 8.3, 7.6 Hz), 6.88 (dd, 1H, J = 7.6, 1.7 Hz), 6.02 (br s, 1H), 4.75-4.64 (m, 1H), 4.39-4.17 (m, 2H), 3.77 (t, 2H, J = 5.3 Hz), 2.30-2.20 (m, 2H), 2.19-2.11 (m, 1H), 1.29 (d, 3H, J = 6.6 Hz), 0.99-0.90 (m, 4H). |
| 19-12 | | | A | 1.70 | 380 | 1H-NMR (DMSO-D6) δ : 10.32 (s, 1H), 8.34 (s, 1H), 7.94 (d, 1H, J = 7.9 Hz), 7.19 (t, 1H, J = 7.9 Hz), 6.99 (d, 1H, J = 7.9 Hz), 4.02-3.92 (m, 2H), 3.53-3.40 (m, 2H), 3.32-3.26 (m, 1H), 2.18-2.07 (m, 1H), 1.78-1.56 (m, 5H), 1.18-1.10 (m, 2H), 0.93 (d, 4H, J = 6.6 Hz), 0.45 (d, 2H, J = 4.6 Hz). |

TABLE 6-continued

| Example No. | A | B | LCMS Method | RT (min) | MS (M + H) | NMR |
|---|---|---|---|---|---|---|
| 19-13 | | | A | 1.65 | 382 | 1H-NMR (DMSO-D6) δ : 9.50 (br s, 1H), 8.23 (s, 1H), 7.25-7.10 (m, 3H), 4.01-3.91 (m, 2H), 3.56-3.43 (m, 2H), 3.20-3.05 (m, 1H), 2.14-2.02 (m, 1H), 1.84-1.54 (m, 5H), 1.27 (d, 6H, J = 7.3 Hz), 0.97-0.88 (m, 4H). |
| 19-14 | | | A | 1.81 | 450 | 1H-NMR (DMSO-D6) δ : 10.67 (br s, 1H), 8.43-8.37 (m, 2H), 7.21-7.13 (m, 1H), 6.83-6.78 (m, 1H), 4.43-4.29 (m, 2H), 4.03 (s, 2H), 3.80 (br s, 2H), 2.37-2.25 (m, 2H), 2.20-2.08 (m, 1H), 1.44 (s, 3H), 1.00-0.90 (m, 4H). |
| 19-15 | | | A | 1.68 | 436 | 1H-NMR (CDCl3) δ : 9.56 (s, 1H), 8.29 (s, 1H), 7.48 (d, 1H, J = 7.3 Hz), 7.31 (t, 1H, 7.6 Hz), 7.20 (d, 1H, J = 7.3 Hz), 4.14-4.05 (m, 2H), 3.56 (t, 2H, J = 11.2 Hz), 3.03-2.93 (m, 3H), 2.37-2.24 (m, 2H), 2.09-2.01 (m, 1H), 1.99-1.82 (m, 2H), 1.73-1.62 (m, 2H), 1.08-0.86 (m, 4H). |

TABLE 6-continued

| Example No. | A | B | LCMS Method | RT (min) | MS (M + H) | NMR |
|---|---|---|---|---|---|---|
| 19-16 | [structure] | [structure] | A | 1.80 | 380 | 1H-NMR (CDCl3) δ : 9.78 (s, 1H), 8.33 (s, 1H), 7.82 (d, 1H, J = 7.9 Hz), 7.20 (t, 1H, J = 7.9 Hz), 6.92 (d, 1H, J = 7.3 Hz), 5.62 (s, 1H), 4.30 (q, 2H, J = 2.6 Hz), 3.93 (t, 2H, J = 5.3 Hz), 2.69-2.61 (m, 2H), 2.35 (s, 2H), 2.10-2.01 (m, 1H), 1.63-1.48 (m, 2H), 1.09-0.91 (m, 4H), 1.00 (t, 3H, J = 7.3 Hz). |
| 19-17 | [structure] | [structure] | A | 1.84 | 396 | 1H-NMR (CDCl3) δ : 9.67 (s, 1H), 8.31 (s, 1H), 7.62 (d, 1H, J = 7.3 Hz), 7.23 (d, 1H, J = 7.9 Hz), 7.13 (d, 1H, J = 7.3 Hz), 4.11 (dd, 2H, J = 11.9, 4.0 Hz), 3.56 (t, 2H, J = 11.2 Hz), 3.09-2.96 (m, 1H), 2.73 (t, 2H, J = 7.6 Hz), 2.09-2.00 (m, 1H), 1.97-1.80 (m, 2H), 1.75-1.37 (m, 6H), 1.11-0.79 (m, 7H). |
| 19-18 | [structure] | [structure] | B | 4.15 | 422 | 1H-NMR (DMSO-D6) δ : 13.35 (br s, 1H), 9.92 (s, 1H), 8.26 (s, 1H), 7.55 (dd, 1H, J = 8.0, 0.8 Hz), 7.35 (t, 1H, J = 8.0 Hz), 7.23 (dd, 1H, J = 7.8, 0.8 Hz), 3.94 (dd, 2H, J = 11.2, 3.6 Hz), 3.84 (q, 2H, J = 11.2 Hz), 3.46 (t, 2H, J = 11.6 Hz), 3.12-3.06 (m, 1H), 2.14-2.07 (m, 1H), 1.74 (dq, 2H, J = 12.4, 3.6 Hz), 1.58-1.55 (m, 2H), 0.96-0.89 (m, 4H). |

TABLE 6-continued

| Example No. | A | B | LCMS Method | RT (min) | MS (M + H) | NMR |
|---|---|---|---|---|---|---|
| 19-19 | | | B | 3.86 | 386 | 1H-NMR (DMSO-D6) δ : 11.02 (br s, 1H), 8.13 (br s, 1H), 7.78 (d, 1H, J = 8.0 Hz), 7.21 (t, 1H, J = 8.0 Hz), 7.04 (d, 1H, J = 8.0 Hz), 4.56 (dt, 2H, J = 47.3, 6.4 Hz), 3.96-3.93 (m, 2H), 3.48 (t, 2H, J = 10.8 Hz), 3.24-3.01 (m, 3H), 2.08 (br s, 1H), 1.77-1.67 (m, 2H), 1.51-1.58 (m, 2H), 0.88 (m, 4H). |
| 19-20 | | | B | 4.37 | 368 | 1H-NMR (DMSO-D6) δ : 13.40 (br s, 1H), 10.86 (s, 1H), 8.47 (dd, 1H, J = 8.4, 1.6 Hz), 8.45 (s, 1H), 7.08 (t, 1H, J = 8.0 Hz), 6.84 (dd, 1H, J = 7.6 1.6 Hz), 5.98 (m, 1H), 4.23-4.22 (m, 2H), 3.83 (t, 2H, J = 5.6 Hz), 3.69 (s, 3H), 2.45-2.44 (m, 2H), 2.19-2.13 (m, 1H), 0.99 (m, 4H). |
| 19-21 | | | B | 4.68 | 382 | 1H-NMR (DMSO-D6) δ : 12.30 (br s, 1H), 11.15 (br s, 1H), 8.49 (d, 1H, J = 8.4 Hz), 8.36 (br s, 1H), 7.06 (t, 1H, J = 8.0 Hz), 6.80 (dd, 1H, J = 7.6, 1.2 Hz), 5.97 (br s, 1H), 4.22 (m, 2H), 3.66-3.80 (m, 4H), 2.45 (m, 2H), 2.14 (br s, 1H), 1.37 (t, 3H, J = 6.8 Hz), 0.92 (br s, 4H). |

TABLE 6-continued

| Example No. | A | B | LCMS Method | RT (min) | MS (M+H) | NMR |
|---|---|---|---|---|---|---|
| 19-22 | | | B | 4.30 | 356 | 1H-NMR (DMSO-D6) δ : 10.64 (br s, 1H), 8.42 (s, 1H), 8.34 (dt, 1H, J = 7.8, 1.6 Hz), 7.16 (t, 1H, J = 7.6 Hz), 7.00 (dt, 1H, J = 7.6, 1.2 Hz), 6.09 (br s, 1H), 4.23 (q, 2H, J = 2.8 Hz), 3.82 (t, 2H, J = 5.6 Hz), 2.44 (m, 2H), 2.19-2.12 (m, 1H), 0.99-0.92 (m, 4H). |
| 19-23 | | | B | 4.78 | 426 | 1H-NMR (DMSO-D6) δ : 10.71 (br s, 1H), 8.35 (s, 1H), 8.31 (d, 1H, J = 9.2 Hz), 6.75 (d, 1H, J = 9.2 Hz), 5.69 (s, 1H), 4.20 (d, 2H, J = 2.4 Hz), 3.96 (q, 2H, J = 6.8 Hz), 3.84-3.79 (m, 4H), 2.33 (m, 2H), 2.12 (m, 1H), 1.33 (t, 3H, J = 6.8 Hz), 1.29 (t, 3H, J = 6.8 Hz), 0.91 (m, 4H). |
| 19-24 | | | B | 4.33 | 382 | 1H-NMR (DMSO-D6) δ : 10.12 (br s, 1H), 8.32 (s, 1H), 7.50 (dd, 1H, J = 8.8, 2.8 Hz), 7.33 (d, 1H, J = 2.8 Hz), 6.95 (d, 1H, J = 8.8 Hz), 5.90 (m, 1H), 4.19 (q, 2H, J = 2.4 Hz), 4.06-3.97 (m, 2H), 3.77 (t, 2H, J = 5.6 Hz), 2.44 (m, 2H), 2.14-2.07 (m, 1H), 1.32 (t, 3H, J = 6.8 Hz), 0.93-0.91 (m, 4H). |

TABLE 6-continued

| Example No. | A | B | LCMS Method | RT (min) | MS (M + H) | NMR |
|---|---|---|---|---|---|---|
| 19-25 | | | B | 4.70 | 400 | 1H-NMR (DMSO-D6) δ : 12.46-12.26 (m, 1H), 8.45 (m, 1H), 7.97 (s, 1H), 6.92 (t, 1H, J = 9.2 Hz), 5.88 (s, 1H), 4.22 (m, 2H), 3.88 (q, 2H, J = 6.8 Hz), 3.83 (t, 2H, J = 5.2 Hz), 2.35 (m, 2H), 2.08 (br s, 1H), 1.36 (t, 3H, J = 6.8 Hz), 0.94-0.55 (m, 4H). |
| 19-26 | | | B | 4.33 | 374 | 1H-NMR (DMSO-D6) δ : 10.82 (br s, 1H), 8.33-8.28 (m, 2H), 7.10 (dt, 1H, J = 9.2, 1.6 Hz), 5.96 (s, 1H), 4.23 (q, 2H, J = 2.8 Hz), 3.83 (t, 2H, J = 5.6 Hz), 2.33 (m, 2H), 2.14 (m, 1H), 0.96-0.92 (m, 4H). |
| 19-27 | | | A | 1.66 | 398 | 1H-NMR (CDCl3) δ : 9.75 (s, 1H), 8.34 (s, 1H), 7.81 (d, 1H, J = 8.6 Hz), 7.22 (d, 1H, J = 7.3 Hz), 6.95 (d, 1H, J = 7.9 Hz), 5.84 (s, 1H), 4.48 (dt, 2H, J = 47.3, 5.8 Hz), 4.29 (q, 2H, J = 2.6 Hz), 3.93 (t, 2H, J = 5.3 Hz), 2.87-2.79 (m, 2H), 2.36 (s, 2H), 2.10-1.89 (m, 3H), 1.12-0.92 (m, 4H). |

TABLE 6-continued

| Example No. | A | B | LCMS Method | RT (min) | MS (M + H) | NMR |
|---|---|---|---|---|---|---|
| 19-28 | | | B | 4.19 | 418 | 1H-NMR (DMSO-D6) δ : 9.96 (br s, 1H), 8.27 (s, 1H), 7.60 (d, 1H, J = 8.1 Hz), 7.22 (t, 1H, J = 7.8 Hz), 7.11 (d, 1H, J = 7.1 Hz), 6.14 (tt, 1H, J = 56.6, 3.3 Hz), 3.97 (dd, 2J, J = 11.1, 3.3 Hz), 3.47 (t, 2H, J = 10.9 Hz), 3.04-2.94 (m, 1H), 2.87-2.77 (m, 2H), 2.16-1.89 (m, 3H), 1.81-1.67 (m, 2H), 1.64-1.57 (m, 4H), 0.96-0.88 (m, 4H). |
| 19-29 | | | B | 3.92 | 404 | 1H-NMR (DMSO-D6) δ : 13.28 (br s, 1H), 9.87 (s, 1H), 8.26 (s, 1H), 7.54 (d, 1H, J = 7.1 Hz), 7.30 (t, 1H, J = 7.8 Hz), 7.18 (d, 1H, J = 7.3 Hz), 6.24 (tt, 1H, J = 56.4, 3.3 Hz), 3.94 (dd, 2H, J = 11.1, 3.9 Hz), 3.48 (t, 2H, J = 10.8 Hz), 3.40-3.29 (m, 2H), 3.11-3.00 (m, 1H), 2.14 2.08 (m, 1H), 1.80-1.66 (m, 2H), 1.59 (d, 2H, J = 11.2 Hz), 0.95-0.89 (m, 4H). |
| 19-30 | | | A | 1.59 | 406 | 1H-NMR (DMSO-D6) δ : 10.52 (br s, 1H), 8.40 (s, 1H), 8.23 (d, 1H, J = 7.3 Hz), 7.28 (t, 1H, J = 7.9 Hz), 7.24-6.73 (m, 2H), 4.01-3.92 (m, 2H), 3.50-3.40 (m, 2H), 3.24-3.08 (m, 1H), 2.22-2.10 (m, 1H), 1.80-1.55 (m, 4H), 1.01-0.90 (m, 4H). |

TABLE 6-continued

| Example No. | A | B | LCMS Method | RT (min) | MS (M + H) | NMR |
|---|---|---|---|---|---|---|
| 19-31 | (structure) | (structure) | A | 1.79 | 438 | 1H-NMR (CDCl3) δ : 10.97 (s, 1H), 10.32 (s, 1H), 8.40 (s, 1H), 8.30 (dd, 1H, J = 8.3, 1.5 Hz), 7.16 (t, 1H, J = 8.0 Hz), 6.93 (dd, 1H, J = 7.8, 1.5 Hz), 6.00 (s, 1H), 4.32 (q, 2H, J = 2.7 Hz), 4.24 (q, 2H, J = 8.4 Hz), 3.94 (t, 2H, J = 5.4 Hz), 3.14-3.07 (m, 1H), 2.55-2.49 (m, 2H), 1.34 (d, 6H, J = 6.8 Hz). |
| 19-32 | (structure) | (structure) | A | 1.65 | 424 | 1H-NMR (DMSO-D6) δ : 13.54 (br s, 1H), 10.65 (br s, 1H), 8.38 (s, 1H), 8.36 (d, 1H, J = 8.3 Hz), 7.17 (t, 1H, J = 8.0 Hz), 6.90 (dd, 1H, J = 7.6, 1.4 Hz), 5.97 (s, 1H), 4.43 (q, 2H, J = 8.9 Hz), 4.20 (d, 2H, J = 2.3 Hz), 3.82 (t, 2H, J = 5.3 Hz), 2.74 (q, 2H, J = 7.6 Hz), 2.45-2.38 (m, 2H), 1.24 (t, 3H, J = 7.6 Hz). |
| 19-33 | (structure) | (structure) | A | 1.51 | 410 | 1H-NMR (DMSO-D6) δ : 13.52 (br s, 1H), 10.68 (br s, 1H), 8.36-8.33 (m, 2H), 7.17 (t, 1H, J = 8.0 Hz), 6.90 (dd, 1H, J = 7.9, 1.4 Hz), 5.97 (s, 1H), 4.43 (q, 2H, J = 9.0 Hz), 4.23-4.18 (m, 2H), 3.82 (t, 2H, J = 5.3 Hz), 2.46-2.38 (m, 2H), 2.44 (s, 3H). |

Example 20

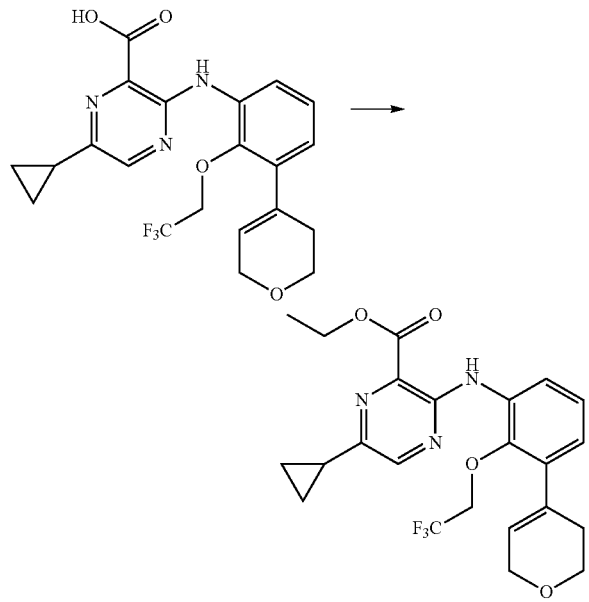

A mixture of 6-cyclopropyl-3-((3-(3,6-dihydro-2H-pyran-4-yl)-2-(2,2,2-trifluoroethoxy)phenyl)amino)pyrazine-2-carboxylic acid (25 mg), ethanol (3.0 mL), 1-(3-dimethylaminopropyl)-3-ethylcarbodiimide hydrochloride (28 mg), and 4-dimethylaminopyridine (4.0 mg) was stirred at 50° C. overnight. After cooling to room temperature, the solvent was distilled off under reduced pressure. The obtained residue was purified by silica gel column chromatography (hexane:ethyl acetate gradient elution=90:10 to 80:20) to obtain ethyl 6-cyclopropyl-3-((3-(3,6-dihydro-2H-pyran-4-yl)-2-(2,2,2-trifluoroethoxy)phenyl)amino)pyrazine-2-carboxylate (23 mg) as a yellow solid.

1H-NMR (DMSO-D6) δ: 10.24 (br s, 1H), 8.42 (s, 1H), 8.26 (dd, 1H, J=7.9, 1.6 Hz), 7.17 (t, 1H, J=7.9 Hz), 6.92 (dd, 1H, J=7.7, 1.6 Hz), 5.98 (br s, 1H), 4.46-4.34 (m, 4H), 4.23-4.19 (m, 2H), 3.82 (t, 2H, J=5.3 Hz), 2.46-2.38 (m, 2H), 2.21-2.13 (m, 1H), 1.34 (t, 3H, J=7.1 Hz), 1.01-0.95 (m, 2H), 0.91-0.85 (m, 2H).

LCMS (Method B)
MS (ESI m/z): 464 (M+H)
RT (min): 5.72

Example 21

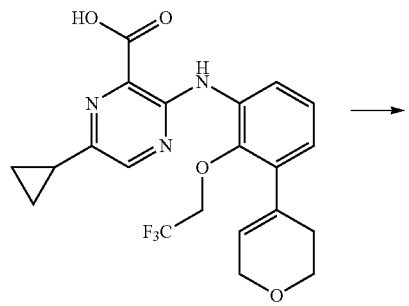

→

-continued

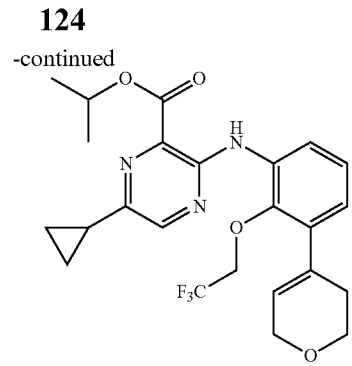

A mixture of 6-cyclopropyl-3-((3-(3,6-dihydro-2H-pyran-4-yl)-2-(2,2,2-trifluoroethoxy)phenyl)amino)pyrazine-2-carboxylic acid (25 mg), 2-propanol (3.0 mL), 1-(3-dimethylaminopropyl)-3-ethylcarbodiimide hydrochloride (28 mg), and 4-dimethylaminopyridine (4.0 mg) was stirred at 50° C. overnight. Dimethylaminopyridine (4.0 mg) was added to the mixture which was then stirred at 80° C. overnight. After cooling to room temperature, the solvent was distilled off under reduced pressure. The obtained residue was purified by silica gel column chromatography (hexane:ethyl acetate gradient elution=90:10 to 80:20) to obtain isopropyl 6-cyclopropyl-3-((3-(3,6-dihydro-2H-pyran-4-yl)-2-(2,2,2-trifluoroethoxy)phenyl)amino)pyrazine-2-carboxylate (13 mg) as a yellow solid.

1H-NMR (DMSO-D6) δ: 10.27 (s, 1H), 8.39 (s, 1H), 8.26 (dd, 1H, J=8.3, 1.5 Hz), 7.17 (t, 1H, J=7.9 Hz), 6.92 (dd, 1H, J=7.7, 1.6 Hz), 5.98 (br s, 1H), 5.21-5.13 (m, 1H), 4.42 (q, 2H, J=9.0 Hz), 4.24-4.19 (m, 2H), 3.82 (t, 2H, J=5.4 Hz), 2.45-2.39 (m, 2H), 2.20-2.12 (m, 1H), 1.35 (d, 6H, J=6.1 Hz), 1.01-0.94 (m, 2H), 0.91-0.85 (m, 2H).

LCMS (Method B)
MS (ESI m/z): 478 (M+H)
RT (min): 5.89

TEST EXAMPLE

Test Example 1: Enzyme Reaction Inhibition Test

The DHODH enzyme assay was carried out with reference to "Benjamin Bader, Wolfgang Knecht, Markus Fries, and Monika Loffler. Expression, Purification, and Characterization of Histidine-Tagged Rat and Human Flavoenzyme Dihydroorotate Dehydrogenase. Protein Expression and Purification, 1998, 13, 414-422."

The DHODH activity was evaluated using an enzyme assay system that is coupled with an assay in which a blue coloring agent 2,6-dichlorophenol indophenol (DCIP, available from MP Biomedicals, LLC, MP150118) is quenched. Purified recombinant human DHODH (DHODH, 31-395 aa, Human, His tag, E. coli, ATGP1615) was purchased from ATGen Co. Ltd. The enzyme assay was carried out in a 384-well plate using a buffer solution containing 100 mmol/L Hepes (available from Dojindo Laboratories, 342-01375), 400 mmol/L NaCl (available from FUJIFILM Wako Pure Chemical Corporation, 191-01665), 10% Glycerol (available from FUJIFILM Wako Pure Chemical Corporation, 075-00616), 0.05% Triton X-100 (available from Sigma-Aldrich Co., LLC, T8787-100ML), 0.2 mmol/L Ubiquinone-10 (available from FUJIFILM Wako Pure Chemical Corporation, 216-00761), 0.1 mmol/L DHO (L-dihydroorotic acid, available from Sigma-Aldrich Co., LLC, D7128), 0.5% DMSO (dimethylsulfoxide, available from FUJIFILM Wako Pure Chemical Corporation, 047-

29353), 0.175 µg/mL DHODH, and 0.12 mmol/L DCIP and having a pH adjusted to 8.0 by adding 5 mol/L potassium hydroxide (available from FUJIFILM Wako Pure Chemical Corporation, 168-21815). A test compound with a predetermined concentration was added using Biomek NX (available from Beckman Coulter Inc.), and the enzymatic reaction was started by adding the substrate. The enzyme activity was assessed by measuring the decrease in DCIP absorbance (600 nm) for 50 minutes using an EnVision plate-reading spectrophotometer (available from PerkinElmer, Inc.).

The enzyme reaction inhibition rate at each test compound concentration was determined, and the 50% enzyme reaction inhibition concentration [IC50 (nmol/L)] was calculated using XLfit.

Enzyme reaction inhibition rate (%)=(amount of luminescence in test compound-added well)/(amount of luminescence in DMSO-added well)×100

The results are shown in Table 7. The abbreviations in the table have the following meanings.
A: IC50 value<10 nmol/L
B: 10 nmol/L≤IC50 value<100 nmol/L
C: 100 nmol/L≤IC50 value As shown in Table 7, each test compound showed an excellent enzyme reaction inhibitory effect.

Test Example 2: Cell Growth Test

The cell growth test was carried out using the human myeloid leukemia cell line HL60 (available from ATCC, CRL-240). As a culture medium of HL60 cells, RPMI 1640 (available from FUJIFILM Wako Pure Chemical Corporation, 189-02025) supplemented with 10% fetal bovine serum (available from Thermo Fisher Scientific, Inc., 10437-028), and 1% penicillin-streptomycin (10,000 U/mL, available from Thermo Fisher Scientific, Inc., 15140-122) was used. HL60 cells were seeded on a 384-well plate (available from Corning Inc., 4588) at a cell density of 1×10$^3$ cells/20 µL/well. After culturing overnight, 5 µL of the test compound having a predetermined concentration was added, and 3 days later, 25 µL of Cell Titer Glo (registered trademark) Luminescent Cell Viability Assay (available from Promega Corporation, G7573) was added, and then the amount of luminescence was measured using an EnVision plate reader (available from PerkinElmer, Inc.). Since the amount of luminescence is proportional to the intracellular concentration of adenosine triphosphate (ATP), the amount of luminescence was used as an indicator of the number of viable cells. The growth inhibitory concentration for each test compound concentration was calculated by the following expression.

The growth inhibition rate at each test compound concentration was determined, and the 50% growth inhibitory concentration [GI50 (nmol/L)] was calculated using XLfit.

Growth inhibition rate (%)=(amount of luminescence in test compound-added well)/(amount of luminescence in DMSO-added well)×100

The results are shown in Table 7. The abbreviations in the table have the following meanings.
A: GI50 value<100 nmol/L
B: 100 nmol/L≤GI50 value<1,000 nmol/L
C: 1,000 nmol/L≤GI50 value As shown in Table 7, each test compound showed an excellent cell growth inhibition rate.

TABLE 7

| Example No. | Enzyme reaction inhibitory effect | Cell growth inhibitory effect |
|---|---|---|
| 1 | C | B |
| 2 | A | A |
| 4 | A | A |
| 5 | A | A |
| 6 | A | A |
| 8 | A | A |
| 10 | A | A |
| 11 | A | A |
| 12 | A | A |
| 13 | B | A |
| 14 | A | B |
| 19-1 | A | B |
| 19-2 | B | B |
| 19-3 | A | B |
| 19-4 | B | B |
| 19-5 | B | B |
| 19-6 | B | B |
| 19-7 | A | A |
| 19-8 | A | A |
| 19-9 | B | B |
| 19-10 | B | B |
| 19-11 | A | A |
| 19-12 | A | B |
| 19-13 | A | B |
| 19-14 | A | A |
| 19-15 | A | A |
| 19-16 | B | B |
| 19-17 | A | B |
| 19-18 | B | B |
| 19-19 | B | C |
| 19-20 | B | C |
| 19-21 | B | B |
| 19-22 | B | C |
| 19-23 | B | B |
| 19-24 | B | B |
| 19-25 | A | B |
| 19-26 | B | C |
| 19-27 | B | B |
| 19-28 | A | A |
| 19-29 | B | A |
| 19-30 | A | A |
| 19-31 | B | B |
| 19-32 | B | B |
| 19-33 | B | C |
| 20 | C | B |
| 21 | C | C |

Test Example 3: In Vivo Drug Efficacy Test in Cancer-Bearing Mice (Drug Efficacy Test in Cancer-Bearing Mouse Model with Subcutaneous Transplantation of HL60)

The human acute myeloid leukemia cell line HL60 (available from JCRB) was suspended in a mixture of RPMI-1640 medium and Matrigel (available from Corning Inc.), and then subcutaneously transplanted into 6-week-old female NOD/scid mice (available from CLEA Japan, Inc.). After confirming that the average tumor volume exceeded 200 mm$^3$, the test compound was dissolved in a solvent (1 equivalent sodium hydroxide solution) and orally administered to mice at a dose of 10 to 30 mg/kg once daily for 10 days. As a negative control, a solvent-administered group to which a 10 to 12 mmol/L sodium hydroxide solution was administered was provided. The tumor diameter was measured over time and the tumor volume was calculated. The tumor volume was calculated by measuring the major axis and the minor axis of the tumor and using the following expression.

Tumor volume (mm³)=[major axis (mm)×minor axis (mm)×minor axis (mm)]/2

T/C (%) was calculated from the average tumor volume of each group by the following expression, and the drug efficacy was evaluated.

T/C (%)=(average tumor volume of drug-administered group)/(average tumor volume of solvent-administered group)×100%

As a result of evaluating the drug efficacy, each test compound (for example, the compounds described in Example 2, Example 4, Example 8, Example 10, and Example 13) showed an excellent tumor growth inhibition rate.

The compound of the present invention or a salt thereof has an excellent DHODH inhibitory effect and is useful as a DHODH inhibitor.

In addition, the compound of the present invention or a salt thereof has an excellent anti-tumor activity and is useful as a pharmaceutical composition such as an anti-tumor agent. The compound of the present invention or a salt thereof is useful for treatment such as prevention or treatment of blood cancer.

What is claimed is:

1. A compound represented by general formula (1) or a salt thereof:

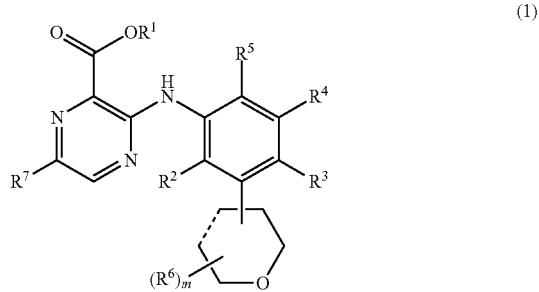

(1)

in the formula,
$R^1$ represents a hydrogen atom or a $C_{1-6}$ alkyl group;
$R^2$, $R^3$, $R^4$, and $R^5$ are the same as or different from each other, and each represent a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted;
$R^6$'s are the same as or different from each other and each represent a halogen atom, a $C_{1-6}$ alkyl group which may be substituted, or a $C_{1-6}$ alkoxy group which may be substituted;
$R^7$ represents a $C_{1-6}$ alkyl group which may be substituted or a $C_{3-8}$ cycloalkyl group which may be substituted;
m represents an integer of 0 to 6; and
a broken line represents a single bond or a double bond.

2. The compound or salt thereof according to claim 1, wherein the compound represented by general formula (1) is a compound represented by general formula (1a):

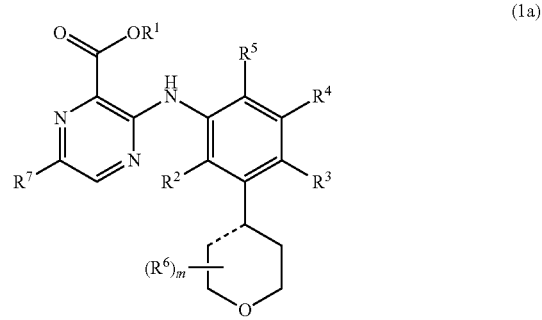

(1a)

in the formula,
$R^1$ represents a hydrogen atom or a $C_{1-6}$ alkyl group;
$R^2$, $R^3$, $R^4$, and $R^5$ are the same as or different from each other, and each represent a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted;
$R^6$'s are the same as or different from each other and each represent a halogen atom, a $C_{1-6}$ alkyl group which may be substituted, or a $C_{1-6}$ alkoxy group which may be substituted;
$R^7$ represents a $C_{1-6}$ alkyl group which may be substituted or a $C_{3-8}$ cycloalkyl group which may be substituted;
m represents an integer of 0 to 6; and
a broken line represents a single bond or a double bond.

3. The compound or salt thereof according to claim 1, wherein $R^1$ is a hydrogen atom.

4. The compound or salt thereof according to claim 1, wherein $R^2$, $R^3$, $R^4$, and $R^5$ are the same as or different from each other and each are a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl) amino group which may be substituted with one or more substituents selected from Substituent group A, or a $C_{1-6}$ alkoxy $C_{1-6}$ alkyl group which may be substituted with one or more substituents selected from Substituent group A, Substituent group A:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent group B; and a heterocyclic group which may be substituted with one or more substituents selected from Substituent group B, Substituent group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

5. The compound or salt thereof according to claim 1, wherein $R^2$ is a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A, Substituent group A:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent group B: and a heterocyclic group which may be substituted with one or more substituents selected from Substituent group B, Substituent group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

6. The compound or salt thereof according to claim 1, wherein $R^3$, $R^4$, and $R^5$ are the same as or different from each other and each are a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A, Substituent group A:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent group B: and a heterocyclic group which may be substituted with one or more substituents selected from Substituent group B, Substituent group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

7. The compound or salt thereof according to claim 1, wherein $R^6$'s are the same as or different from each other and each are a halogen atom, a $C_{1-6}$ alkyl group which may be substituted with one or more substituents selected from Substituent group A, or a $C_{1-6}$ alkoxy group which may be substituted with one or more substituents selected from Substituent group A, Substituent group A:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent group B: and a heterocyclic group which may be substituted with one or more substituents selected from Substituent group B, Substituent group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

8. The compound or salt thereof according to claim 1, wherein $R^7$ is a $C_{1-6}$ alkyl group or a $C_{3-8}$ cycloalkyl group.

9. The compound or salt thereof according to claim 1, wherein $R^7$ is a cyclopropyl group.

10. The compound or salt thereof according to claim 1, wherein m is an integer of 0 to 2.

11. A pharmaceutical composition comprising the compound or salt thereof according to claim 1.

12. An anti-tumor agent comprising the compound or salt thereof according to claim 1.

13. A dihydroorotate dehydrogenase inhibitor comprising the compound or salt thereof according to claim 1.

14. A method for treating a tumor, comprising administering the compound or salt thereof according to claim 1 to a subject.

15. A method for inhibiting dihydroorotate dehydrogenase, comprising administering the compound or salt thereof according to claim 1 to a subject.

* * * * *